(12) United States Patent
Sheng

(10) Patent No.: US 11,666,900 B2
(45) Date of Patent: Jun. 6, 2023

(54) MOTION CONTROLLING MECHANISM, LIQUID DISCHARGING NOZZLE, MICRODROPLET GENERATING DEVICE AND METHOD, LIQUID DRIVING MECHANISM AND METHOD, MICRODROPLET GENERATING METHOD, AND SURFACE PROCESSING METHOD OF LIQUID DISCHARGING NOZZLE

(71) Applicant: Sniper (Suzhou) Life Technology Co, Ltd., Jiangsu (CN)

(72) Inventor: Guang-Ji Sheng, Beijing (CN)

(73) Assignee: Sniper (Suzhou) Life Technology Co., Suzhou (CN)

( * ) Notice: Subject to any disclaimer, the term of this patent is extended or adjusted under 35 U.S.C. 154(b) by 195 days.

(21) Appl. No.: 16/964,599

(22) PCT Filed: Jan. 24, 2019

(86) PCT No.: PCT/CN2019/072926
§ 371 (c)(1),
(2) Date: Jul. 24, 2020

(87) PCT Pub. No.: WO2019/144894
PCT Pub. Date: Aug. 1, 2019

(65) Prior Publication Data
US 2021/0053046 A1 Feb. 25, 2021

(30) Foreign Application Priority Data

Jan. 24, 2018 (CN) .......................... 201810070377.2
Aug. 6, 2018 (CN) .......................... 201810884995.0

(51) Int. Cl.
*B01L 3/02* (2006.01)
(52) U.S. Cl.
CPC .......... *B01L 3/0241* (2013.01); *B01L 3/0286* (2013.01); *B01L 2400/0433* (2013.01)
(58) Field of Classification Search
CPC .... B01L 3/0241; B01L 3/0286; B01L 3/0268; B01L 2400/0433; B01L 2400/021; B01L 2400/0478; B01L 2200/0673; B01L 2300/0838; G01N 35/1016; G01N 2035/1034; C12M 1/00
See application file for complete search history.

(56) References Cited

U.S. PATENT DOCUMENTS

| 6,551,557 | B1 | 4/2003 | Rose et al. |
| 2007/0157628 | A1 | 7/2007 | Onoun |
| 2012/0304929 | A1 | 12/2012 | Ivri |
| 2014/0272982 | A1 | 9/2014 | Yamana et al. |
| 2015/0062824 | A1 | 3/2015 | Hyun et al. |
| 2015/0375239 | A1 | 12/2015 | Herre et al. |
| 2017/0253915 | A1 | 9/2017 | Du et al. |
| 2017/0356036 | A1 | 12/2017 | Davies et al. |

FOREIGN PATENT DOCUMENTS

| CN | 1858201 | A | 11/2006 |
| CN | 1986229 | | 6/2007 |
| CN | 101974421 | A | 2/2011 |
| CN | 102232114 | | 11/2011 |
| CN | 202195997 | U | 4/2012 |
| CN | 103434272 | A | 12/2013 |
| CN | 103717308 | | 4/2014 |
| CN | 104107734 | A | 10/2014 |
| CN | 104324769 | A | 2/2015 |
| CN | 104388307 | | 3/2015 |
| CN | 104450891 | A | 3/2015 |
| CN | 105498869 | A | 4/2016 |
| CN | 105854965 | A | 8/2016 |
| CN | 205501281 | U | 8/2016 |
| CN | 105925572 | | 9/2016 |
| CN | 106520524 | | 3/2017 |
| CN | 106596489 | | 4/2017 |
| CN | 106662374 | A | 5/2017 |
| CN | 106754341 | A | 5/2017 |
| CN | 106755345 | A | 5/2017 |
| CN | 104450891 | | 6/2017 |
| CN | 106854618 | A | 6/2017 |
| CN | 107349882 | A | 11/2017 |
| CN | 107478629 | | 12/2017 |
| CN | 107513495 | | 12/2017 |
| CN | 107586700 | A | 1/2018 |
| CN | 107622185 | | 1/2018 |
| CN | 207596826 | U | 7/2018 |
| CN | 108373971 | A | 8/2018 |

(Continued)

OTHER PUBLICATIONS

International Search Report of PCT/CN2019/072974.
Sofronova J.K. et al. "Detection of Mutations in Mitochondrial DNA by Droplet Digital PCR" Biochemistry (Moscow), vol. 81, No. 10, Oct. 31, 2016(Oct. 31, 2016), pp. 1031-1037.
Lievens A. et al: "Measuring Digital PCR Quality: Performance Parametersand Their Optimization" vol. 11, No. 5, Jun. 5, 2016, p. 3-p. 16.
Scott O. Sundberg et al:"Spining Disk Platform for Microfluidic Digital Polymerease Chain Reaction" Analytical Chemistry, vol. 82, No. 4, Feb. 15, 2010, pp. 1546-1550.
Phenix-Lan Quan et al: "dPRC : A Technology Review" Sensors, vol. 18, No. 4, Apr. 20, 2018, pp. 1271.

(Continued)

*Primary Examiner* — Christopher Adam Hixson
(74) *Attorney, Agent, or Firm* — Cherskov Flaynik & Gurda, LLC

(57) ABSTRACT

Disclosed is a liquid discharging nozzle, including a needle stem having a hollow chamber and an outlet end located at one end of the needle stem, an angle between a normal line of an end surface of the outlet end of the liquid discharging nozzle and an extension direction of the needle stem is equal to or smaller than 90°. Further disclosed are a motion controlling mechanism, a microdroplet generating device and method, a liquid driving mechanism and method, a microdroplet generating method, and a surface processing method of a liquid discharging nozzle.

19 Claims, 23 Drawing Sheets

(56) References Cited

FOREIGN PATENT DOCUMENTS

| | | |
|---|---|---|
| CN | 208131057 | 11/2018 |
| CN | 208378891 | 1/2019 |
| CN | 208494266 | 2/2019 |
| CN | 110066857 A | 7/2019 |
| DE | 102015011970 | 3/2017 |
| EP | 2848698 | 3/2015 |
| EP | 3236269 | 10/2017 |
| JP | 1997139525 A | 5/1997 |
| JP | 2003170425 A | 6/2003 |
| JP | 2003174203 A | 6/2003 |
| JP | 2004279340 A | 10/2004 |
| JP | 2007257014 | 10/2007 |
| JP | 4323528 B2 | 9/2009 |
| JP | 2017013011 A | 1/2017 |
| JP | 2017063779 A | 4/2017 |
| KR | 20100128518 A | 12/2010 |
| WO | WO2002006450 A1 | 1/2002 |
| WO | WO2013049443 | 4/2013 |
| WO | WO2013072069 | 5/2013 |
| WO | WO2013130857 | 9/2013 |
| WO | WO2014/025924 | 2/2014 |
| WO | WO2016/014976 | 1/2016 |
| WO | WO2016/133783 | 8/2016 |
| WO | WO2017007954 A1 | 1/2017 |
| WO | WO2018094081 A | 5/2018 |

OTHER PUBLICATIONS

Kevin A Heyries et al:"Megapixel digital PCR" Mature Methods, vol. 8, No. 8, Jul. 3, 2011, pp. 649-651.
Philip J Wilson et al. "Extending digital PRC analysis by modelling quantification cycle data", «BMC Bioinformatics», Oct. 12, 2016.
Mitra Mojtahedi et al. "Direct elicitation of template concentration from quantification cyale(Cq) distributions in digital PCR", «Nucleic Acids Res», Aug. 7, 2014.
Shufang Zhou et al. "A highly integrated real-time digital PCR device for accurate DNA quantitative analysis", «Biosens Bioelectron», Jan. 11, 2019, pp. 151-158.
Chen Chao, "New Technology and Precise Medical Science", «Shanghai Jiao Tong University Press», Dec. 31, 2016, pp. 150-151.
International Search Report of PCT/CN2019/072969.
International Search Report of PCT/CN2019/072926.
«Scientific Reports» Aug. 29, 2017 Nivedita Majumdar etc. Poission Plus Quantification for Digital PCR Systems. pp. 1-10.

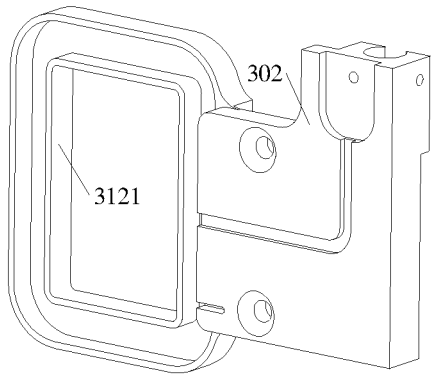
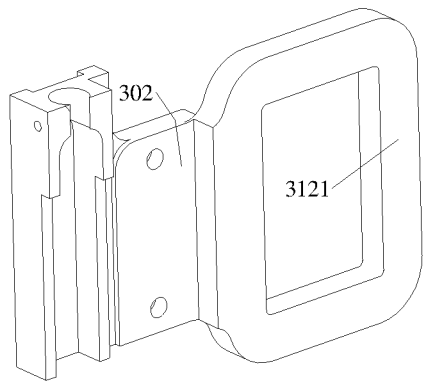
FIG. 46　　　　　　　　　　　FIG. 47
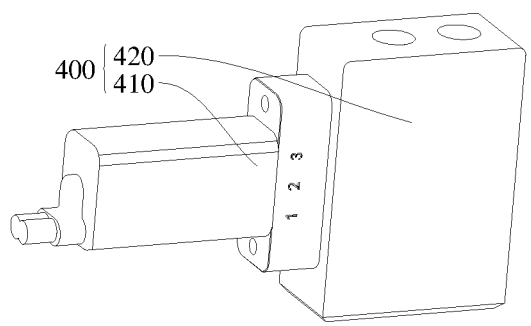
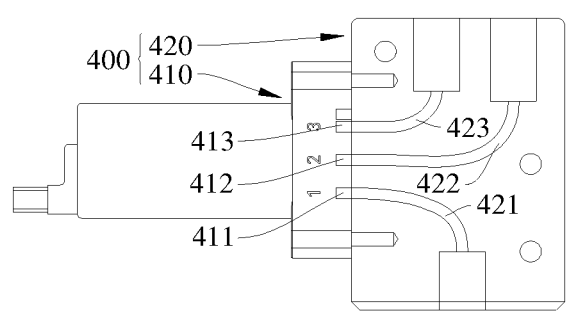
FIG. 48　　　　　　　　　　　FIG. 49

US 11,666,900 B2

MOTION CONTROLLING MECHANISM, LIQUID DISCHARGING NOZZLE, MICRODROPLET GENERATING DEVICE AND METHOD, LIQUID DRIVING MECHANISM AND METHOD, MICRODROPLET GENERATING METHOD, AND SURFACE PROCESSING METHOD OF LIQUID DISCHARGING NOZZLE

CROSS-REFERENCE TO RELATED APPLICATIONS

This application claims priority benefits from China Patent Application No. 201810070377.2, filed on Jan. 24, 2018, entitled "Digital PCR Quantitative Detecting Method", and China Patent Application No. 201810884995.0, filed on Aug. 6, 2018, entitled "Liquid Driving Device and Method". The entireties of these applications are incorporated by reference herein for all purposes. This application is a 35 U.S.C. § 371 national application of international patent application PCT/CN2019/072926 filed on Jan. 24, 2019, the content of which is also hereby incorporated by reference. This application is related to commonly-assigned applications, entitled "Digital PCR Detection Apparatus, Digital PCR Quantitative Detection Method, Multi-Volume Digital PCR Quantitative Analysis Method, Digital PCR Detection Method, Nucleic Acid Detection Microsphere, Preparation Method of Nucleic Acid Detection Microsphere, Nucleic Acid Detection Microsphere Kit and High-Throughput Nucleic Acid Detection Method" Ser. No. 16/964,183 and "Microdroplet Container and Method for Manufacturing the Same, Method for Spreading Microdroplets, Microdroplet-Generating Kit, Temperature-Controlling Device, Oil Phase Composition for Microdroplet Generating and Method For Treating the Same" Ser. No. 16/964,607, the contents of which are also hereby incorporated by reference.

TECHNICAL FIELD

The present application relates to the technical field of measuring and dispensing micro-liquid, particularly to a motion controlling mechanism, a liquid discharging nozzle, a microdroplet generating device and method, a liquid driving mechanism and method, a microdroplet generating method, and a surface processing method of liquid discharging nozzle.

BACKGROUND

Nowadays, the accurate operation of micro-liquids is required in the application fields of medical clinical test, nano-material preparation, food and environment detection, biochemical analysis, and so on. One key technique for the operation of the micro-liquid involves further dividing a liquid with a micro-liter volume into micro-reaction systems with a nano-liter volume or even pico-liter. One main branch technique for generating the micro-reaction system involves generating emulsified microdroplets. In recent years, various techniques for generating the microdroplets, such as the membrane emulsifying method, the spray emulsifying method, the microfluidic chip, and the liquid discharging nozzle injecting/spraying method, have been reported in literature. In these techniques, the liquid discharging nozzle injecting/spraying method, as the latest microdroplet generating technique, has a good application prospect in terms of the generation of microdroplet and the cost control of consumables.

The conventional liquid discharging nozzle is generally in the shape of a straight tube. If a portion of the liquid discharging nozzle proximate to its outlet end in its extending direction moves fast, the generated microdroplet would be broken. Therefore, the vibration frequency of the liquid discharging nozzle has to be decreased to maintain the integrality of the generated microdroplet, thereby causing a decrease in the generation rate of the microdroplets. When the liquid discharging nozzle injecting/spraying method is applied, a motion controlling mechanism drives the outlet end of the liquid discharging nozzle to move relative to an oil phase composition. However, in practice, the conventional controlling mechanism cannot accurately control the relative motion between the outlet end of the liquid discharging nozzle and the oil phase composition, thus the uniformity of the volume sizes of the generated microdroplets is poor. The liquid is discharged at an unstable and uncontrollable flow rate when the outlet end of the liquid discharging nozzle is in a moving state in the generation process of the microdroplets. Therefore, the volume sizes of the generated microdroplets are random. In the conventional liquid discharging nozzle injecting/spraying method, the liquid discharging nozzle needs to move and switch above and below a liquid surface to form the microdroplet. However, an unstable standing wave may be formed on the liquid surface in this method, causing an unstable microdroplet generation process. The surface property of the liquid discharging nozzle is an important factor affecting the generation of the microdroplet. A sectional size of the conventional liquid discharging nozzle is generally of the order of micrometer. The conventional surface processing method is mostly applied to components having relatively large sizes and cannot be fully appropriate for the liquid discharging nozzle having a relatively small size.

SUMMARY

The present application provides a liquid discharging nozzle for generating a microdroplet, which includes a needle stem having a hollow chamber and an outlet end located at one end of the needle stem, wherein an angle between a normal line of an end surface of the outlet end of the liquid discharging nozzle and an extension direction of the needle stem is equal to or smaller than 90°. A microdroplet generating device includes a liquid driving mechanism, a motion controlling mechanism and the liquid discharging nozzle in the solution above, the liquid discharging nozzle stores a first liquid therein and has an outlet end and an inlet end; the fluid driving mechanism is connected to the inlet end of the liquid discharging nozzle and configured to discharge the first liquid stored in the liquid discharging nozzle from the outlet end of the liquid discharging nozzle; and the motion controlling mechanism is configured to control the outlet end of the liquid discharging nozzle to move below a liquid surface of a second liquid along a preset trajectory, or at a preset speed, or with a preset acceleration, so that the first liquid discharged from the outlet end of the liquid discharging nozzle is capable of overcoming a surface tension and an adhesion force to form a microdroplet in the second liquid. A microdroplet generating method, using the liquid discharging nozzle in any above-described solution and storing a first liquid therein, comprises: providing a microdroplet container storing a second liquid therein; controlling the first liquid to be discharged from the outlet end of the liquid discharging nozzle at a constant speed; and controlling the outlet end of the liquid discharging nozzle to periodically move below a liquid surface of the second liquid in the extension direction of the needle stem at a speed varying in a form of a square wave; wherein a speed of the outlet end of the liquid discharging nozzle in a first half motion period and that in a second half motion period of the outlet end of the liquid discharging nozzle are identical but in opposite directions, and the first liquid and the second liquid are any two liquids immiscible with each other or have an interfacial reaction therebetween. A microdroplet generating method, using the liquid discharging nozzle in any above-described solution and storing a first liquid therein, comprises: providing a microdroplet container storing a second liquid therein; controlling the first liquid to be discharged from the outlet end of the liquid discharging nozzle at a constant speed; and controlling the outlet end of the liquid discharging nozzle to periodically move in the second liquid in the extension direction of the needle stem with a displacement changing in a sine form; wherein the first liquid and the second liquid are any two liquids immiscible with each other or have an interfacial reaction therebetween. By using the above-described liquid discharging nozzle, when the liquid discharging nozzle vibrates in the extending direction of the tube body, the microdroplet drops from the outlet end of the liquid discharging nozzle and then moves away from the moving trajectory of the outlet end under the action of a viscous force of the second liquid and of a press of the end face of the outlet end of the liquid discharging nozzle, thereby avoiding the broken of the microdroplet by the outlet end, maintaining the integrality of the generated microdroplet, and allowing the liquid discharging nozzle to fast vibrates in the extending direction of the tube body to rapidly generate the microdroplet.

In view of this, the present application provides a motion controlling mechanism, which includes a supporting frame, a connecting member configured to be connected to a liquid discharging nozzle, and a driving component fixed on the supporting frame, wherein the driving component is connected to and drives the connecting member, and the driving component drives an outlet end of the liquid discharging nozzle to move with a displacement changing in a sine form or at a speed varying in a square wave form. The above-described motion controlling mechanism can drive the outlet end of the liquid discharging nozzle to move with a displacement changing in a sine form or at a speed changing in a square wave form to generate the microdroplet, which has advantages of high microdroplet generating efficiency and high uniformity.

In view of this, the present application provides a liquid driving mechanism for a microdroplet generating system, which includes a volume-variable assembly including a syringe barrel and a push rod, the push rod and an inner wall of the syringe barrel slidably matching, the syringe barrel storing a driving liquid therein and having a liquid inlet/outlet, the liquid inlet/outlet being configured to communicate with an inlet end of a liquid discharging nozzle storing a first liquid therein; and a power assembly, connected to the push rod and configured to drive the push rod to slide in an extension direction of the syringe barrel; wherein in a generation process of a microdroplet, the power assembly drives the push rod to press the driving liquid stored in the syringe barrel, and the driving liquid presses the first liquid stored in the liquid discharging nozzle, thereby discharging the first liquid from an outlet end of the liquid discharging nozzle. A liquid driving method, using the liquid driving mechanism in any above-described solution, includes: the power assembly driving the push rod to press the driving liquid stored in the syringe barrel, the driving liquid pressing the first liquid stored in the liquid discharging nozzle, and the first liquid being discharged from the outlet end of the liquid discharging nozzle. A liquid driving method, using the liquid driving mechanism in any above-described solution, includes communicating, by means of the three-way reversing valve, the liquid inlet/outlet of the volume-variable assembly with the reservoir; driving, by the power assembly the push rod to slide in the syringe barrel to change a volume of the syringe barrel, so as to suck the driving liquid in the reservoir into the syringe barrel; communicating, by means of the three-way reversing valve, the liquid inlet/outlet of the volume-variable assembly with an inlet end of a liquid discharging nozzle; driving, by the power assembly, the push rod to slide in the syringe barrel to change the volume of the syringe barrel, so as to discharge a gas in the syringe barrel and the liquid discharging nozzle; inserting an outlet end of the liquid discharging nozzle into the first liquid; maintaining the three-way reversing valve to allow the liquid inlet/outlet of the volume-variable assembly to be in communication with the inlet end of the liquid discharging nozzle; driving, by the power assembly, the push rod to slide in the syringe barrel to change the volum of the syringe barrel; and sucking the first liquid into the liquid discharging nozzle; and maintaining the three-way reversing valve to allow the liquid inlet/outlet of the volume-variable assembly to be in communication with the inlet end of the liquid discharging nozzle; driving, by the power assembly, the push rod to slide in the syringe barrel to change the volume of the syringe barrel, so as to discharge the first liquid stored in the liquid discharging nozzle from the outlet end of the liquid discharging nozzle at a uniform flow rate. The liquid driving mechanism and method as described above utilize the incompressibility of the driving liquid to ensure the first liquid is able to be discharged from the outlet end of the liquid discharging nozzle at the preset flow rate even though the outlet end of the liquid discharging nozzle vibrates at a high frequency. The volume of the generated microdroplet can be accurately controlled through the liquid driving mechanism provided in the present application.

In view of this, the present application provides a microdroplet generating method, which includes steps of: S201, providing a liquid discharging nozzle having an outlet end and storing a first liquid therein and providing a microdroplet container storing a second liquid therein and having an opening, wherein the first liquid and the second liquid are any two immiscible liquids or any two liquids having an interfacial reaction therebetween; S202, inserting the outlet end of the liquid discharging nozzle below the liquid surface of the second liquid through the opening of the microdroplet container; and S203, controlling the outlet end of the liquid discharging nozzle to move with an instantaneous acceleration below the liquid surface of the second liquid, while discharging the first liquid from the outlet end of the liquid discharging nozzle, so that the first liquid discharged from the outlet end of the liquid discharging nozzle forms a droplet attached to the outlet end of the liquid discharging nozzle, and the droplet is detached from the outlet end of the liquid discharging nozzle during the instantaneous accelerated motion of the outlet end of the liquid discharging nozzle, thereby forming a microdroplet below the liquid surface of the second liquid. In the above-described microdroplet generating method, for the reason that the outlet end of the liquid discharging nozzle has a relatively large value of the instantaneous acceleration, the adhesion force between the droplet attached to the outlet end of the liquid discharging nozzle and the outlet end of the liquid discharging nozzle is insufficient to let the droplet synchronously accelerate with the outlet end of the liquid discharging nozzle, so that the droplet attached to the outlet end of the liquid discharging nozzle is detached from the liquid discharging nozzle, and formed into the microdroplet below the liquid surface of the second liquid. In the microdroplet generating method provided in the present application, the outlet end of the liquid discharging nozzle generates the microdroplet at the moment the outlet end instantaneously accelerates below the liquid surface of the second liquid, which reduces the disturbance to the second liquid when the outlet end of the liquid discharging nozzle moves, and ensures the stability of the microdroplet generation.

In view of this, the present application provides a microdroplet generating method, which includes steps of: S211, providing a liquid discharging nozzle having an outlet end and storing a first liquid therein and providing a microdroplet container storing a second liquid therein and having an opening, wherein the first liquid and the second liquid are any two immiscible liquids or any two liquids having an interfacial reaction therebetween; S212, inserting the outlet end of the liquid discharging nozzle below a liquid surface of the second liquid through the opening of the microdroplet container; and S213, controlling the outlet end of the liquid discharging nozzle to move at a periodically changed speed below the liquid surface of the second liquid, and in a first half period and a second half period of a speed variation, the speed of the outlet end of the liquid discharging nozzle changing monotonously, the first liquid being discharged from the outlet end of the liquid discharging nozzle, the first liquid discharged from the outlet end of the liquid discharging nozzle being formed into a droplet attached to the outlet end of the liquid discharging nozzle, the droplet being detached from the outlet end of the discharging nozzle during the moving of the outlet end of the liquid discharging nozzle, thereby forming a microdroplet below the liquid surface of the second liquid. In the above-described microdroplet generating method, the outlet end of the liquid discharging nozzle makes a motion with a periodically changed speed blow the liquid surface of the second liquid. The speed of the outlet end of the liquid discharging nozzle changes monotonously in both the first half period and the second half period of the speed variation. During the movement, the viscous force exerted upon the droplet by the second liquid also shows a periodic change in accordance with the periodically changed speed of the outlet end of liquid discharging nozzle. When the maximum adhesion force between the outlet end of the liquid discharging nozzle and the droplet is smaller than the viscous force exerted on the droplet by the second liquid, the droplet cannot move synchronously with the outlet end of the liquid discharging nozzle, so that the droplet attached to the outlet end of the discharging nozzle is detached from the outlet end of the liquid discharging nozzle to form the microdroplet below the liquid surface of the second liquid. In the microdroplet generating method provided in the present application, the outlet end of the liquid discharging nozzle makes a periodic motion with a varying velocity below the liquid surface of the second liquid to generate the microdroplet, which reduces the disturbance to the second liquid when the outlet end of the liquid discharging nozzle moves, and ensures the stability of the generation of the microdroplet.

In view of this, the present application provides a surface processing method of a liquid discharging nozzle, applicable for processing a surface of the liquid discharging nozzle, includes steps of: S260, silanizing the liquid discharging nozzle; S270, treating the liquid discharging nozzle with an aqueous solution of diethyl pyrocarbonate; and S280, drying the liquid discharging nozzle. In the above-described surface processing method of the liquid discharging nozzle, the surface free energy of the liquid discharging nozzle decreases and can be controlled within a certain range via the silanization, thereby decreasing the effect of the surface property of the liquid discharging nozzle on the generation process of the microdroplet.

In view of this, the present application provides a liquid driving mechanism for a microdroplet generating system, which includes: a housing; a first volume-variable assembly disposed in the housing and comprising a first syringe barrel and a first push rod, wherein the first push rod is slidably coupled with an inner wall of the first syringe barrel, and the first syringe barrel is configured to store a first driving liquid therein and has a liquid inlet/outlet configured to communicate with an inlet end of a first liquid discharging nozzle storing a third liquid therein; and a linear motor assembly, disposed in the housing, having an output end connected to the first push rod and configured to drive the first push rod to slide in an extension direction of the first syringe barrel. A liquid driving method, using the liquid driving mechanism, includes: communicating the inlet/outlet port of the first syringe barrel with the reservoir via the reversing valve, and driving the first push rod by the linear motor assembly to slide in the first syringe barrel to change a volume of the first syringe barrel, so as to suck the first driving liquid in the reservoir into the first syringe barrel; communicating the inlet/outlet port of the first syringe barrel with an inlet end of the first liquid discharging nozzle via the reversing valve, and driving the first push rod by the linear motor assembly to slide in the first syringe barrel to change the volume of the first syringe barrel, so as to discharge a gas in the first syringe barrel and the first liquid discharging nozzle; inserting an outlet end of the first liquid discharging nozzle into the third liquid, maintaining the communication between the inlet/outlet port of the first syringe barrel and the inlet end of the first liquid discharging nozzle via the reversing valve, and driving the first push rod by a power assembly to slide in the first syringe barrel to change the volume of the first syringe barrel, so as to suck the third liquid into the first liquid discharging nozzle; and maintaining the communication between the inlet/outlet port of the first syringe barrel and the inlet end of the first liquid discharging nozzle via the reversing valve, and driving the first push rod by the linear motor assembly to slide in the first syringe barrel to change the volume of the first syringe barrel, so as to discharge the third liquid stored in the first liquid discharging nozzle from the outlet end of the liquid first discharging nozzle with a preset flow rate. The liquid driving mechanism and method as described above utilize the incompressibility of first driving liquid to ensure that the third liquid is able to be discharged from the outlet end of the first liquid discharging nozzle at the preset flow rate even though the outlet end of the first liquid discharging nozzle vibrates at a high frequency. The linear motor assembly not only has a relatively high motion accuracy, but also enables the magnitude of the current to be adjusted conveniently according to the actual operation conditions, such as the liquid discharging speed, the liquid discharging pressure, and so on, to ensure the first push rod can slide at a preset speed or for a preset distance, thereby allowing the third liquid to be discharged from the outlet end of the first liquid discharging nozzle accurately at the preset flow rate and flow quantity. The volume of the generated microdroplet can be accurately controlled via the liquid driving mechanism provided by the present application.

BRIEF DESCRIPTION OF THE DRAWINGS

In order to clearly explain technical solutions of the present application or in prior art, the following drawings, which are to be referred in the description of the embodiments or in the prior art, are briefly described below. Obviously, the drawings in the following description only show some embodiments of the present application, and those skilled in the art can obtain other drawings according to the following drawings without any creative work.

FIG. 46 is a first schematic side view of an integrally formed frame and connecting plate according to an embodiment of the present application;

FIG. 47 is a second schematic side view of the integrally formed skeleton and connecting plate according to an embodiment of the present application;

FIG. 48 is a schematic structural side view of a reversing valve provided by an embodiment of the present application;

FIG. 49 is a schematic front view of a sectional structure of the reversing valve provided by an embodiment of the present application;

DETAILED DESCRIPTION

The technical solutions according to the embodiments of the present application are described clearly and completely as follows with reference to the drawings of the embodiments of the present application. It is obvious that the described embodiments are only a few but not all of embodiments of the present application. All other embodiments obtained by those skilled in the art based on these embodiments of the present application without any creative work belong to the scope of protection of the present application.

For a clear understanding of the objectives, technical solutions, and advantages of the present application, specific embodiments of the present application will now be described in detail with reference to the accompanying drawings. It should be understood that the following description is merely exemplary embodiments of the present application, and is not intended to limit the scope of the present application.

Figure 1:
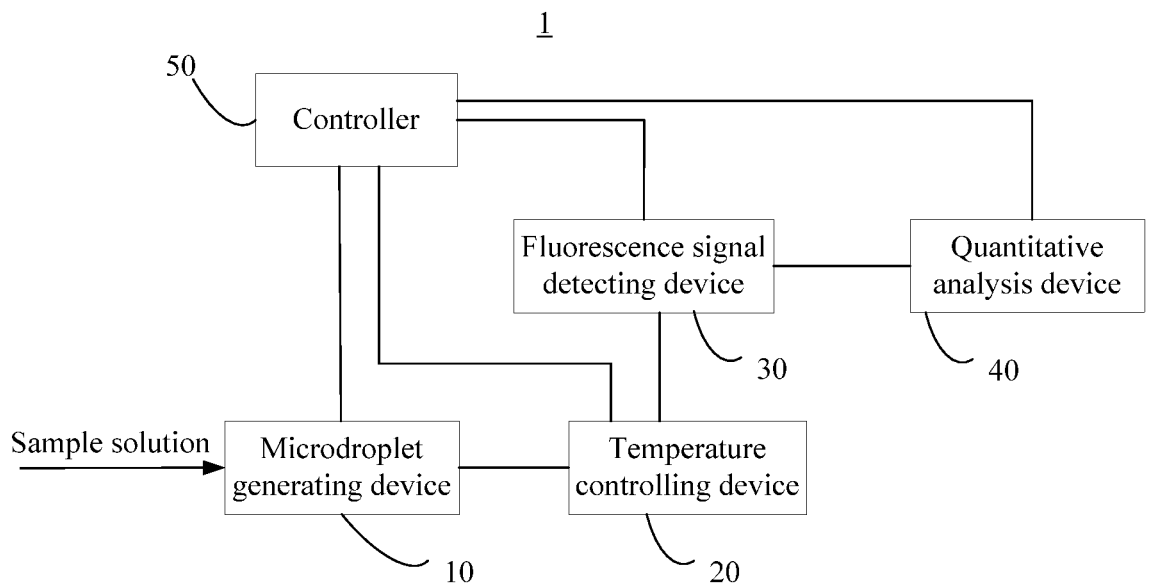
FIG. 1 is an overall schematic structural view illustrating a digital PCR detection apparatus provided by an embodiment of the present application.

Referring to FIG. 1, in an embodiment, a digital PCR detection apparatus 1 is provided in the present application. The digital PCR detection apparatus 1 includes a microdroplet generating device 10, a temperature controlling device 20, a fluorescence signal detecting device 30, a quantitative analysis device 40, and a controller 50. The microdroplet generating device 10 is configured to form a nucleic acid amplification reaction liquid into a plurality of microdroplets. The microdroplet generating device 10 is connected to the temperature controlling device 20 via a track, so that the plurality of microdroplets can be transferred to the temperature controlling device 20 to undergo a temperature cycling to achieve a nucleic acid amplification. The fluorescence signal detecting device 30 is disposed opposite to the temperature controlling device 20 to photographically detect the plurality of microdroplets after the nucleic acid amplification. The quantitative analysis device 40 communicates with the fluorescence signal detecting device 30 via a data cable transmitting fluorescence information of the plurality of microdroplets, so as to perform a quantitative analysis. The controller 50 is respectively connected to the microdroplet generating device 10, the temperature controlling device 20, the fluorescence signal detecting device 30, and the quantitative analysis device 40, so as to control the microdroplet generating device 10, the temperature controlling device 20, the fluorescence signal detecting device 30, and the quantitative analysis device 40.

The digital PCR detection apparatus 1 can integrate the microdroplet generating device 10, the temperature controlling device 20, the fluorescence signal detecting device 30, and the quantitative analysis device 40, thereby allowing an operator to implement automatic operations. The digital PCR detection apparatus 1 has relatively high working efficiency.

In operation of the digital PCR detection apparatus 1, the microdroplet generating device 10 can form the nucleic acid amplification reaction liquid to be detected into the plurality of microdroplets. The temperature controlling device 20 can amplify the nucleic acids in the plurality of microdroplets. The fluorescence signal detecting device 30 takes images showing variations in fluorescence of the plurality of microdroplets in real time. Fluorescence variation curves of the plurality of microdroplets can be obtained from the images showing variations in fluorescence of the plurality of microdroplets. Ct values of the plurality of microdroplets can be obtained according to the fluorescence variation curves. Moreover, a quantitative analysis can be performed for an initial DNA concentration according to the relationship between the Ct value and an initial copy number. The Ct value refers to a number of the temperature cycles that each microdroplet has undergone when its fluorescence signal reaches a preset threshold.

The nucleic acid amplification reactions for the plurality of microdroplets are carried out in the temperature controlling device 20, and the signals, such as the fluorescence signals, ultraviolet absorption signals, turbidity signals and so on, of products in the plurality of microdroplets after the nucleic acid amplification reactions are collected by the fluorescence signal detecting device 30. The number of the microdroplets in which amplifications of target sequences are achieved can be analyzed by comparing a composition difference between the multiple microdroplets amplified and non-amplified, thus finally achieving the quantitative analysis of the nucleic acid molecules. The detection result, obtained by observing the images showing variations in fluorescence of the plurality of microdroplets in real time, is direct, so that the problems of false positive results and false negative results in the plurality of microdroplets can be solved.

The digital PCR detection apparatus 1 integrates the microdroplet generating device 10, the temperature controlling device 20, the fluorescence signal detecting device 30, and the quantitative analysis device 40, allowing the operator to implement automatic operations, so that not only the working efficiency is increased, but also the advantages of rapid reaction, good repeatability, high sensitivity, excellent specificity, and clear result are achieved.

Nowadays, the accurate operation for the micro-liquid is widely needed in the application fields of medical clinical test, nano-material preparation, food and environment detection, biochemical analysis, and so on. One of key techniques of the operation for the micro-liquid involves further dividing a liquid with a micro-liter volume into droplets with at a nano-liter volume or even pico-liter volume to serve as a micro-reaction system. One of main branch techniques for generating the micro-reaction system involves generating emulsified microdroplets.

In recent years, various techniques for generating the microdroplets, such as the membrane emulsifying method, the spray emulsifying method, the microfluidic chip, and the liquid discharging nozzle injecting/spraying method, have been reported in literature. However, in practical application, the methods for generating the emulsified microdroplets by the liquid-discharging nozzle have respective disadvantages. In some methods, a fluid shear stress and an interfacial energy, during the transformation of an interface between a gas phase and a liquid phase, of a micro-liquid can be utilized to overcome a surface tension force and an adhesion force of the liquid at an outlet of the liquid-discharging nozzle, thereby allowing the liquid flowing out of the outlet of the liquid-discharging nozzle to smoothly detach from the liquid-discharging nozzle to form a droplet with a controllable size in a immiscible liquid. However, in these methods, the liquid-discharging nozzle needs to move and switch above and below a liquid surface, and an initial position and a final position of the liquid-discharging nozzle relative to the liquid surface need to be highly accurately located, which is difficult to realize in industry. In the process of the liquid-discharging nozzle rapidly and repeatedly moving into and out of the liquid phase in these methods, the surface of the liquid phase tends to form an unstable standing wave, thereby limiting the generation rate of the microdroplets. In other methods, the liquid discharging nozzle moves circumferentially or spirally with a constant speed in the liquid to produce a shear force to cut off the injected immiscible liquid to form the droplet. However, in these methods, the size of the droplet generated by the liquid discharging nozzle is greatly affected by various system factors, such as a viscosity of the liquid, a temperature of the environment, a moving speed, a moving trajectory, and so on, thus causing an error. Such an error will be accumulated along with the increasing of a number of the droplets generated, therefore, it is very difficult to control the uniformity of the volume sizes of a large batch of microdroplets.

In view of this, to solve the problems occurring in the process of generating the microdroplets by using the conventional microdroplet generating method and device, i.e., the problem that the generation rate of the microdroplets is low, and that it is difficult to control the uniformity of the volume sizes of the microdroplets generated, the present application provides a microdroplet generating method and a microdroplet generating device which can rapidly generate microdroplets with highly uniform volume sizes.

Figure 2:
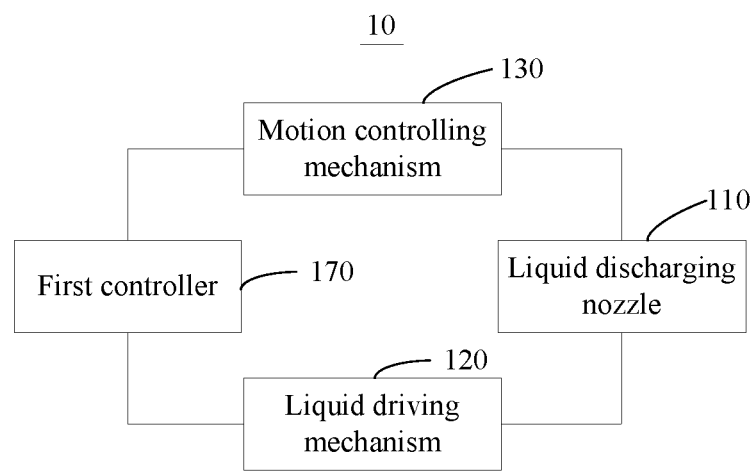
FIG. 2 shows a microdroplet generating device of the digital PCR detection apparatus provided by an embodiment of the present application.

Referring to FIG. 2, the microdroplet generating device 10 in an embodiment includes a liquid discharging nozzle 110, a liquid driving mechanism 120, a motion controlling mechanism 130, and a first controller 170. The liquid discharging nozzle 110 has an inlet end and an outlet end, and is configured to store a first liquid. The microdroplet generating device 10 can be used in combination with a microdroplet container containing a second liquid therein. The outlet end of the liquid discharging nozzle 110 is inserted below a liquid surface of the second liquid.

The first liquid and the second liquid are immiscible with each other or have an interfacial reaction therebetween. The first liquid and the second liquid can be any two immiscible liquids. In an embodiment of the present application, the first liquid is an aqueous solution, and the second liquid is an oil liquid that is immiscible with water, such as a mineral oil (including n-tetradecane, etc.), a vegetable oil, a silicone oil, a perfluoroalkane oil, and so on; and the generated droplets are aqueous solution droplets. Alternatively, the first liquid is a mineral oil, for example, an organic phase such as tetradecane and n-hexane, and the second liquid is a perfluoroalkane oil that is immiscible with the mineral oil. The first liquid and the second liquid can be two immiscible aqueous phases. In another embodiment of the present application, the first liquid is an aqueous solution, and the second liquid is an aqueous liquid that is immiscible with water. For example, the first liquid is a dextran solution; the second liquid is a polyethylene glycol (PEG) aqueous solution; and the generated droplets are dextran solution droplets.

The first liquid and the second liquid can also be two liquids having an interfacial reaction therebetween. In an embodiment of the present application, the first liquid is a sodium alginate aqueous solution, the second liquid is a calcium oxide aqueous solution with a mass concentration of, for example, 1%; an interfacial reaction exits between the sodium alginate aqueous solution and the calcium oxide aqueous solution, and the generated droplets are calcium alginate gel microspheres. In the present application, a plurality of droplets having different compositions and volumes can be generated in sequence in an open vessel by replacing the liquid discharging nozzle or changing the composition of the first liquid flowing from the liquid discharging nozzle, which cannot only be applied to achieve a large batch of high-throughput micro-volume screening, but also achieve a multi-step ultramicro-biochemical reaction and detection, thereby having a broad prospect of application.

The fluid driving mechanism 120 is connected to the inlet end of the liquid discharging nozzle 110 and configured to discharge the first liquid stored in the liquid discharging nozzle 110 from the outlet end of the liquid discharging nozzle 110. The motion controlling mechanism 130 is configured to control the outlet end of the liquid discharging nozzle 110 to move relative to the second liquid in a preset trajectory, or at a preset speed, or with a preset acceleration, so that the first liquid discharged from the outlet end of the liquid discharging nozzle 110 can overcome the surface tension and overcome the adhesion force of the liquid discharging nozzle 110 on the first liquid to form the microdroplet. The first controller 170 is respectively connected to the fluid driving mechanism 120 and the motion controlling mechanism 130 to control the fluid driving mechanism 120 and the motion controlling mechanism 130 to work cooperatively.

Microdroplet generating techniques, such as the membrane emulsifying method, the spray emulsifying method, the microfluidic chip, and the liquid discharging nozzle injecting/spraying method, have been reported in some literature. In these techniques, the liquid discharging nozzle injecting/spraying method, as the newest microdroplet generating technique, has a good application prospect in terms of the generation of microdroplet and the cost control of consumables. In the conventional liquid discharging nozzle injecting/spraying method, the liquid-discharging nozzle needs to move and switch above and below a liquid surface to form the microdroplet. However, an unstable standing wave can be formed on the liquid surface in this method, causing an unstable microdroplet generation process.

In view of the problem of unstable microdroplet generation process existing in the conventional liquid discharging nozzle injecting/spraying method, a microdroplet generating method which can stably generate microdroplets is provided.

Figure 3:
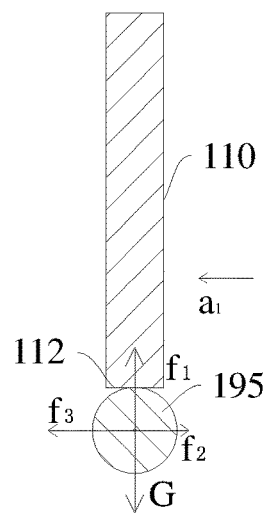
FIG. 3 is a schematic view of forces exerted on a droplet when an outlet end of a liquid discharging nozzle moves according to an embodiment of the present application.

Referring to FIG. 3, in an embodiment of the present application, the motion controlling mechanism 130 can drive the outlet end 112 of the liquid discharging nozzle 110 to move with an instantaneous acceleration below the liquid surface of the second liquid, wherein an acceleration value is $a_1$. The first liquid discharged from the outlet end 112 of the liquid discharging nozzle 110 forms a droplet 195 attached to the outlet end 112 of the liquid discharging nozzle 110. The droplet 195 is detached from the outlet end 112 of the liquid discharging nozzle 110 and forms the microdroplet at the moment the outlet end 112 of the liquid discharging nozzle 110 instantaneously accelerates. The forces exerted upon the microdroplet before the microdroplet is detached from the outlet end 112 of the liquid discharging nozzle 110 are respectively the gravity G, a buoyancy $f_1$ from the second liquid, a viscous resistance $f_2$ from the second liquid, and a maximum adhesion force $f_3$ between the outlet end 112 of the liquid discharging nozzle 110 and the droplet 195. A mass of the microdroplet before being detached from the outlet end 112 of the liquid discharging nozzle 110 is m. The acceleration value of the microdroplet is $a_2$. $m\vec{a}_2=\vec{G}+\vec{f}_1+\vec{f}_2+\vec{f}_3$ is obtained according to Newton's second law of motion.

The maximum adhesion force $f_3$ of the between the outlet end 112 of the liquid discharging nozzle 110 and the droplet 195 is related to the surface free energy of the liquid discharging nozzle 110, the surface tension of the droplet 195, and the geometric dimension of the liquid discharging nozzle 110. When the outlet end 112 of the liquid discharging nozzle 110 instantaneously accelerates, a direction of the adhesion force of the outlet end 112 of the liquid discharging nozzle 110 on the droplet 195 is the same as a direction of the acceleration. The droplet 195 attached to the outlet end 112 of the liquid discharging nozzle 110 is simplified as a sphere. According to the Stokes formula, the viscous resistance $f_2$ exerted upon the droplet 195 moving in the second liquid satisfies $f_2=6\pi\eta rv$, wherein η denotes a viscous coefficient of the second liquid, r denotes a radius of the droplet 195, and v denotes a moving speed of the droplet 195. The speed of the droplet 195 is zero before the outlet end 112 of the liquid discharging nozzle 110 instantaneously accelerates, and thus the viscous resistance $f_2$ exerted upon the droplet 195 by the second liquid at the moment the outlet end 112 of the liquid discharging nozzle 110 instantaneously accelerates is zero or extremely small. In the generation process of the microdroplet, a volume of the droplet 195 is generally in a range from the picoliter magnitude order to the microliter magnitude order, and the buoyancy $f_1$ from the second liquid has a direction opposite to that of the gravity G of the droplet 195; therefore, a vector sum of the buoyancy $f_1$ from the second liquid and the gravity G of the droplet 195 is approximately zero. The viscous resistance $f_2$ is zero or extremely small, and the vector sum of the buoyancy $f_1$ and the gravity G is approximately zero, therefore $\vec{G}+\vec{f}_1+\vec{f}_2+\vec{f}_3\ \vec{f}_3$. According to the Newton's second law of motion, when the outlet end 112 of the liquid discharging nozzle 110 instantaneously accelerates, the maximum acceleration value achievable by the droplet 195 in the second liquid is $a_2 \approx f_3/m$, wherein m is the mass of the droplet 195. When the acceleration value $a_2$ of the droplet 195 is smaller than the acceleration value $a_1$ of the outlet end 112 of the liquid discharging nozzle 110, the droplet 195 drops from the outlet end 112 of the liquid discharging nozzle 110 and forms the microdroplet. Thus, the condition for detaching the droplet 195 from the outlet end 112 of the liquid discharging nozzle 110 (i.e. for generating one microdroplet) is roughly $a_2 \approx (f_3/m) < a_1$.

The motion controlling mechanism 130 can accurately control a magnitude of the instantaneous acceleration of the outlet end 112 of the liquid discharging nozzle 110. Therefore, the droplets 195 can be effectively generated from the instantaneous accelerated motion of the outlet end 112 of the liquid discharging nozzle 110 by controlling the outlet end 112 of the liquid discharging nozzle 110 to have a relatively large value of every instantaneous acceleration.

In view of the above, a microdroplet generating method is further provided in the present application. The method includes steps of:

S201, providing the liquid discharging nozzle 110 having the outlet end 112, wherein the first liquid is stored in the liquid discharging nozzle 110; providing a microdroplet container containing the second liquid therein and having an opening, wherein the first liquid and the second liquid are any two immiscible liquids or any two liquids having the interfacial reaction therebetween;

S202, inserting the outlet end 112 of the liquid discharging nozzle 110 below the liquid surface of the second liquid through the opening of the microdroplet container;

S203, controlling the outlet end 112 of the liquid discharging nozzle 110 to move with the instantaneous acceleration below the liquid surface of the second liquid, while discharging the first liquid from the outlet end 112 of the liquid discharging nozzle 110, so that the first liquid discharged from the outlet end 112 of the liquid discharging nozzle 110 forms the droplet 195 attached to the outlet end 112 of the liquid discharging nozzle 110, and the droplet 195 is detached from the outlet end 112 of the liquid discharging nozzle 110 during the instantaneous accelerated motion of the outlet end 112 of the liquid discharging nozzle 110, thereby forming the microdroplet below the liquid surface of the second liquid.

In the microdroplet generating method above, for the reason that the outlet end 112 of the liquid discharging nozzle 110 has a relatively large value of the instantaneous acceleration, the adhesion force between the droplet 195 attached to the outlet end 112 of the liquid discharging nozzle 110 and the outlet end 112 of the liquid discharging nozzle 110 is insufficient to let the droplet 195 synchronously accelerate with the outlet end 112 of the liquid discharging nozzle 110, so that the droplet 195 attached to the outlet end 112 of the liquid discharging nozzle 110 is detached from the liquid discharging nozzle 110, and formed into the microdroplet below the liquid surface of the second liquid. In the microdroplet generating method provided in the present application, the outlet end 112 of the liquid discharging nozzle 110 generates the microdroplet at the moment the outlet end 112 instantaneously accelerates below the liquid surface of the second liquid, which reduces the disturbance to the second liquid when the outlet end 112 of the liquid discharging nozzle 110 moves, and ensures the stability of the microdroplet generation.

Optionally, in step S203, the manner in which the first liquid is discharged from the outlet end 112 of the liquid discharging nozzle 110 can be a continuous discharge or a discontinuous discharge. The specific discharge manner can be designed according to the actual operating conditions. In this embodiment, in step S203, the first liquid is continuously discharged from the outlet end 112 of the liquid discharging nozzle 110, so that every instantaneous accelerated motion of the outlet end 112 of the liquid discharging nozzle 110 can be fully utilized to generate the microdroplet. In an embodiment, in step S203, the first liquid is discharged from the outlet end 112 of the liquid discharging nozzle 110 at a constant flow rate, that is, the volumes of the first liquid discharged from the outlet end 112 of the liquid discharging nozzle 110 in equal time intervals are always equal to each other. The discharging of the first liquid at the constant flow rate from the outlet end 112 of the liquid discharging nozzle 110 is beneficial for realizing the controlling of the microdroplet generation through controlling the motion of the outlet end 112 of the liquid discharging nozzle 110.

In an embodiment of the present application, in the step S203, the outlet end 112 of the liquid discharging nozzle 110 makes a periodic motion including the instantaneous accelerated motion below the liquid surface of the second liquid. When the outlet end 112 of the liquid discharging nozzle 110 periodically moves below the liquid surface of the second liquid, that is, the displacement, the velocity, and the acceleration of the outlet end 112 of the liquid discharging nozzle 110 are periodically changed. The microdroplets can be generated within an equal time interval from the periodic motion including the instantaneous accelerated motion in combination with the discharge of the first liquid from the outlet end 112 of the liquid discharging nozzle 110 at a constant flow rate. Alternatively, the first liquid is discharged from the outlet end 112 of the liquid discharging nozzle 110 is at a varied flow rate, while the volume of the first liquid discharged from the outlet end 112 of the liquid discharging nozzle 110 is constant in every motion period of the outlet end 112 of the liquid discharging nozzle 110, so as to ensure that, before the outlet end 112 of the liquid discharging nozzle 110 instantly accelerates each time, the droplet 195 has the same volume, thereby generating microdroplets with an uniform volume.

The surface free energy of the liquid discharging nozzle 110, the geometric dimension of the liquid discharging nozzle 110, and the surface tension of the droplet 195, as factors which affect the maximum adhesion force $f_3$ between the outlet end 112 of the liquid discharging nozzle 110 and the droplet 195, are determined if the liquid discharging nozzle 110 and the first liquid are not changed. Therefore, the maximum value $f_3$ of the adhesion force between the outlet end 112 of the liquid discharging nozzle 110 and the droplet 195 is fixed if the liquid discharging nozzle 110 and the first liquid are not changed. The fluid driving mechanism 120 can drive the first liquid to be continuously discharged from the outlet end 112 of the liquid discharging nozzle 110 at a uniform flow rate. The motion controlling mechanism 130 can accurately control the moment, at which the outlet end 112 of the liquid discharging nozzle 110 makes an accelerated motion with the instantaneous acceleration $a_1$, and accurately control the value of the instantaneous acceleration $a_1$. Under the cooperation of the fluid driving mechanism 120 and the motion controlling mechanism 130, it is easy to drive the outlet end 112 of the liquid discharging nozzle 110 to accelerate with the instantaneous acceleration $a_1$ at the moment the volume of the droplet 195 reaches the set value, so as to generate the microdroplets with the uniform volume. If the first liquid is evenly and continuously discharged from the outlet end 112 of the liquid discharging nozzle 110 under the control of the fluid driving mechanism 120, the microdroplets with the uniform volume can be generated by only driving the outlet end 112 of the liquid discharging nozzle 110 to make the instantaneous accelerated motions at the equal time intervals via the motion controlling mechanism 130.

The surface free energy of the liquid discharging nozzle 110 and the geometric dimension of the liquid discharging nozzle 110, as two factors which affect the maximum adhesion force $f_3$ between the outlet end 112 of the liquid discharging nozzle 110 and the droplet 195, are varied if multiple liquid discharging nozzles 110 are used to generate the microdroplets simultaneously or in sequence. However, the variation of the surface free energy of liquid discharging nozzles 110 and the geometric dimensions of the liquid discharging nozzles 110 can be controlled within a certain range via batch processing. The surface tension of the droplet 195, as another factor that affects the maximum adhesion force $f_3$ between the outlet end 112 of the liquid discharging nozzle 110 and the droplet 195, is also varied within a very small range. Therefore, the maximum value $f_3$ of the adhesion force between the outlet end 112 of the liquid discharging nozzle 110 and the droplet 195 fluctuates within a very small range. The fluid driving mechanism 120 can drive the first liquid to be continuously discharged from the outlet end 112 of the liquid discharging nozzle 110 at a uniform flow rate. The motion controlling mechanism 130 can accurately control the moment, at which the outlet end 112 of the liquid discharging nozzle 110 accelerates with the instantaneous acceleration $a_1$, and accurately control the magnitude of the instantaneous acceleration $a_1$. Under the cooperation of the fluid driving mechanism 120 and the motion controlling mechanism 130, it is easy to drive the outlet end 112 of the liquid discharging nozzle 110 to make the instantaneous accelerated motions with the instantaneous acceleration $a_1$ at the moments the volumes of the droplets 195 reach the set value, so as to generate the microdroplets with the uniform volume. If the first liquid is evenly and continuously discharged from the outlet end 112 of the liquid discharging nozzle 110 under the control by the fluid driving mechanism 120, the microdroplets with the uniform volume can be generated by only driving the outlet end 112 of the liquid discharging nozzle 110 to make the instantaneous accelerated motions at the equal time intervals via the motion controlling mechanism 130.

While the fluid driving mechanism 120 discharges the first liquid evenly from the outlet end 112 of the liquid discharging nozzle 110, the motion controlling mechanism 130 cooperatively drives the outlet end 112 to make the instantaneous accelerated motion with a relatively large acceleration value at the moment the volume of the droplet 195 reaches the set value. The microdroplet generating method provided in the present application can ensure not only a volume uniformity of the microdroplets generated by using the same liquid discharging nozzle 110, but also a volume uniformity of the microdroplets generated simultaneously or in sequence by using a plurality of the liquid discharging nozzles 110. The microdroplet generating method provided in this embodiment can increase the generating efficiency by using a plurality of the liquid discharging nozzles 110 to generate the microdroplets at the same time while ensuring the uniformity of the volumes of the microdroplets.

In an embodiment, under the control of the motion controlling mechanism 130, one periodic motion of the outlet end 112 of the liquid discharging nozzle 110 includes multiple instantaneous accelerated motions with the same acceleration value; and one period of the motion of the outlet end 112 of the liquid discharging nozzle 110 is equally divided by the multiple instantaneous accelerated motions. Due to the multiple instantaneous accelerated motions included in one motion period of the outlet end 112 of the liquid discharging nozzle 110, a plurality of microdroplets can be generated in the same period of the motion of the outlet end 112 of the liquid discharging nozzle 110. Optionally, in the step S203, the moving trajectory of the outlet end 112 of the liquid discharging nozzle 110 below the liquid surface of the second liquid includes one of or a combination of various trajectories such as a straight line segment, an arc-shaped line segment, or a polygon. As an implementation manner, when one periodic motion of the outlet end 112 of the liquid discharging nozzle 110 includes two instantaneous accelerated motions, the moving trajectory of liquid discharging nozzle 110 is a straight line or an arc. When one periodic motion of the outlet end 112 of the liquid discharging nozzle 110 includes more than two instantaneous accelerated motions, the moving trajectory of the outlet end 112 of the liquid discharging nozzle 110 in the second liquid is a regular polygon such as a regular triangle, a square, a regular pentagon, a regular hexagon, and so on.

Figure 4:
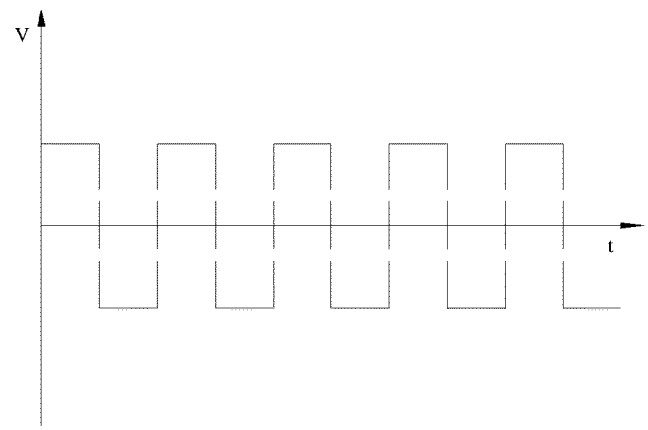
FIG. 4 is a schematic view illustrating a varying speed of the outlet end of the liquid discharging nozzle provided by an embodiment of the present application.

As an implementation manner, in the step S203, during the periodic motion of the outlet end 112 of the liquid discharging nozzle 110 below the liquid surface of the second liquid, the speed of the outlet end 112 of the liquid discharging nozzle 110 varies in the form of a rectangular wave. Since the outlet end 112 of the liquid discharging nozzle 110 has its speed varied in form of the rectangular wave, it enters into a constant speed phase immediately after the acceleration phase, which is favorable for the motion controlling mechanism 130 to accurately control the motion state of the outlet end 112 of the liquid discharging nozzle 110. Optionally, in the rectangular wave indicating the variation of the moving speed of the outlet end 112 of the liquid discharging nozzle 110, the time period of the high level of the wave and the time period of the low level of the wave can be identical or different. Furthermore, in the step S203, during the periodic motion of the outlet end 112 of the liquid discharging nozzle 110 below the liquid surface of the second liquid, the speed of the outlet end 112 of the liquid discharging nozzle 110 varies in a form of a square wave. In the square wave indicating the variation of the moving speed of the outlet end 112 of the liquid discharging nozzle 110, the time period of the high level of the wave and the time period of the low level of the wave are identical. At the low level of the rectangular wave indicating the variation of the moving speed of the outlet end 112 of the liquid discharging nozzle 110, the speed of the outlet end 112 of the liquid discharging nozzle 110 is zero, or a direction of the velocity is opposite to the direction of the velocity at the high level. Referring to FIG. 4, furthermore, the speed of the outlet end 112 of the liquid discharging nozzle 110 in the first half motion period and that in the second half motion period of the outlet end 112 of the liquid discharging nozzle 110 are identical but in opposite directions. There are two instantaneous accelerated motions in opposite directions in one motion period of the outlet end 112 of the liquid discharging nozzle 110.

In an embodiment, the moving trajectory of the outlet end 112 of the liquid discharging nozzle 110 below the liquid surface of the second liquid is a straight line segment. The outlet end 112 of the liquid discharging nozzle 110 makes one instantaneous accelerated motion at one endpoint of the straight line segment and makes another instantaneous accelerated motion in the opposite direction at the other endpoint of the straight line segment. The acceleration values of the two instantaneous accelerated motions are both $a_1$. In another embodiment, the moving trajectory of the outlet end 112 of the liquid discharging nozzle 110 below the liquid surface of the second liquid is an arc or a polygon. Furthermore, in the step S203, the outlet end 112 of the liquid discharging nozzle 110 periodically moves below the liquid surface of the second liquid with a frequency between 0.1 Hz to 200 Hz, which can easily be realized in practice.

Figure 5:
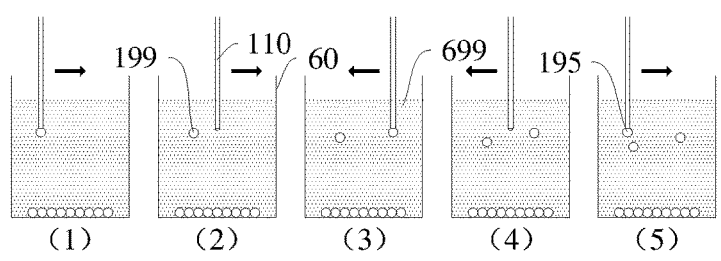
FIG. 5 is a schematic view illustrating a generation process of a microdroplet when the outlet end of the liquid discharging nozzle moves according to an embodiment of the present application.

Referring to FIGS. 4 and 5, in a specific embodiment of the present application, the first liquid is discharged from the outlet end 112 of the liquid discharging nozzle 110 at a constant flow rate under the control of the liquid driving mechanism 120. The outlet end of the liquid discharging nozzle 110 periodically moves along a moving trajectory of a straight line and at a speed varying in a form of a square wave under the control of the motion controlling mechanism 130. The instantaneous acceleration of the outlet end 112 of the liquid discharging nozzle 110 reaches its maximum value at the moment the direction of the velocity of the outlet end 112 of the liquid discharging nozzle 110 changes. The droplet 195 attached to the outlet end 112 of the liquid discharging nozzle 110 is detached from the outlet end 112 of the liquid discharging nozzle 110 to form the microdroplet 199 at the moment the instantaneous acceleration of the outlet end 112 of the liquid discharging nozzle 110 reaches its maximum value. Since the first liquid is discharged from the outlet end 112 of the liquid discharging nozzle 110 at the constant flow rate, at the moment the droplet 195 is detached from the outlet end 112 of the liquid discharging nozzle 110, a new droplet 195 enters a generation state. When the outlet end 112 of the liquid discharging nozzle 110 accelerates again in the opposite direction, the newly generated droplet 195 drops from the outlet end 112 of the liquid discharging nozzle 110, forming a new microdroplet 199.

In this embodiment, two microdroplets 199 can be generated in one motion period of the outlet end 112 of the liquid discharging nozzle 110, and the square wave can easily be achieved in practice. In another embodiment, one microdroplet 199 is generated in one motion period of the outlet end 112 of the liquid discharging nozzle 110. Optionally, in an embodiment, the outlet end 112 of the liquid discharging nozzle 110 moves along a straight line trajectory in any direction at a speed varying in a square wave form in the second liquid 699, for example, the outlet end moves along a straight line trajectory at a speed varying in the square wave form in a plane perpendicular to an extending direction of the liquid discharging nozzle 110, or along a straight line trajectory at a speed varying in the square wave form in any plane angularly disposed relative to the extending direction of the liquid discharging nozzle 110, or along a straight line trajectory at a speed varying in the square wave form in the extending direction of the liquid discharging nozzle 110, etc. In other embodiments of the present application, when the moving trajectory of the outlet end 112 of the liquid discharging nozzle 110 is an arc or a polygon, the outlet end 112 of the liquid discharging nozzle 110 moves along an arc-shaped trajectory or a polygonal trajectory at a speed varying in a square wave form in any direction in the second liquid 699, for example, the outlet end moves along an arc-shaped trajectory or a polygonal trajectory at a speed varying in the square wave form in a plane perpendicular to the extending direction of the liquid discharging nozzle 110, or along an arc-shaped trajectory or a polygonal trajectory at a speed varying in the square wave form in any plane angularly disposed relative to the extending direction of the liquid discharging nozzle 110, or along an arc-shaped trajectory or a polygonal trajectory at a speed varying in the square wave form in the extending direction of the liquid discharging nozzle 110, etc.

Figure 6:
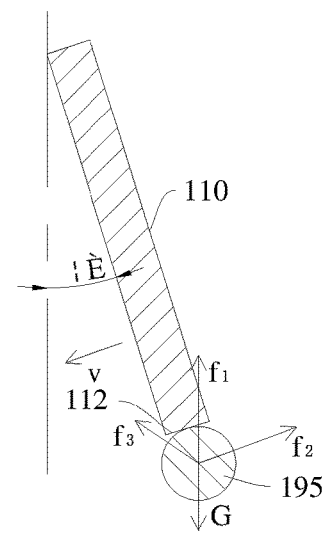
FIG. 6 is a schematic view of forces exerted on a droplet when the outlet end of the liquid discharging nozzle moves according to another embodiment of the present application.

In an embodiment of the present application, driven by the motion controlling mechanism 130, the outlet end 112 of the liquid discharging nozzle 110 moves at a periodically changed speed blow the liquid surface of the second liquid. The speed of the outlet end 112 of the liquid discharging nozzle 110 changes monotonously in both the first half period and the second half period of the speed variation. The monotonously changing means that the speed of the outlet end 112 of the liquid discharging nozzle 110 at a subsequent moment is always greater than or equal to (or, less than or equal to) the speed at a previous moment in the first half period or the second half period the speed variation. For example, during the first half period of the speed variation, the speed of the outlet end 112 of the liquid discharging nozzle 110 continuously increases, or the speed continuously increases in some time periods and remains unchanged in some other time periods. Correspondingly, during the second half period of the speed variation, the speed of the outlet end 112 of the liquid discharging nozzle 110 continuously decreases, or the speed continuously decreases in some time periods and remains unchanged in some other time periods. The first liquid discharged from the outlet end 112 of the liquid discharging nozzle 110 is formed into a droplet 195 attached to the outlet end 112 of the liquid discharging nozzle 110. The droplet 195 is detached from the outlet end 112 of the liquid discharging nozzle 110, and the microdroplet 199 is formed at the moment the moving speed of the outlet end 112 of the liquid discharging nozzle 110 reaches a set value. Referring to FIG. 6, the forces exerted upon the microdroplet 199, before the microdroplet 199 is detached from the outlet end 112 of the liquid discharging nozzle 110, are respectively the gravity G, a buoyancy $f_1$ from the second liquid 699, a viscous resistance force $f_2$ from the second liquid 699, and a maximum adhesion force $f_3$ between the outlet end 112 of the liquid discharging nozzle 110 and the droplet 195. The microdroplet 199 has a mass m, a speed v, and an acceleration $a_2$ before being detached from the outlet end 112 of the liquid discharging nozzle 110. During moving in the second liquid 699, the droplet 195 is under a combined action of the viscous force $f_2$, the gravity G, the buoyancy $f_1$, and the adhesion force $f_3$, namely $m\vec{a}_2=\vec{f}_1+\vec{G}+\vec{f}_2+\vec{f}_3$. The condition for detaching the droplet 195 from the outlet end 112 of the liquid discharging nozzle 110 (i.e., for generating one microdroplet 199) is $|\vec{f}_3|<|\vec{f}_1+\vec{G}+\vec{f}_2-m\vec{a}_2|$.

The maximum value $f_3$ of the adhesion force between the outlet end 112 of the liquid discharging nozzle 110 and the droplet 195 is related to the surface free energy of the liquid discharging nozzle 110, the surface tension of the droplet 195, and the geometric dimension of the liquid discharging nozzle 110. The droplet 195 attached to the outlet end 112 of the liquid discharging nozzle 110 is simplified as a sphere. According to the Stokes formula, the viscous resistance force $f_2$ applied on the droplet 195 moving in the second liquid 699 satisfies $f_2=6\pi\eta rv$, wherein η denotes a viscous coefficient of the second liquid 699, r denotes a radius of the droplet 195, and v denotes a moving speed of the droplet 195. In the process of generating the microdroplet 199, a volume of droplet 195 is generally in a range from picoliter magnitude order to microliter magnitude order, and the viscosity coefficient of the second liquid 699 is commonly relatively large. Therefore, generally, $|\vec{f}_2|\gg|\vec{G}|$, $|\vec{f}_2|\gg|\vec{f}_1|$ and $|\vec{f}_2|\gg|m\vec{a}_2|$. Therefore, when the outlet end 112 of the liquid discharging nozzle 110 periodically moves at a changing velocity below the liquid surface of second liquid 699, the condition for detaching the droplet 195 from the outlet end 112 of the liquid discharging nozzle 110 (i.e., for generating one microdroplet 199) is approximately $|\vec{f}_3|<|\vec{f}_2|$.

Based on this, the present application provides a microdroplet generating method, including the following steps:

S211, providing the liquid discharging nozzle 110 having the outlet end 112, wherein the first liquid is stored in the liquid discharging nozzle 110; providing a microdroplet container 60 containing the second liquid 699 therein, the microdroplet container 60 having an opening; wherein the first liquid and the second liquid 699 are any two immiscible liquids or any two liquids having an interfacial reaction therebetween;

S212, inserting the outlet end 112 of the liquid discharging nozzle 110 below the liquid surface of the second liquid 699 through the opening of the microdroplet container 60;

S213, controlling the outlet end 112 of the liquid discharging nozzle 110 to move at a periodically changed speed below the liquid surface of the second liquid 699, and in the first half period and the second half period of the speed variation, the speed of the outlet end 112 of the liquid discharging nozzle 110 changes monotonously, while the first liquid is discharged at a constant flow rate from the outlet end 112 of the liquid discharging nozzle 110, and the first liquid discharged from the outlet end 112 of the liquid discharging nozzle 110 is formed into the droplet 195 attached to the outlet end 112 of the liquid discharging nozzle 110, then the droplet 195 is detached from the outlet end 112 of the discharging nozzle 110 during the moving of the outlet end 112 of the liquid discharging nozzle 110, thereby forming the microdroplet 199 below the liquid surface of the second liquid 699.

In the microdroplet generating method above, the outlet end 112 of the liquid discharging nozzle 110 makes a motion with a periodically changed speed blow the liquid surface of the second liquid 699. The speed of the outlet end 112 of the liquid discharging nozzle 110 change monotonously in both the first half period and the second half period of the speed variation. During the movement, the viscous force $f_2$ exerted upon the droplet 195 by the second liquid 699 also shows a periodic change in accordance with the periodically changed speed of the outlet end 112 of liquid discharging nozzle 110. When the maximum adhesion force $f_3$ between the outlet end 112 of the liquid discharging nozzle 110 and the droplet 195 is smaller than the viscous force $f_2$ exerted on the droplet 195 by the second liquid 699, the droplet 195 cannot move synchronously with the outlet end 112 of the liquid discharging nozzle 110, so that the droplet 195 attached to the outlet end 112 of the discharging nozzle 110 is detached from the outlet end 112 of the liquid discharging nozzle 110 to form the microdroplet 199 below the liquid surface of the second liquid 699. In the microdroplet generating method provided in the present application, the outlet end 112 of the liquid discharging nozzle 110 makes a periodic motion with a varying velocity below the liquid surface of the second liquid 699 to generate the microdroplet 199, which reduces the disturbance to the second liquid when the outlet end 112 of the liquid discharging nozzle 110 moves, and ensures the stability of the generation of the microdroplet 199.

In this embodiment, in step S213, the first liquid is continuously discharged from the outlet end 112 of the liquid discharging nozzle 110. Further, in step S213, the first liquid is discharged from the outlet end 112 of the liquid discharging nozzle 110 at a constant flow rate, that is, the volumes of the first liquid discharged from the outlet end 112 of the liquid discharging nozzle 110 in equal time intervals are always equal to each other. The discharging of the first liquid at the constant flow rate from the outlet end 112 of the liquid discharging nozzle 110 is beneficial for realizing the controlling of the generation of the microdroplets 199 to have the uniform volume through controlling the periodic motion of the outlet end 112 of the liquid discharging nozzle 110.

Among the factors that affect the viscous resistance force $f_2$ applied on the droplet 195 moving in the second liquid 699, the moving speed v of the droplet 195 can be controlled more easily. The droplet 195 synchronously moves with the outlet end 112 of the liquid discharging nozzle 110 till the droplet 195 is detached from the outlet end 112 of the liquid discharging nozzle 110 to form the microdroplet 199. Therefore, the moving speed v of the droplet 195 can be accurately controlled by controlling the moving speed of the outlet end 112 of the liquid discharging nozzle 110. The first liquid is controlled to be discharged at the uniform flow rate from the outlet end 112 of the liquid discharging nozzle 110, thus the radius r of the droplet 195 also exhibits a periodic change in a set time interval. Among the factors that affect the viscous resistance force $f_2$ applied on the droplet 195 when the droplet 195 moves in the second liquid 699, the viscosity coefficient II of the second liquid 699 will vary within a certain scope in use, but the varying scope of the viscosity coefficient II of the second liquid 699 is very small.

The surface free energy of the liquid discharging nozzle 110, the geometric dimension of the liquid discharging nozzle 110, and the surface tension of the droplet 195, as the factors affecting the maximum adhesion force $f_3$ between the outlet end 112 of the liquid discharging nozzle 110 and the droplet 195, are determined if the liquid discharging nozzle 110 and the first liquid are not changed. Therefore, the maximum value $f_3$ of the adhesion force between the outlet end 112 of the liquid discharging nozzle 110 and the droplet 195 is fixed if the liquid discharging nozzle 110 and the first liquid are not changed. The surface free energy of the liquid discharging nozzle 110 and the geometric dimension of the liquid discharging nozzle 110, as two factors affecting the maximum adhesion force $f_3$ between the outlet end 112 of the liquid discharging nozzle 110 and the droplet 195, are varied if multiple liquid discharging nozzles 110 are used to generate the microdroplets 199 simultaneously or in sequence. However, the variation of the surface free energies of liquid discharging nozzles 110 and the geometric dimensions of the liquid discharging nozzles 110 can be controlled within a certain range via batch processing. The surface tension of the droplet 195, as another factor affecting the maximum adhesion force $f_3$ between the outlet end 112 of the liquid discharging nozzle 110 and the droplet 195, also varies within a very small range. Therefore, the maximum adhesion force $f_3$ between the outlet end 112 of the liquid discharging nozzle 110 and the droplet 195 fluctuates within a very small range.

Therefore, it only needs to control the viscous resistance force $f_2$ applied on the droplet 195 moving in the second liquid 699 to be greater than the range of the maximum adhesion force value $f_3$ between the outlet end 112 of the liquid discharging nozzle 110 and the droplet 195. In the generation process of the microdroplets 199 of the same batch, the droplets 195 should have same radius r. Once the experimental parameters are determined, the radius r of the droplet 195 is also determined accordingly. The outlet end 112 of the liquid discharging nozzle 110 moves at the varying speed below the liquid surface of the second liquid 699. When the moving speed of the outlet end 112 of the liquid discharging nozzle 110 below the liquid surface of the second liquid 699 satisfies $v > f_3/6\pi\eta r$, the droplet 195 is detached from the outlet end 112 of the liquid discharging nozzle 110 to form the microdroplet 199.

The outlet end 112 of the liquid discharging nozzle 110 moves at the periodically changed speed below the liquid surface of the second liquid 699. By controlling the first liquid to be discharged from the outlet end 112 of the liquid discharging nozzle 110 at the uniform flow rate, the volume of the droplet 195 attached to the outlet end 112 of the liquid discharging nozzle 110 also uniformly increases. At the moment the microdroplet 199 is detached from the outlet end 112 of the liquid discharging nozzle 110, the radius of the microdroplet 199 is called the critical radius, and the speed of the microdroplet 199 is called the critical speed. The motion period of the outlet end 112 of the liquid discharging nozzle 110 and the flow rate, at which the first liquid is discharged from the outlet end 112 of the liquid discharge nozzle 110, are adjusted to allow the droplets 195 attached to the outlet end 112 of the liquid discharging nozzle 110 reach the critical radius and the critical speed after equal time intervals (in multiple motion periods of the outlet end 112 of the liquid discharging nozzle 110), thus forming the new microdroplets 199. Since the first liquid is discharged from the outlet end 112 of the liquid discharging nozzle 110 at the uniform flow rate, the volume values of the generated microdroplets 199 are identical.

As an implementation manner, in step S213, the speed of the outlet end 112 of the liquid discharging nozzle 110 is center symmetrical relative to the midpoint which is the middle time point of the period of the speed variation. Further, in step S213, the acceleration, the velocity, and the moving trajectory of the outlet end 112 of the liquid discharging nozzle 110 below the liquid surface of the second liquid 699 are periodically changed. Furthermore, in step S213, the speed of the outlet end 112 of the liquid discharging nozzle 110 below the liquid surface of the second liquid 699 varies in a form of a cosine curve.

Optionally, in step S213, the moving trajectory of the outlet end 112 of the liquid discharging nozzle 110 below the liquid surface of the second liquid 699 includes one of or a combination of various trajectories such as a straight line segment, an arc-shaped line segment, or a polygon. In step S213, the frequency of the periodic motion of the outlet end 112 of the liquid discharging nozzle 110 below the liquid surface of the second liquid 699 is between 0.1 Hz and 200 Hz, which can easily be realized in practice.

Figure 7:
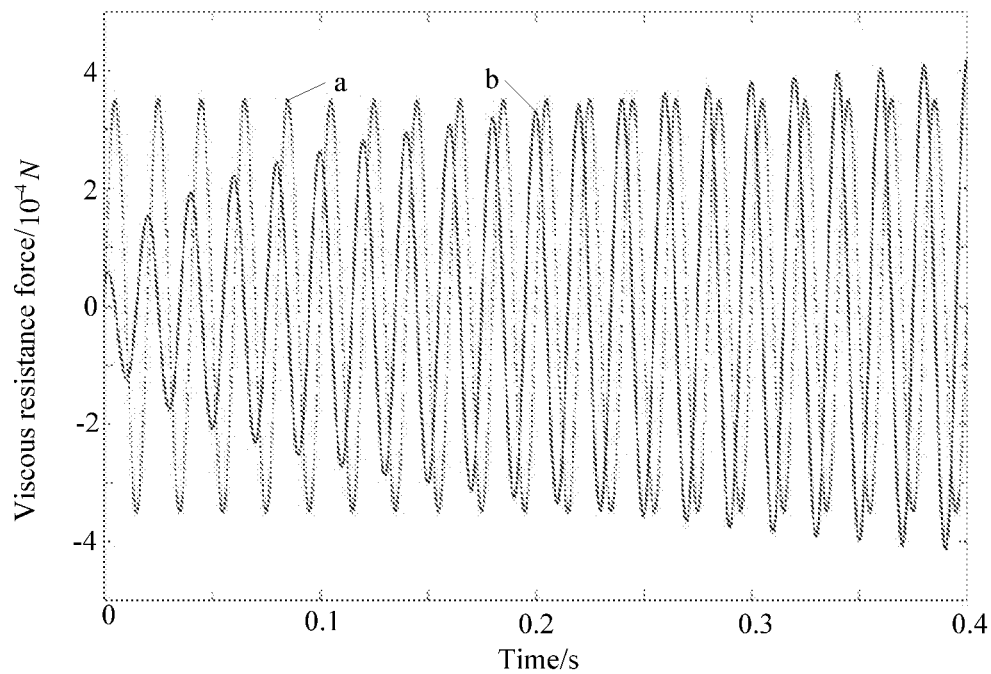
FIG. 7 is a schematic view of an ideal change of viscosity resistance force exerted on a droplet moving with the outlet end of the liquid discharging nozzle provided by an embodiment of the present application.

Taking the periodic motion of the outlet end 112 of the liquid discharging nozzle 110 below the liquid surface of the second liquid 699 as an example, the periodic motion has an arc trajectory with a speed changing in the cosine form, and the outlet end 112 of the liquid discharging nozzle 110 actually makes a swing motion with a displacement that can be represented by a sine curve as the curve a shown in FIG. 7. Driven by the liquid driving mechanism, the first liquid is discharged from the outlet end 112 of the liquid discharging nozzle 110 at a uniform flow rate. Assuming that the droplet 195 is not detached from the outlet end 112 of the liquid discharging nozzle 110, the viscosity resistance force $f_2$, changing with time and applied on the droplet 195 moving in the second liquid 699, is represented by the curve b in FIG. 7 obtained through calculation. At an initial stage of the discharge of the first liquid from the outlet end 112 of the liquid discharging nozzle 110 at the uniform flow rate, the radius r of the droplet 195 significantly increases with the volume increase of the droplet 195. As the radius r of the droplet 195 continues to increase, the uniform volume increase of the droplet 195 will only result in a slow increase of the radius r of the droplet 195. Therefore, the maximum viscous resistance force $f_2$ applied on the droplet 195 moving in the second liquid 699 increases rapidly at first and then the increase gradually slows down during the first few swing periods of the outlet end 112 of the liquid discharging nozzle 110. As shown in FIG. 7, the viscous resistance force $f_2$ applied on the droplet 195 moving in the second liquid 699 also shows a periodic feature similar to the periodic motion of the outlet end 112 of the liquid discharging nozzle 110; that is, the viscous resistance force $f_2$ applied on the droplet 195 moving in the second liquid 699 varies with the speed of the outlet end 112 of the liquid discharging nozzle 110. In the actual working condition, the droplet 195 is detached from the outlet end 112 of the liquid discharging nozzle 110 at the moment the viscosity resistance force $f_2$ applied on the droplet 195 moving in the second liquid 699 increases to the value greater than the maximum adhesion force $f_3$ between the outlet end 112 of the liquid discharging nozzle 110 and the droplet 195, forming the microdroplet 199.

Figure 8:
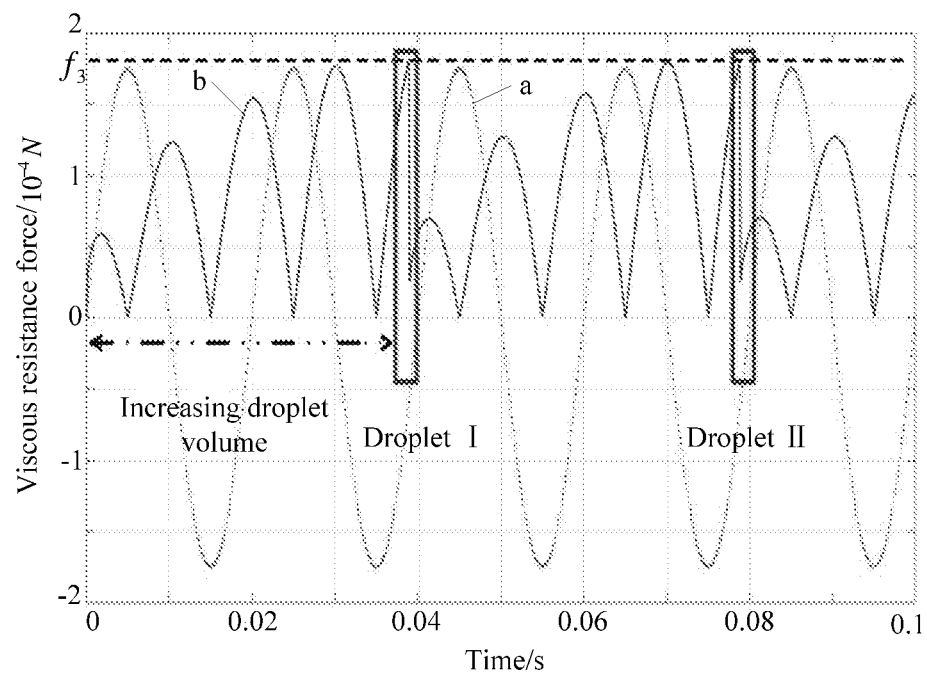
FIG. 8 is a schematic view illustrating a process of generating one microdroplet in every two motion periods of the outlet end of the liquid discharging nozzle provided by an embodiment of the present application.

In an embodiment of the present application, referring to FIG. 8, the outlet end 112 of the liquid discharging nozzle 110 is controlled to swing along a circular arc trajectory with a displacement changing in a sine form. In a case that the liquid discharging nozzle 110 and the first liquid are not changed, the maximum value $f_3$ of the adhesion force between the outlet end 112 of the liquid discharging nozzle 110 and the droplet 195 is fixed. The viscous resistance force $f_2$ applied on the droplet 195 moving in the second liquid 699 continuously increases with the increase of the radius r of the droplet 195 attached to the outlet end 112 of the liquid discharging nozzle 110. At the moment the viscous resistance force $f_2$ applied on the droplet 195 moving in the second liquid 699 is greater than the maximum adhesion force $f_3$ between the outlet end 112 of the liquid discharging nozzle 110 and the droplet 195, the droplet 195 is detached from the outlet end 112 of the liquid discharging nozzle 110 and forms the microdroplet 199 which is the droplet I in FIG. 8. Then the next generation cycle of the microdroplet 199 begins.

In this embodiment, the maximum adhesion force $f_3$ between the outlet end 112 of the liquid discharging nozzle 110 and the droplet 195 is $f_3=1.8\times10^{-4}$ N, and the swing frequency of the outlet end 112 of the liquid discharging nozzle 110 is 50 Hz. The first microdroplet 199 (the droplet I in FIG. 8) is generated at the end of the second period of the swing motion of the outlet end 112 of the liquid discharging nozzle 110 whose displacement changes in a sine form. In the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 decreases at this stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110.

The first liquid is controlled to be discharged from the outlet end 112 of the liquid discharging nozzle 110 at the uniform flow rate, so that a new droplet 195 (the droplet II in FIG. 8) having the volume equal to that of the previous microdroplet 199 is generated again at the outlet end 112 of the liquid discharging nozzle 110 at the moment two motion periods passed right after the generation of the previous microdroplet 199. Moreover, the moving speed of the outlet end 112 of the liquid discharging nozzle 110 at this moment is also the same as that two motion periods ago. The new droplet 195 having the same volume as the previous microdroplet 199 is detached from the outlet end 112 of the liquid discharging nozzle 110. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form.

Figure 9:
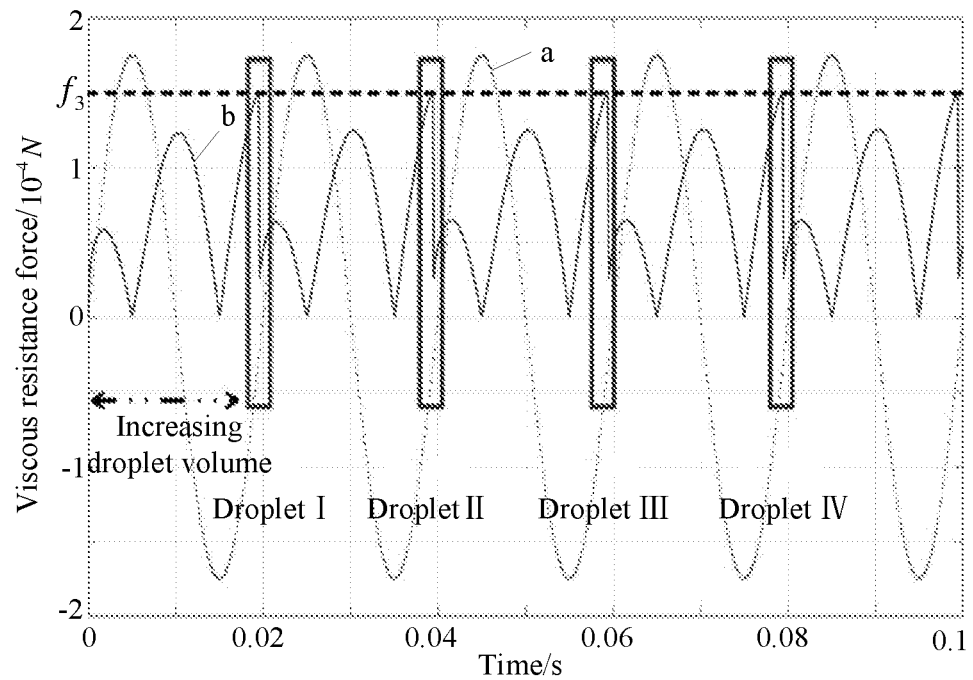
FIG. 9 is a schematic view illustrating a process of generating one microdroplet in each motion period of the outlet end of the liquid discharging nozzle provided by an embodiment of the present application.

In an embodiment of the present application, referring to FIG. 9, the outlet end 112 of the liquid discharging nozzle 110 is controlled to swing along a circular arc trajectory with a displacement changing in a sine form. In a case that the liquid discharging nozzle 110 and the first liquid are not changed, the maximum adhesion force $f_3$ of the between the outlet end 112 of the liquid discharging nozzle 110 and the droplet 195 is fixed. The viscous resistance force $f_2$ applied on the droplet 195 moving in the second liquid 699 continuously increases with the increase of the radius r of the droplet 195 attached to the outlet end 112 of the liquid discharging nozzle 110. At the moment the viscous resistance force $f_2$ applied on the droplet 195 moving in the second liquid 699 is greater than the maximum adhesion force $f_3$ between the outlet end 112 of the liquid discharging nozzle 110 and the droplet 195, the droplet 195 is detached from the outlet end 112 of the liquid discharging nozzle 110 and forms the microdroplet 199. Then the next generation cycle of the microdroplet 199 begins.

In this embodiment, the maximum adhesion force $f_3$ between the outlet end 112 of the liquid discharging nozzle 110 and the droplet 195 is $f_3=1.5\times10^{-4}$ N, and the swing frequency of the outlet end 112 of the liquid discharging nozzle 110 is 50 Hz. The first microdroplet 199, the droplet I in FIG. 9, is generated at the end of the first period of the swing motion of the outlet end 112 of the liquid discharging nozzle 110 whose displacement changes in a sine form. In the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 decreases at this stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110.

The first liquid is controlled to be discharged from the outlet end 112 of the liquid discharging nozzle 110 at the uniform flow rate, so that a new droplet 195 having the volume equal to that of the previous microdroplet 199 is generated again at the outlet end 112 of the liquid discharging nozzle 110 at the moment one motion period passed right after the generation of the previous microdroplet 199. Moreover, the moving speed of the outlet end 112 of the liquid discharging nozzle 110 at this moment is also the same as that one motion period ago. The new droplet 195, the droplet II in FIG. 9, having the same volume as that of the previous microdroplet 199 and is detached from the outlet end 112 of the liquid discharging nozzle 110. By cycling like this, the droplet III, droplet IV, and so on are generated. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form.

Figure 10:
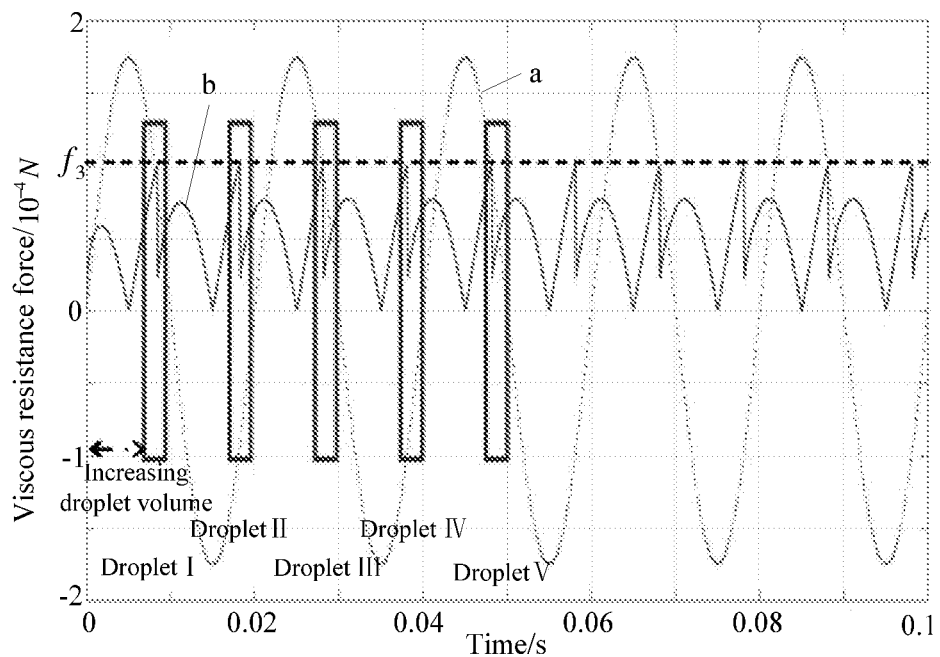
FIG. 10 is a schematic view illustrating a process of generating two microdroplets in each motion period of the outlet end of the liquid discharging nozzle provided by an embodiment of the present application.
Figure 11:
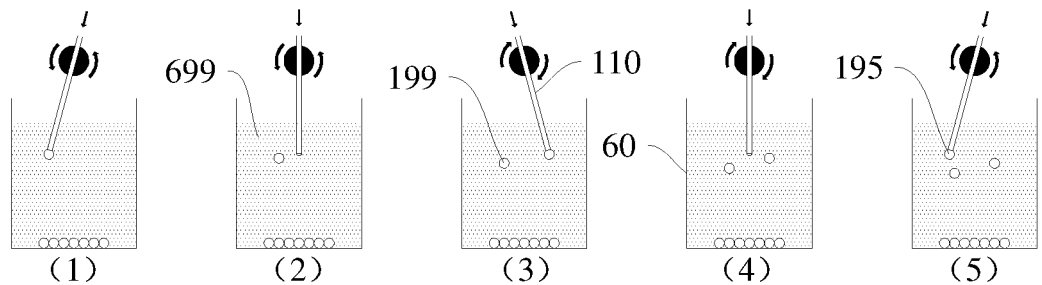
FIG. 11 is a schematic view illustrating generation processes of microdroplets when the outlet end of the liquid discharging nozzle swings according to an embodiment of the present application.

In an embodiment of the present application, referring to FIG. 10 and FIG. 11, the outlet end 112 of the liquid discharging nozzle 110 is controlled to swing along a circular arc trajectory with a displacement changing in a sine form. In a case that the liquid discharging nozzle 110 and the first liquid are not changed, the maximum adhesion force $f_3$ between the outlet end 112 of the liquid discharging nozzle 110 and the droplet 195 is fixed. The viscous resistance force $f_2$ applied on the droplet 195 moving in the second liquid 699 continuously increases with the increase of the radius r of the droplet 195 attached to the outlet end 112 of the liquid discharging nozzle 110. At the moment the viscous resistance force $f_2$ applied on the droplet 195 moving in the second liquid 699 is greater than the maximum adhesion force $f_3$ between the outlet end 112 of the liquid discharging nozzle 110 and the droplet 195, the droplet 195 is detached from the outlet end 112 of the liquid discharging nozzle 110 and forms the microdroplet 199 (the droplet I in FIG. 10). Then the next generation cycle of the microdroplet 199 begins.

In this embodiment, the maximum adhesion force $f_3$ between the outlet end 112 of the liquid discharging nozzle 110 and the droplet 195 is $f_3=1.0\times10^{-4}$ N, and the swing frequency of the outlet end 112 of the liquid discharging nozzle 110 is 50 Hz. The first microdroplet 199 (the droplet I in FIG. 10) is generated at the accelerating stage of the first half period of the swing motion of the outlet end 112 of the liquid discharging nozzle 110 whose displacement changes in a sine form. In the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 decreases at this stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110.

The first liquid is controlled to be discharged from the outlet end 112 of the liquid discharging nozzle 110 at the uniform flow rate. The second microdroplet 199, the droplet II in FIG. 10, is generated at the accelerating stage of the second half period of the swing motion of the outlet end 112 of the liquid discharging nozzle 110 having the displacement changing in the sine form. After that is the stable generation stage of the microdroplet 199.

A new droplet 195 having the volume equal to that of the second microdroplet 199 is generated again at the outlet end 112 of the liquid discharging nozzle 110 at the moment half a motion period passed right after the generation of the second microdroplet 199. Moreover, the moving speed of the outlet end 112 of the liquid discharging nozzle 110 at this moment is also the same as that half a motion period ago. The new droplet 195 having the same volume as that of the second microdroplet 199 is detached from the outlet end 112 of the liquid discharging nozzle 110. By cycling like this, the droplet III, droplet IV, droplet V, and so on in FIG. 10 are generated. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form.

As described above, the condition for detaching the droplet 195 from the outlet end 112 of the liquid discharging nozzle 110 (i.e. for generating one microdroplet 199) is roughly $|f_3|<|f_2|$. On the condition that the first liquid is discharged at the uniform flow rate from the outlet end 112 of the liquid discharging nozzle 110, the condition for generating the uniform-sized microdroplets 199 is that: the microdroplets 199 are detached from the outlet end 112 of the liquid discharging nozzle 110 at the equal time intervals.

Figure 12:
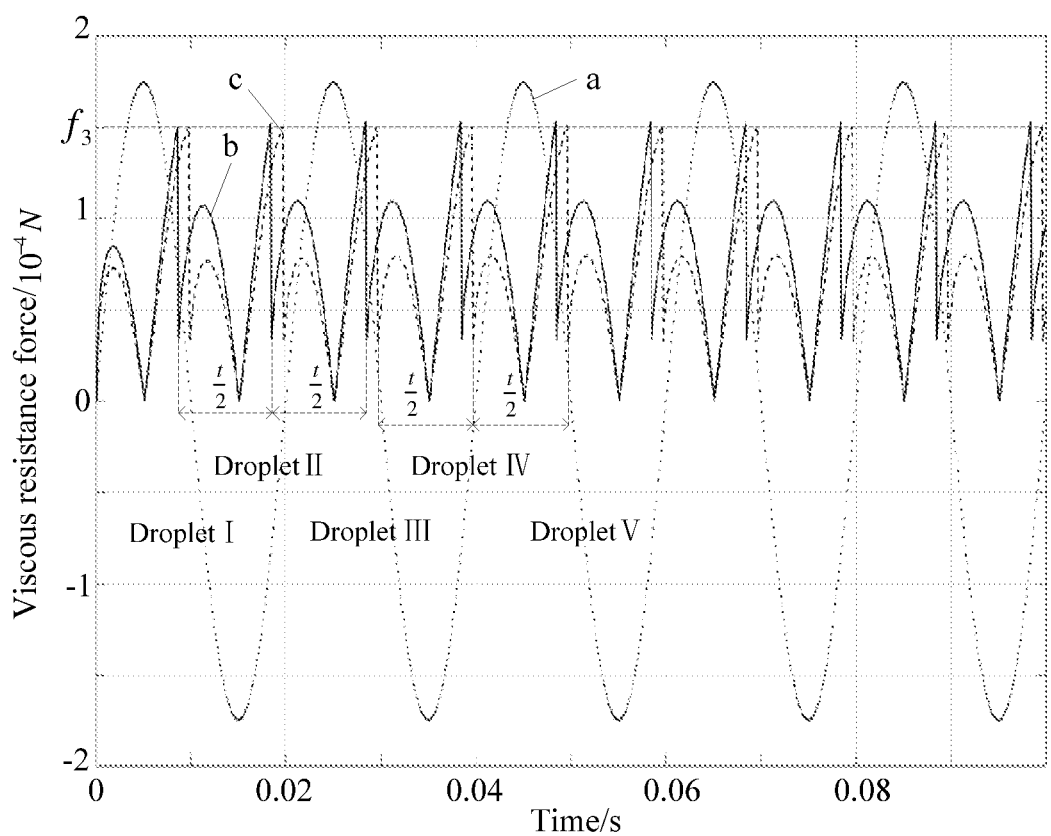
FIG. 12 is a schematic view illustrating generation processes of microdroplets when viscosity of a second liquid varies according to an embodiment of the present application.

The factors affecting the maximum adhesion force $f_3$ between the outlet end 112 of the liquid discharging nozzle 110 and the droplet 195 includes the surface free energy of the liquid discharging nozzle 110, the geometric dimension of the liquid discharging nozzle 110, and the surface tension of the first liquid. Therefore, the maximum the adhesion force $f_3$ between the outlet end 112 of the liquid discharging nozzle 110 and the droplet 195 is fixed in the case that the liquid discharging nozzle 110 and the first liquid are not changed. The factors affecting the viscous resistance force $f_2$ exerted upon the droplet 195 moving in the second liquid 699 includes the viscous coefficient II of the second liquid 699, the radius r of the droplet 195, and the moving speed v of the droplet 195. The radius r of the droplet 195 is decided by the time interval between the generating of the microdroplets 199. The droplet 195 moves synchronously with the outlet end 112 of the liquid discharging nozzle 110 before it is detached from the outlet end 112 of the liquid discharging nozzle 110. The moving speed of the outlet end 112 of the liquid discharging nozzle 110 can be accurately controlled by the motion controlling mechanism 130. The viscosity coefficient II of the second liquid 699 will change within a certain range during the generation of the droplet 195, but this variation range of the viscosity coefficient II of the second liquid 699 is very small. Referring to FIG. 12, the curve a represents the displacement change of the outlet end 112 of the liquid discharging nozzle 110, and the curve b and the curve c are the generation process curves of the microdroplets 199 when the viscosity coefficient II of the second liquid 699 changes within the small range. The moment, at which the microdroplet 199 is generated, is changed only within a fairy small range, and the time interval between the generating of the microdroplets 199 will not change, if the viscosity coefficient II of the second liquid 699 changes within a very small range. As shown in FIG. 12, the time intervals between the generations of the microdroplets 199 represented by the curve b and the curve c each are half a period t/2, ensuring the uniformity of the volume of the generated microdroplets 199.

Figure 13:
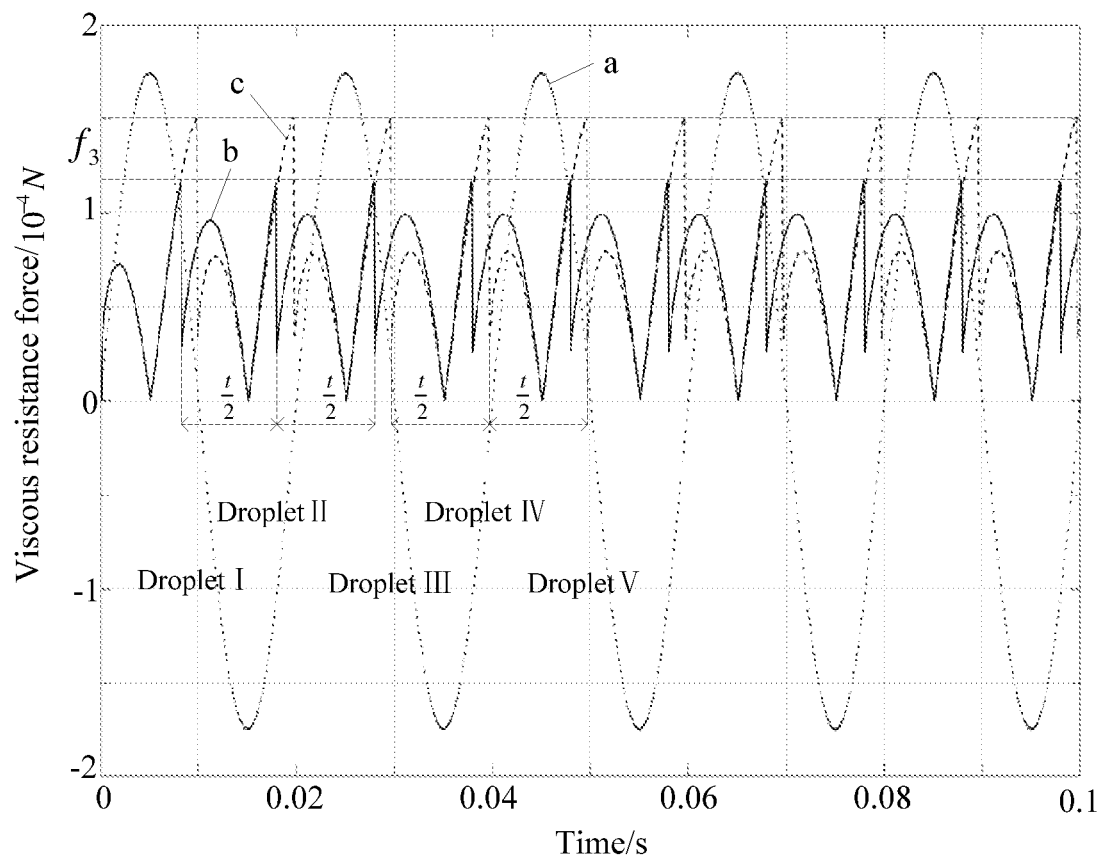
FIG. 13 is a schematic view illustrating generation processes of microdroplets when liquid discharging nozzle is replaced according to an embodiment of the present application.

Referring to FIG. 13, on the condition that the liquid discharging nozzle 110 is replaced, or the surface tension of the first liquid changes due to change of temperature, it is difficult to accurately control the maximum adhesion force $f_3$ between the outlet end 112 of the liquid discharging nozzle 110 and the droplet 195. Therefore, the volume of the generated microdroplet 199 being not sensitive to the change of $f_3$ within a certain range is of great significance for generating the uniform-sized microdroplets 199. In FIG. 13, the curve a represents the displacement change of the outlet end 112 of the liquid discharging nozzle 110, and the curve b and the curve c are the generation process curves of the microdroplets 199 in a case that the liquid discharging nozzles 110 is replaced. By replacing the liquid discharging nozzle 110, the maximum adhesion force $f_3$ between the outlet end 112 of the liquid discharging nozzle 110 and the droplet 195 fluctuates within a certain range, which induces that the outlet ends 112 of the liquid discharging nozzles 110 have different speeds when the droplets 195 are detached. Whereas, when the generations of the microdroplets 199 enter the stable state, the speed of the outlet end 112 of the liquid discharging nozzle 110 becomes a fixed value when the droplets 195 are detached in each swing period. As shown in FIG. 13, the time intervals between the generations of the microdroplets 199 represented by the curve band the curve c each are half a period t/2. Therefore, the fixed time interval between the generations of the microdroplets 199 can be ensured. Moreover, the flow rate of the first liquid discharged from the outlet end 112 of the liquid discharging nozzle 110 is fixed. Therefore, the generated microdroplets 199 have the uniform volume. The volume and the generation rate of the uniform-volume microdroplets 199 can be simultaneously controlled by adjusting both the flow rate of the first liquid discharging from the outlet end 112 of the liquid discharging nozzle 110 and the swing frequency of the outlet end 112 of the liquid discharging nozzle 110 in the second liquid 699.

In the above embodiment, there is a tolerance at a certain degree for the changes of the maximum adhesion force $f_3$ and the viscous resistance force $f_2$ when the outlet end 112 of the liquid discharging nozzle 110 periodically moves with a displacement changing in a sine form. That is to say, the microdroplets 199 with the uniform volume can still be generated when the maximum adhesion force $f_3$ and the viscous resistance force $f_2$ change within a certain range. When the outlet end 112 of the liquid discharging nozzle 110 periodically moves with the displacement changing in a sine form, on the condition that the uniform volume of the microdroplets 199 is guaranteed, the tolerance range for the maximum adhesion force $f_3$ is called a "platform stage". The platform stage is of great significance for the processing of the liquid discharging nozzle 110 and the controlling of the temperature of generating the microdroplets 199. The existence of the platform stage allows the requirement for the processing accuracy of the liquid discharging nozzle 110 to be reduced to a certain extent. That is to say, the microdroplets 199 with the uniform volume can still be generated even if there is a difference in the surface free energy between the liquid discharging nozzles 110 of the same batch. Similarly, the existence of the platform stage also allows the requirement for the controlling of the temperature of generating the microdroplets 199 to be reduced to a certain extent.

The cost of consumables and the cost of controlling the generation of the microdroplets 199 can be further reduced as the existence of the platform stage allows the requirement for the processing accuracy of the liquid discharging nozzle 110 or for the controlling of the temperature of generating the microdroplets 199 to be reduced to a certain extent. In the above-described embodiment, two microdroplets 199 are generated in every motion period of the outlet end 112 of the liquid discharging nozzle 110. It will be readily understood that, as long as the outlet end 112 of the liquid discharging nozzle 110 periodically moves with the displacement changing in the sine form, the platform stage and the tolerance at a certain degree for the changes of the maximum adhesion force $f_3$ and the viscous resistance force $f_2$ also exist, on the condition that one microdroplet 199 is generated in every motion period or in every two motion periods of the outlet end 112 of the liquid discharging nozzle 110.

For the reason that the microdroplet 199 is barely affected by the gravity and the inertial force, the outlet end 112 of the liquid discharging nozzle 110 can periodically move with the displacement changing in the sine form in an arbitrary direction in the second liquid 699 during the generation of the microdroplets. The moving trajectory of the outlet end 112 of the liquid discharging nozzle 110 can be an arc, a straight line, or any trajectory with another shape.

Figure 14:
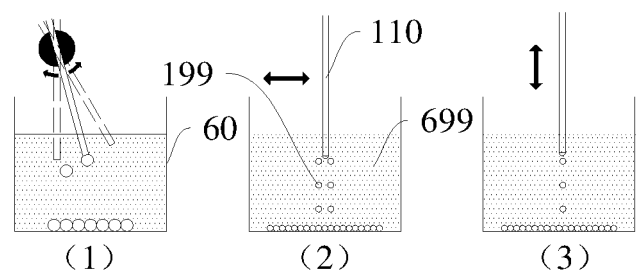
FIG. 14 is a schematic view illustrating generation processes of microdroplets when an outlet end of a liquid discharging nozzle moves along different trajectories according to an embodiment of the present application.

Referring to (1) in FIG. 14, in an embodiment of the present application, the liquid discharging nozzle 110 is inclinedly inserted into the second liquid 699, and the outlet end 112 of the liquid discharging nozzle 110 swings below the liquid surface of the second liquid 699 to generate the microdroplets 199. As an implementation manner, referring to (2) in FIG. 14, the outlet end 112 of the liquid discharging nozzle 110 periodically moves along a trajectory of a horizontal straight line with a displacement changing in the sine form in the second liquid 699 to generate the microdroplets 199. As another implementation manner, referring to (3) in FIG. 14, the outlet end 112 of the liquid discharging nozzle 110 periodically moves along a trajectory of a vertical straight line with a displacement changing in the sine form in the second liquid 699 to generate the microdroplets 199.

Figure 15:
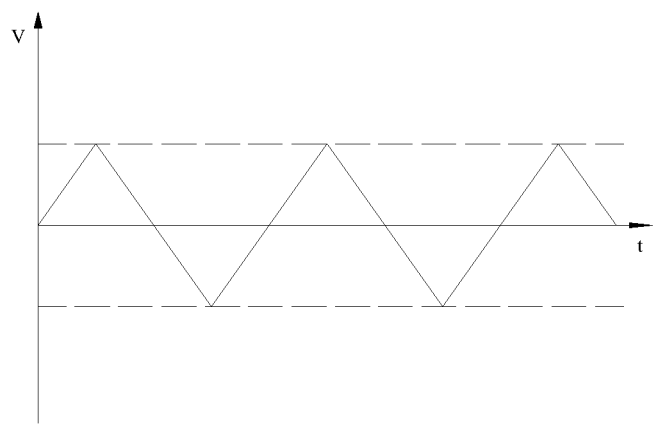
FIG. 15 is a schematic view of a varying speed of the outlet end of the liquid discharging nozzle provided by another embodiment of the present application.

Referring to FIG. 15, in step S213 of another embodiment of the present application, the outlet end 112 of the liquid discharging nozzle 110 moves with a uniform acceleration in both the first half period and the second half period of one speed variation period. Further, in step S213, The magnitudes of the accelerations of the outlet end 112 of the liquid discharging nozzle 110 in the first half period and the second half period are identical. The first liquid is controlled to be discharged from the outlet end 112 of the liquid discharging nozzle 110 at the uniform flow rate. The viscous resistance force $f_2$ applied on the droplet 195 attached to the moving outlet end 112 of the liquid discharging nozzle 110 continuously increases with the continuous discharge of the first liquid. When the viscous resistance force $f_2$ is greater than the maximum adhesion force $f_3$ between the liquid discharging nozzle 110 and the droplet 195, the droplet 195 is detached from the liquid discharging nozzle 110 to form the microdroplet 199. Then, the generation process of the next microdroplet 199 begins. The volume uniformity of the generated microdroplets 199 is ensured by controlling the frequency and speed of motion of the outlet end 112 of the liquid discharging nozzle 110 to be adaptable for the flow rate of the first liquid.

The conventional liquid discharging nozzle is generally in a shape of straight tube. If the straight tubular liquid discharging nozzle moves rapidly in its extension direction to an end proximate to the outlet end, the generated microdroplet would be broken. Therefore, the vibrational frequency of the liquid discharging nozzle has to be decreased to maintain the integrality of the generated microdroplet, thus causing a decrease in the generation rate of the microdroplets.

In view of the problem that the integrality of the generated microdroplet and the generation rate of the microdroplets cannot be well balanced by means of the conventional liquid discharging nozzle, a liquid discharging nozzle capable of well balancing the integrality of the generated microdroplet and the generation rate of the microdroplets is provided.

A liquid discharging nozzle 110 for generating a microdroplet 199 is provided in an embodiment of the present application. The liquid discharging nozzle includes a needle stem 113 having a hollow chamber and an outlet end 112 located at one end of the needle stem 113. An angle between a normal line of an end surface of the outlet end 112 of the liquid discharging nozzle 110 and an extension direction of the needle stem 113 is equal to or smaller than 90°. When the liquid discharging nozzle 110 vibrates in an extension direction of the tube body, under the action of a viscous force from a second liquid 699 and a press from the end surface of the outlet end 112 of the liquid discharging nozzle 110, the microdroplet 199 is detached from the outlet end 112 of the liquid discharging nozzle 110 and then moves away from a moving trajectory of the outlet end 112, thereby preventing the microdroplet 199 from being broken the outlet end 112, thus maintaining the integrality of the generated microdroplet 199, and allowing the liquid discharging nozzle 110 to rapidly vibrate in the extension direction of the tube body, so as to rapidly generate the microdroplet 199.

Figure 16:
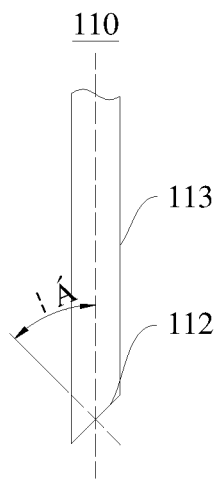
FIG. 16 is a schematic structural view of the outlet end of the liquid discharging nozzle provided by an embodiment of the present application.

Referring to FIG. 16, as an implementation manner, the liquid discharging nozzle 110 is in a shape of straight tube, and the outlet end 112 of the liquid discharging nozzle 110 has a beveled structure. Because of the beveled outlet end 112 of the liquid discharging nozzle 110, not only the integrality of the generated microdroplet 199 and the generation rate of the microdroplets 199 can be well balanced, but also the characteristics of simple structure, easy execution, low manufacturing cost, high accuracy of batch processing can be obtained. Furthermore, the angle between the normal line of the end surface of the outlet end 112 of the liquid discharging nozzle 110 and the extension direction of the needle stem 113 is in a range between 15° and 75°. The angle between the normal line of the end surface of the outlet end 112 of the liquid discharging nozzle 110 and the extension direction of the needle stem 113 can be set according to actual operation conditions. The angle between the normal line of the end surface of the outlet end 112 of the liquid discharging nozzle 110 and the extension direction of the needle stem 113 should not be too large or too small, so as to prevent the generation of the microdroplet 199 from being influenced and the microdroplet 199 from being broken. Yet furthermore, the angle between the normal line of the end surface of the outlet end 112 of the liquid discharging nozzle 110 and the extension direction of the needle stem 113 is in a range between 30° and 60°. Especially, the angle between the normal line of the end surface of the outlet end 112 of the liquid discharging nozzle 110 and the extension direction of the needle stem 113 is 45°, which not only can ensure the smooth generation of the microdroplet 199, but also can effectively detach the generated microdroplet 199 away from the moving trajectory of the outlet end 112, thereby preventing the generated microdroplet 199 from being broken by the outlet end 112 of the liquid discharging nozzle 110.

Figure 17:
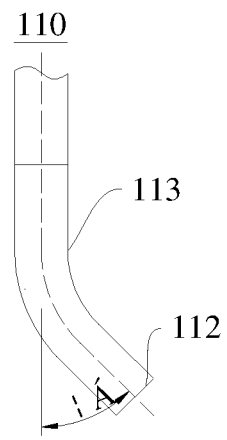
FIG. 17 is a schematic structural view of the outlet end of the liquid discharging nozzle provided by another embodiment of the present application.

Referring to FIG. 17, as another implementation manner, a portion of the needle stem 113, which is proximate to the outlet end 112 of the liquid discharging nozzle 110, has a bent structure. Due to the bent outlet end 112 of the liquid discharging nozzle 110, not only the integrality of the generated microdroplet 199 and the generation rate of the microdroplets 199 can be well balanced, but also the characteristics of simple structure, easy execution, low manufacturing cost, high accuracy of batch processing can be obtained. Furthermore, the angle between the normal line of the end surface of the outlet end 112 of the liquid discharging nozzle 110 and the extension direction of the needle stem 113 is in a range between 15° and 75°. The angle between the normal line of the end surface of the outlet end 112 of the liquid discharging nozzle 110 and the extension direction of the needle stem 113 can be set according to actual operation conditions. The angle between the normal line of the end surface of the outlet end 112 of the liquid discharging nozzle 110 and the extension direction of the needle stem 113 should not be too large or too small, so as to prevent the generation of the microdroplet 199 from being influenced and the microdroplet 199 from being broken. Yet furthermore, the angle between the normal line of the end surface of the outlet end 112 of the liquid discharging nozzle 110 and the extension direction of the needle stem 113 is in a range between 30° and 60°. Especially, the angle between the normal line of the end surface of the outlet end 112 of the liquid discharging nozzle 110 and the extension direction of the needle stem 113 is 45°, which not only can ensure the smooth generation of the microdroplet 199, but also can effectively detach the generated microdroplet 199 away from the moving trajectory of the outlet end 112, thereby prevent the outlet end 112 of the liquid discharging nozzle 110 from breaking the generated microdroplet 199.

Optionally, the bent structure of the needle stem 113, which is proximate to the outlet end 112 of the liquid discharging nozzle 110, is one of or any combination of a bent line section, an arched section, a smooth curved section, a straight line section, and so on. Referring to FIG. 17, in this embodiment, the portion of the needle stem 113, which is proximate to the outlet end 112 of the liquid discharging nozzle 110, has an arched transition section, more specifically, a combination of an arched section and a straight line section. In the manufacturing process, a straight tubular liquid discharging nozzle 110 can be bent to have a preset angle, forming the arched section. Therefore, the manufacturing is convenient.

Figure 18:
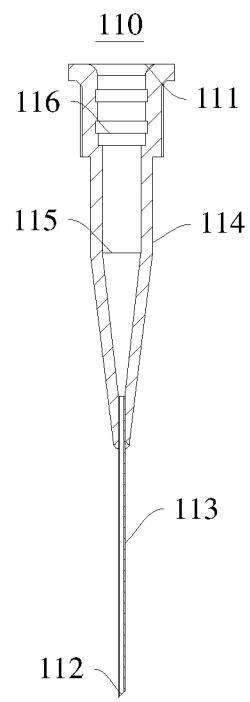
FIG. 18 is a schematic structural view of the liquid discharging nozzle provided by an embodiment of the present application.
Figure 19:
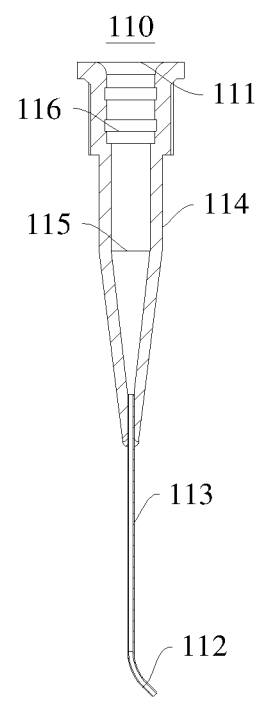
FIG. 19 is a schematic structural view of the liquid discharging nozzle provided by another embodiment of the present application.

Referring to FIGS. 18 and 19, the liquid discharging nozzle 110 in an embodiment of the present application further includes a pintle 114 having a liquid storage cavity 115 passing through the pintle 114 in an extension direction of the pintle 114. One end of the liquid storage cavity 115 communicates with an end of the needle stem 113 away from the outlet end 112 of the liquid discharging nozzle 110. An end of the pintle 114 away from the needle stem 113 is an inlet end 111 of the liquid discharging nozzle 110. The pintle 114 is fixedly connected to the needle stem 113. A first liquid for generating the microdroplet 199 can be previously stored in the pintle 114, so that the microdroplets 199 can be continuously generated in large quantities. Furthermore, a locking groove 116 is defined by an inner surface of the end of the pintle 114 away from the needle stem 113. A detachable connection with a liquid driving mechanism 120 can be achieved via the locking groove 116, so that the liquid discharging nozzle 110 can be replaced conveniently.

A device for generating the microdroplet 199 is further provided in the present application, and configured to generate the microdroplet 199 below a liquid surface of a second liquid 699. The device for generating the microdroplet 199 includes a liquid driving mechanism 120, a motion controlling mechanism 130, and the liquid discharging nozzle 110 provided by any one of the above-described solutions. The liquid discharging nozzle 110 stores the first liquid therein and has the outlet end 112 and the inlet end 111. The liquid driving mechanism 120 is connected to the inlet end 111 of the liquid discharging nozzle 110 and configured to discharge the first liquid stored in the liquid discharging nozzle 110 from the outlet end 112 of the liquid discharging nozzle 110. The motion controlling mechanism 130 is configured to control the outlet end 112 of the liquid discharging nozzle 110 to move along a preset trajectory, or with a preset speed, or with a preset acceleration below the liquid surface of the second liquid 699, so that the first liquid discharged from the outlet end 112 of the liquid discharging nozzle 110 can overcome the surface tension force and the adhesion force to form the micrdroplet 199 in the second liquid 699.

The micrdroplet 199 is generated during the liquid discharging nozzle 110 provided in the present application moving below the liquid surface of the second liquid 699. As an implementation manner, the outlet end 112 of the liquid discharging nozzle 110 moves blow the liquid surface of the second liquid 699 with a speed varying in a form of a square wave, wherein an acceleration value is $a_1$. The first liquid discharged from the outlet end 112 of the liquid discharging nozzle 110 forms a droplet 195 attached to the outlet end 112 of the liquid discharging nozzle 110. The droplet 195 is detached from the outlet end 112 of the liquid discharging nozzle 110 and forms the microdroplet 199 at the moment the outlet end 112 of the liquid discharging nozzle 110 instantaneously accelerates. As shown in FIG. 3, the forces exerted upon the microdroplet 199 before the microdroplet 199 is detached from the outlet end 112 of the liquid discharging nozzle 110 are respectively the gravity G, a buoyancy f from the second liquid 699, a viscous resistance $f_2$ from the second liquid 699, and a maximum adhesion force $f_3$ between the outlet end 112 of the liquid discharging nozzle 110 and the droplet 195. A mass of the microdroplet 199 before the microdroplet is detached from the outlet end 112 of the liquid discharging nozzle 110 is m. The acceleration value of the microdroplet 199 is $a_2$. $m\vec{a}_2 = \vec{G} + \vec{f}_1 + \vec{f}_2 + \vec{f}_3$ is obtained according to Newton's second law of motion.

The maximum adhesion force $f_3$ between the outlet end 112 of the liquid discharging nozzle 110 and the droplet 195 is related to the surface free energy of the liquid discharging nozzle 110, the surface tension force of the droplet 195, and the geometric dimension of the liquid discharging nozzle 110. When the outlet end 112 of the liquid discharging nozzle 110 instantaneously accelerates, a direction of the adhesion force of the outlet end 112 of the liquid discharging nozzle 110 exerted on the droplet 195 is the same as a direction of the acceleration. The droplet 195 attached to the outlet end 112 of the liquid discharging nozzle 110 is simplified as a sphere. According to the Stokes formula, the viscous resistance $f_2$ exerted upon the droplet 195 moving in the second liquid 699 satisfies $f_2=6\pi\eta r v$, wherein $\eta$ denotes a viscous coefficient of the second liquid 699, r denotes a radius of the droplet 195, and v denotes a moving speed of the droplet 195. The speed of the droplet 195 is zero before the outlet end 112 of the liquid discharging nozzle 110 instantaneously accelerates, and thus the viscous resistance $f_2$ exerted upon the droplet 195 by the second liquid is zero or extremely small at the moment the outlet end 112 of the liquid discharging nozzle 110 instantaneously accelerates. In the generation process of the microdroplet 199, a volume of the droplet 195 is generally in a range from the picoliter magnitude order to the microliter magnitude order, and the buoyancy f from the second liquid 699 has a direction opposite to that of the gravity G of the droplet 195; therefore, a vector sum of the buoyancy $f_1$ from the second liquid 699 and the gravity G of the droplet 195 is approximately zero. Therefore, $\vec{G}+\vec{f}_1+\vec{f}_2+\vec{f}_3 \approx \vec{f}_3$. According to the Newton's second law of motion, when the outlet end 112 of the liquid discharging nozzle 110 instantaneously accelerates in motion, the maximum acceleration value achievable by the droplet 195 in the second liquid is $a_2 \approx f_3/m$, wherein m is the mass of the droplet 195. The condition for detaching the droplet 195 from the outlet end 112 of the liquid discharging nozzle 110 (i.e. for generating one microdroplet 199) is roughly $a_2 \approx (f_3/m) < a_1$.

Driven by the motion controlling mechanism 130, the magnitude of the instantaneous acceleration of the outlet end 112 of the liquid discharging nozzle 110 can be accurately controlled. Therefore, the droplets 195 can be effectively generated from the instantaneous accelerated motion of the outlet end 112 of the liquid discharging nozzle 110 by controlling the outlet end 112 of the liquid discharging nozzle 110 to have a relatively large instantaneous acceleration value each time. Optionally, one, two, or more microdroplets 199 are generated in one motion period of the outlet end 112 of the liquid discharging nozzle 110.

Figure 20:
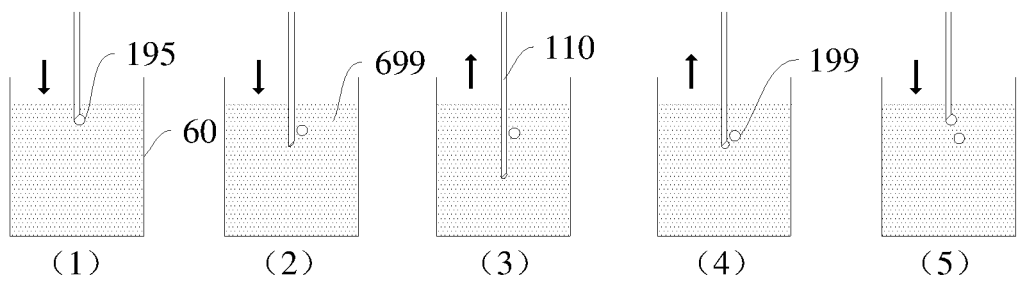
FIG. 20 is a schematic view illustrating a process of generating microdroplets by a liquid discharging nozzle having a beveled cut structure provided by an embodiment of the present application.

As shown in FIG. 20, in an embodiment of the present application, the angle between the normal line of the end surface of the outlet end 112 of the liquid discharging nozzle 110 and the extension direction of the tube body is 45°. The outlet end 112 of the liquid discharging nozzle 110 is a beveled structure. The liquid surface of the second liquid 699 faces upward. The liquid discharging nozzle 110 is disposed vertically. The outlet end 112 of the liquid discharging nozzle 110 is moved below the liquid surface of the second liquid 699 along a vertical linear trajectory with a speed varying in a square wave form. One microdroplet 199 is generated in one motion period of the outlet end 112 of the liquid discharging nozzle 110. The first liquid is stored in the liquid discharging nozzle 110. The liquid driving mechanism 120 controls the liquid discharging nozzle 110 to discharge a same volume of the first liquid in each motion period of the liquid discharging nozzle 110. While the volume of the droplet 195 attached to the outlet end 112 of the liquid discharging nozzle 110 reaches the preset volume, the outlet end 112 of the liquid discharging nozzle 110 instantaneously accelerates downward with the acceleration having a value $a_1$ from an upper limit position, in the meanwhile, the droplet 195 attached to the outlet end 112 of the liquid discharging nozzle 110 is detached from the outlet end 112 of the liquid discharging nozzle 110 to form the microdroplet 199. Under the action of the viscous force of the second liquid 699 and the press of the end surface of the outlet end 112 of the liquid discharging nozzle 110, the microdroplet 199 moves away from the moving trajectory of the outlet end 112 but proximate to a side wall of the liquid discharging nozzle 110. While the outlet end 112 of the liquid discharging nozzle 110 proceeds to move downward, the first liquid is further discharged from the outlet end 112 of the liquid discharging nozzle 110 to form the droplet 195 attached to the outlet end 112 of the liquid discharging nozzle 110. Once the outlet end 112 of the liquid discharging nozzle 110 arrives at a lower limit position, it moves upward from the lower limit position. During the outlet end 112 of the liquid discharging nozzle 110 moving upward from the lower limit position, the first liquid is further discharged from the outlet end 112 of the liquid discharging nozzle 110, and the volume of the droplet 195 attached to the outlet end 112 of the liquid discharging nozzle 110 increases. When the outlet end 112 of the liquid discharging nozzle 110 arrives at the upper limit position, the volume of the droplet 195 attached to the outlet end 112 of the liquid discharging nozzle 110 is the same as that of the microdroplet 199 detached previously, and the outlet end 112 of the liquid discharging nozzle 110 instantaneously accelerates downward with the acceleration having a value $a_1$ from the upper limit position again to form a new microdroplet 199. The above cycling is repeated.

Figure 21:
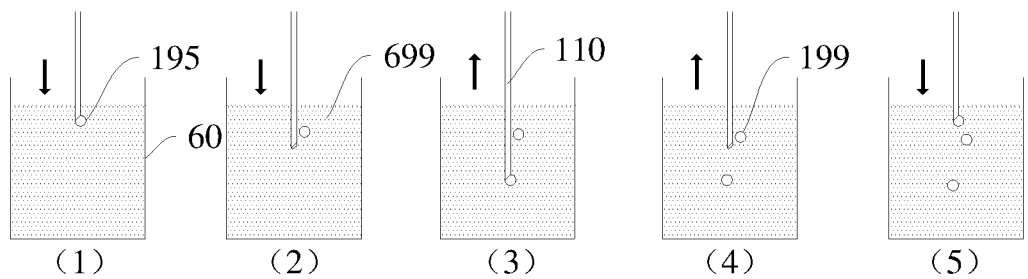
FIG. 21 is a schematic view illustrating a process of generating microdroplets by the liquid discharging nozzle having the beveled cut structure provided by another embodiment of the present application.

As shown in FIG. 21, in an embodiment of the present application, the angle between the normal line of the end surface of the outlet end 112 of the liquid discharging nozzle 110 and the extension direction of the tube body is 45°. The outlet end 112 of the liquid discharging nozzle 110 has a beveled structure. The liquid surface of the second liquid 699 faces upward. The liquid discharging nozzle 110 is disposed vertically. The outlet end 112 of the liquid discharging nozzle 110 moves below the liquid surface of the second liquid 699 along a vertical linear trajectory with a speed varying in a square wave form. Two microdroplets 199 are generated in one motion period of the outlet end 112 of the liquid discharging nozzle 110. The first liquid is stored in the liquid discharging nozzle 110. The liquid driving mechanism 120 controls the first liquid to be discharged from the outlet end 112 at a uniform flow rate. While the volume of the droplet 195 attached to the outlet end 112 of the liquid discharging nozzle 110 reaches a preset value, the outlet end 112 of the liquid discharging nozzle 110 instantaneously accelerates downward with the acceleration having a value $a_1$ from an upper limit position, in the meanwhile, the droplet 195 attached to the outlet end 112 of the liquid discharging nozzle 110 is detached from the outlet end 112 of the liquid discharging nozzle 110 to form the microdroplet 199. Under the action of the viscous force of the second liquid 699 and the press of the end surface of the outlet end 112 of the liquid discharging nozzle 110, the microdroplet 199 moves away from the moving trajectory of the outlet end 112 but proximate to a side wall of the liquid discharging nozzle 110. While the outlet end 112 of the liquid discharging nozzle 110 proceeds to move downward, the first liquid is further discharged from the outlet end 112 of the liquid discharging nozzle 110 to form the droplet 195 attached to the outlet end 112 of the liquid discharging nozzle 110, and the volume of the droplet 195 attached to the outlet end 112 of the liquid discharging nozzle 110 increases.

When the outlet end 112 of the liquid discharging nozzle 110 arrives at the lower limit position in motion, the volume of the droplet 195 attached to the outlet end 112 of the liquid discharging nozzle 110 is the same as that of the microdroplet 199 detached previously, and the outlet end 112 of the liquid discharging nozzle 110 instantaneously accelerates upward with the acceleration having a value $a_1$ from the lower limit position, causing the droplet 195 attached to the outlet end 112 to be detached from the outlet end 112 to form a new microdroplet 199. Under the action of the adhesion force of the outlet end 112, the microdroplet 199, generated when the outlet end 112 of the liquid discharging nozzle 110 is located at the lower limit position, moves upward just for a small distance and then starts to gradually fall in the second liquid 699. During the outlet end 112 of the liquid discharging nozzle 110 moving upward from the lower limit position, the first liquid is still discharged from the outlet end 112 of the liquid discharging nozzle 110, and the volume of the droplet 195 attached to the outlet end 112 of the liquid discharging nozzle 110 increases. When the outlet end 112 of the liquid discharging nozzle 110 arrives at the upper limit position, the volume of the droplet 195 attached to the outlet end 112 of the liquid discharging nozzle 110 is the same as that of the microdroplet 199 detached previously, and the outlet end 112 of the liquid discharging nozzle 110 instantaneously accelerates downward with the acceleration having a value $a_1$ from the upper limit position again to form a new microdroplet 199. The above cycle is repeated. When the outlet end 112 of the liquid discharging nozzle 110 moves downward from the upper limit position again, if any microdroplet 199 still exists in the range of the trajectory located right below the outlet end 112, then the droplet 195 attached to the outlet end 112 would impact on this generated microdroplet 199, causing the generated microdroplet 199 to move along the normal line of the end surface of the outlet end 112, thereby moving away from the moving trajectory of the outlet end 112.

The microdroplet 199 is generated during the liquid discharging nozzle 110 provided by the present application moving below the liquid surface of the second liquid 699. As an implementation manner, the outlet end 112 of the liquid discharging nozzle 110 moves blow the liquid surface of the second liquid 699 with a displacement changing in a sine form. The first liquid discharged from the outlet end 112 of the liquid discharging nozzle 110 is formed into a droplet 195 attached to the outlet end 112 of the liquid discharging nozzle 110. The droplet 195 is detached from the outlet end 112 of the liquid discharging nozzle 110 to form the microdroplet 199 when the moving speed of the outlet end 112 of the liquid discharging nozzle 110 reaches a certain value. As shown in FIG. 6, the forces, exerted upon the microdroplet 199 before the microdroplet 199 is detached from the outlet end 112 of the liquid discharging nozzle 110, are respectively the gravity G, the buoyancy $f_1$ from the second liquid 699, the viscous resistance $f_2$ from the second liquid 699, and the maximum adhesion force $f_3$ between the outlet end 112 of the liquid discharging nozzle 110 and the droplet 195. The microdroplet 199 has a mass m, a speed v, and an acceleration value $a_2$ before it is detached from the outlet end 112 of the liquid discharging nozzle 110. During motion in the second liquid 699, the droplet 195 bears a combined action of the viscous force $f_2$, the gravity G, the buoyancy $f_1$, and the adhesion force $f_3$, namely $m\vec{a}_2 = \vec{f}_1 + \vec{G} + \vec{f}_2 + \vec{f}_3$. The condition for detaching the droplet 195 from the outlet end 112 of the liquid discharging nozzle 110 (i.e., for generating one microdroplet 199) is $|\vec{f}_3| < |\vec{f}_1 + \vec{G} + \vec{f}_2 - m\vec{a}_2|$.

The maximum adhesion force $f_3$ between the outlet end 112 of the liquid discharging nozzle 110 and the droplet 195 is related to the surface free energy of the liquid discharging nozzle 110, the surface tension of the droplet 195, and the geometric dimension of the liquid discharging nozzle 110. The droplet 195 attached to the outlet end 112 of the liquid discharging nozzle 110 is simplified as a sphere. According to the Stokes formula, the viscous resistance force $f_2$ applied on the droplet 195 moving in the second liquid 699 satisfies $f_2 = 6\pi\eta rv$, wherein $\eta$ denotes a viscous coefficient of the second liquid 699, r denotes a radius of the droplet 195, and v denotes a moving speed of the droplet 195. In the process of generating the microdroplet 199, a volume of droplet 195 is generally in a range from picoliter magnitude order to microliter magnitude order, and generally, the viscosity coefficient of the second liquid 699 is relatively large. Therefore, generally, $|\vec{f}_2| \gg |\vec{G}|$, $|\vec{f}_2| \gg |\vec{f}_1|$ and $|\vec{f}_2| \gg |m\vec{a}_2|$. Therefore, when the outlet end 112 of the liquid discharging nozzle 110 periodically moves at a varying speed below the liquid surface of second liquid 699, the condition for detaching the droplet 195 from the outlet end 112 of the liquid discharging nozzle 110 (i.e., for generating one microdroplet 199) is approximately $|\vec{f}_3| < |\vec{f}_2|$. Optionally, one, two, or more microdroplets 199 are generated in one motion period of the outlet end 112 of the liquid discharging nozzle 110.

Figure 22:
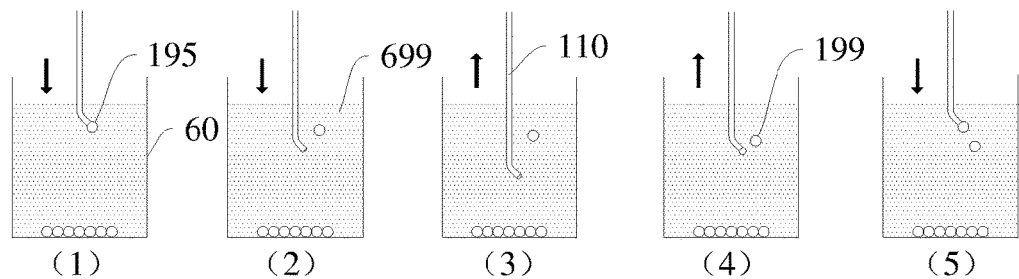
FIG. 22 is a schematic view illustrating a process of generating microdroplets by the liquid discharging nozzle having a bent structure provided by an embodiment of the present application.

As shown in FIG. 22, in an embodiment of the present application, the angle between the normal line of the end surface of the outlet end 112 of the liquid discharging nozzle 110 and the extension direction of the tube body is 45°. The portion of the needle stem 113 proximate to outlet end 112 of the liquid discharging nozzle 110 has a bent structure. The liquid surface of the second liquid 699 faces upward. The liquid discharging nozzle 110 is disposed vertically. The outlet end 112 of the liquid discharging nozzle 110 moves below the liquid surface of the second liquid 699 along a vertical linear trajectory with a displacement changing in the sine form. One microdroplet 199 is generated in one motion period of the outlet end 112 of the liquid discharging nozzle 110. The first liquid is stored in the liquid discharging nozzle 110. The liquid driving mechanism 120 controls the liquid discharging nozzle 110 to discharge a same volume of the first liquid in each motion period of the liquid discharging nozzle 110. The first microdroplet 199 is generated in the accelerated descending stage of the linear motion of the outlet end 112 of the liquid discharging nozzle 110, whose displacement changes in the sine form. At the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the outlet end 112 of the liquid discharging nozzle 110 has a downward decelerating stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110. When the outlet end 112 of the liquid discharging nozzle 110 descends to the limit position, it starts to ascend, and synchronously, the volume of the droplet 195 attached to the outlet end 112 of the liquid discharging nozzle 110 continuously increases.

When the first liquid is controlled to be discharged from the outlet end 112 of the liquid discharging nozzle 110 at the uniform flow rate, a new droplet 195 having the same volume as that of the previous microdroplet 199 is generated again at the outlet end 112 of the liquid discharging nozzle 110 at the moment one motion period passed right after the generation of the previous microdroplet 199. Moreover, the moving speed of the outlet end 112 of the liquid discharging nozzle 110 at this moment is also the same as that one motion period ago. The new droplet 195 having the same volume as that of the previous microdroplet 199 is detached from the outlet end 112 of the liquid discharging nozzle 110. Such a cycling is repeated. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form. When the outlet end 112 of the liquid discharging nozzle 110 moves downward again from the upper limit position, if one microdroplet 199 still exists in the range of the trajectory located right below the outlet end 112, then the droplet 195 attached to the outlet end 112 would impact on this generated microdroplet 199, causing the generated microdroplet 199 to move along the normal line of the end surface of the outlet end 112, thereby moving away from the moving trajectory of the outlet end 112.

Figure 23:
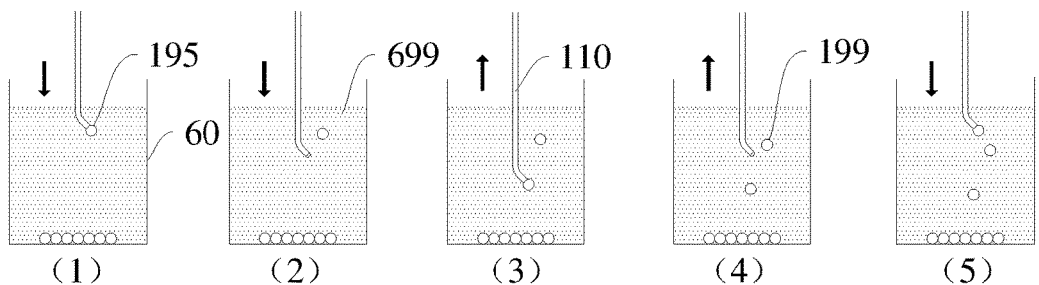
FIG. 23 is a schematic view illustrating a process of generating microdroplets by the liquid discharging nozzle having a bent structure provided by another embodiment of the present application.

As shown in FIG. 23, in an embodiment of the present application, the angle between the normal line of the end surface of the outlet end 112 of the liquid discharging nozzle 110 and the extension direction of the tube body is 45°. The portion of the needle stem 113 proximate to outlet end 112 of the liquid discharging nozzle 110 has a bent structure. The liquid surface of the second liquid 699 faces upward. The liquid discharging nozzle 110 is disposed vertically. The outlet end 112 of the liquid discharging nozzle 110 moves below the liquid surface of the second liquid 699 along a vertical linear trajectory with a displacement changing in the sine form. Two microdroplets 199 are generated in one motion period of the outlet end 112 of the liquid discharging nozzle 110. The first liquid is stored in the liquid discharging nozzle 110. The liquid driving mechanism 120 controls the first liquid to be discharged from the outlet end 112 at a uniform flow rate. The viscous resistance force $f_2$ applied on the droplet 195 moving in the second liquid 699 continuously increases with the increase of the radius r of the droplet 195 attached to the outlet end 112 of the liquid discharging nozzle 110. At the downward accelerating stage of the outlet end 112 of the liquid discharging nozzle 110, the viscous resistance force $f_2$ applied on the droplet 195 moving in the second liquid 699 is greater than the maximum adhesion force $f_3$ between the outlet end 112 of the liquid discharging nozzle 110 and the droplet 195, and the droplet 195 is detached from the outlet end 112 of the liquid discharging nozzle 110 to form the microdroplet 199. Under the action of the viscous force of the second liquid 699 and the press of the end surface of the outlet end 112 of the liquid discharging nozzle 110, the microdroplet 199 moves away from the moving trajectory of the outlet end 112 but proximate to the side wall of the liquid discharging nozzle 110.

The outlet end 112 of the liquid discharging nozzle 110 proceeds to move downward. When the outlet end 112 of the liquid discharging nozzle 110 descends to the limit position, it starts to ascend, and synchronously, the first liquid is further discharged from the outlet end 112 of the liquid discharging nozzle 110 to form the drop 195 attached to the outlet end 112 of the liquid discharging nozzle 110, and the volume of the drop 195 attached to the outlet end 112 of the liquid discharging nozzle 110 increases. At the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 has decreased. After that, the radius r of the droplet 195 slowly increases, and the viscous resistance force $f_2$ applied on the droplet 195 moving in the second liquid 699 changes mainly with the moving speed of the outlet end 112 of the liquid discharging nozzle 110.

After a time interval of half a period, the outlet end 112 of the liquid discharging nozzle 110 is at the upward accelerating stage. When the volume of the droplet 195 attached to the outlet end 112 of the liquid discharging nozzle 110 is the same as that of the microdroplet 199 detached previously, and when the speed of the outlet end 112 of the liquid discharging nozzle 110 is the same as that in the first half period, the droplet 195 attached to the outlet end 112 of the liquid discharging nozzle 110 is detached from the outlet end 112 and forms a new microdroplet 199. Under the action of the adhesion force of the outlet end 112, the microdroplet 199, generated at the upward accelerating stage of the outlet end 112 of the liquid discharging nozzle, moves upward just for a small distance and starts to fall gradually in the second liquid 699. In the meanwhile, the first liquid is further discharged from the outlet end 112 of the liquid discharging nozzle 110 to form the droplet 195 attached to the outlet end 112 of the liquid discharging nozzle 110. After a time interval of half a period, the outlet end 112 of the liquid discharging nozzle 110 enters the downward accelerating stage. When the volume of the droplet 195 attached to the outlet end 112 of the liquid discharging nozzle 110 is the same as that of the microdroplet 199 detached previously, and when the speed of the outlet end 112 of the liquid discharging nozzle 110 is the same as that half a period ago, the droplet 195 attached to the outlet end 112 of the liquid discharging nozzle 110 is detached from the outlet end 112 and forms a new microdroplet 199. Such a cycling is repeated. The first liquid is controlled to be discharged from the outlet end 112 of the liquid discharging nozzle 110 at the uniform flow rate. After the second microdroplet 199 is generated at the accelerating stage in the second half motion period of the outlet end 112 of the liquid discharging nozzle 110 which moves along the vertical linear trajectory with the displacement changing in the sine form, a stage of stably generating the microdroplet 199 starts. The uniformity of the volume values of the generated microdroplets 199 is guaranteed cooperatively by the uniform discharging flow rate of the first liquid and the vibration motion of the outlet end 112 of the liquid discharging nozzle 110 having the displacement changing in the sine form. When the outlet end 112 of the liquid discharging nozzle 110 moves downward again from the upper limit position, if one microdroplet 199 still exists in the range of the trajectory located right below the outlet end 112, then the droplet 195 attached to the outlet end 112 would impact on this generated microdroplet 199, causing the generated microdroplet 199 to move along the normal line of the end surface of the outlet end 112, thereby moving away from the moving trajectory of the outlet end 112.

The microdroplet generating device and method provided by the present application can be widely applied to the application field such as medical clinical test, preparation of nano-material, food and environment detections, biochemical analysis, and so on. In a specific application scenario, the microdroplet 199 generating device and method provided by the present application is applied to the polymerase chain reaction (PCR).

A sectional dimension of the liquid discharging nozzle 110 is generally of the order of micrometer. The conventional surface processing method is mostly applied for components having relatively large dimensions and thus is not fully appropriate for the liquid discharging nozzle 110 having the relatively small dimensions.

In view of this, to solve the problem that the conventional surface processing method is mostly applied for components having relatively large dimensions and thus is not fully appropriate for the liquid discharging nozzle 110 having the relatively small dimensions, it is necessary to provide a surface processing method appropriate for the liquid discharging nozzle 110 having the dimensions of the order of micrometer.

Figure 24:
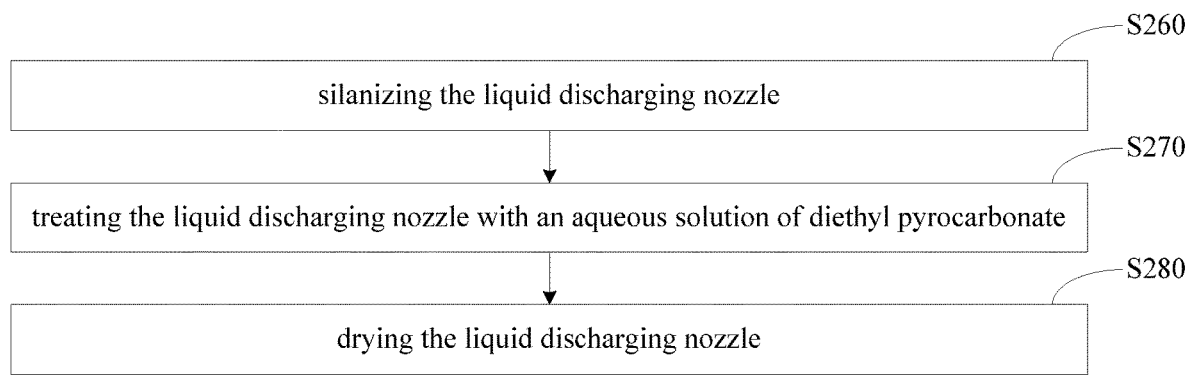
FIG. 24 is a flowchart of a method for processing a surface of the liquid discharging nozzle provided by an embodiment of the present application.

As shown in FIG. 24, in an embodiment of the present application, a surface processing method for the liquid discharging nozzle 110 is provided to process the surface of the liquid discharging nozzle 110, and the surface processing method includes steps of: S260, silanizing the liquid discharging nozzle 110; S270, treating the liquid discharging nozzle 110 with an aqueous solution of diethyl pyrocarbonate (DEPC); S280, drying the liquid discharging nozzle 110.

In the above-mentioned surface processing method for the liquid discharging nozzle 110, the surface free energy of the liquid discharging nozzle 110 is reduced and can be controlled within a certain range via the silanization, thereby decreasing the effect of the surface property of the liquid discharging nozzle 110 on the generation process of the microdroplet 199.

Figure 25:
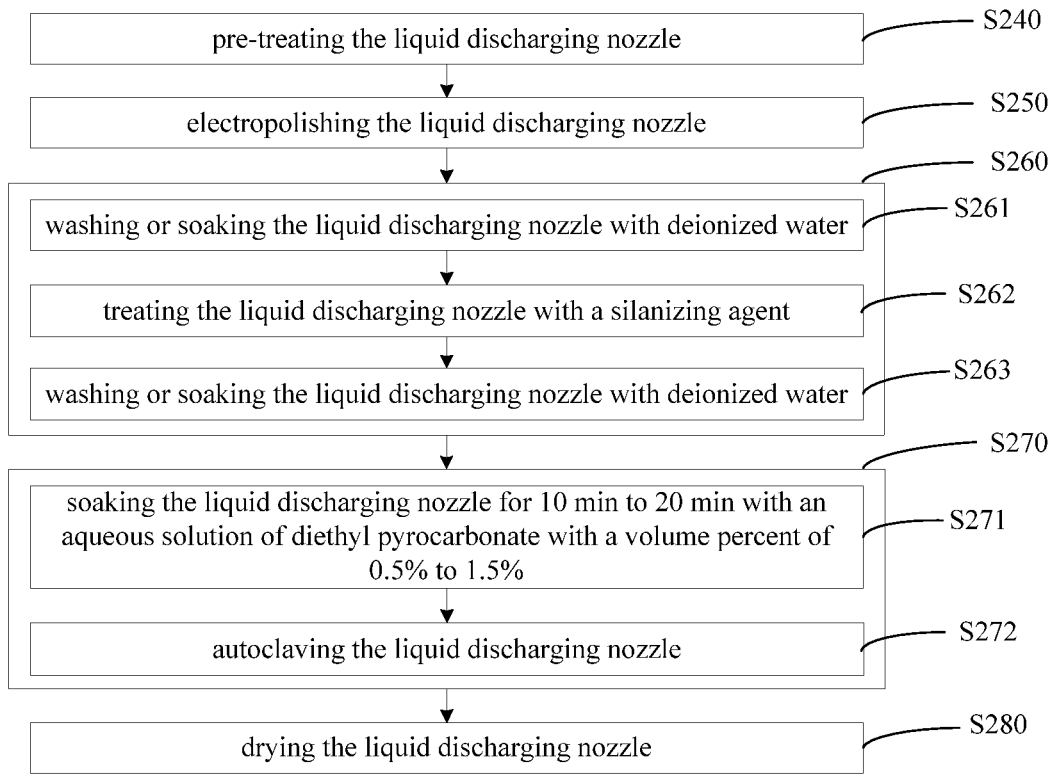
FIG. 25 is a flowchart of a method for processing the surface of the liquid discharging nozzle provided by another embodiment of the present application.

As shown in FIG. 25, in an embodiment of the present application, a step S240 of pre-treating the liquid discharging nozzle 110 is further included before the step S260. In the step S240, the pre-treatment of the liquid discharging nozzle 110 includes one or more of operations such as degreasing, decontamination, washing, and so on. The contaminant or interfering substance attached on the surface of the liquid discharging nozzle 110 can be effectively removed in the pre-treating process by means of degreasing, decontaminating, and washing the liquid discharging nozzle 110.

Furthermore, in the step S240, the ultrasonic oscillation can be used to assist the degreasing, the decontamination, and the washing of the surface of the liquid discharging nozzle 110. Chemical means and mechanical means are combined by means of degreasing, decontaminating, and washing the liquid discharging nozzle 110 in the ultrasonic environment, thus ensuring the effect of the pre-treatment of the liquid discharging nozzle 110. More specifically, in the step S240, the liquid discharging nozzle 110 is made of stainless steel material, and a stainless steel cleaning agent is used to wash the liquid discharging nozzle 110. A better cleaning effect can be achieved for the liquid discharging nozzle 110 made of stainless steel material via the stainless steel cleaning agent. In other embodiments, other methods capable of cleaning the surface of the liquid discharging nozzle 110 can also be used in the pre-treatment of the surface of the liquid discharging nozzle 110. In other embodiments of the present application, the liquid discharging nozzle 110 is one of a quartz capillary, a glass tube, a double-optical fiber capillary, and so on.

In another embodiment of the present application, a step S250 of electropolishing the liquid discharging nozzle is included after the step S240 and before the step S260. The surface roughness of the liquid discharging nozzle 110 with a relatively small size can be reduced via the electropolishing, so as to enable the surface quality of the liquid discharging nozzle 110 to meet the requirements of the silanization. The electropolishing is of great importance for the surface quality of the liquid discharging nozzle 110 and is crucial for the surface quality of the liquid discharging nozzle 110 made of the stainless steel material to meet the standard. In an embodiment of the present application, the liquid discharging nozzle 110 made of the stainless steel material is used as a positive pole, while insoluble copper in an electrolyte is used as a negative pole. The two poles are simultaneously immersed into an electrolytic cell. A direct current is applied to selectively dissolve the liquid discharging nozzle 110 used as the positive pole, thereby achieving the purpose of polishing the surface of the liquid discharging nozzle 110. In this embodiment, the process parameters for electropolishing the liquid discharging nozzle 110 are shown in the following table:

| Electropolishing Process Parameter Table | | | |
|---|---|---|---|
| Electrolytic voltage | 12 V | Electrolytic time | 30s |
| Pulse frequency | 60 HZ | Electrolytic temperature | 50° C. |
| Electrolytic current | <1A/cm$^2$ | Electrolyte | 50%-60% phosphoric acid |

In the process of electropolishing, the liquid discharging nozzle 110 used has an inner diameter of 60 μm and an outer diameter of 150 μm. After the electropolishing, no obvious scratch was found when the liquid discharging nozzle was amplified by 50 times by a metalloscope.

An amorphous silicon film can be formed on the surface of the liquid discharging nozzle 110 after the step S260. Preferably, the amorphous silicon film is formed on the surface of the liquid discharging nozzle 110 via a method of chemical vapor deposition. The amorphous silicon film preferably has a thickness of 100 angstroms to 1000 angstroms.

As shown in FIG. 25, in an embodiment of the present application, the step S260 includes: S261, washing or soaking the liquid discharging nozzle 110 with deionized water; S262, treating the liquid discharging nozzle 110 with a silanizing agent; S263, washing or soaking the liquid discharging nozzle 110 with deionized water.

The electrolyze liquid discharging nozzle 110 is washed or soaked with deionized water before the silanization to remove stains and the static electricity on the surface of the liquid discharging nozzle 110. The surface free energy of the liquid discharging nozzle 110 is reduced and controlled within a certain range via the processing of silanization, thereby decreasing the effect of the surface property of the liquid discharging nozzle 110 on the generation process of the microdroplet 199. The silanized liquid discharging nozzle 110 is washed or soaked with deionized water after the silanization to remove stains and the static electricity on the surface of the liquid discharging nozzle 110. In the step S262, preferably, an amorphous silicon film is formed on the surface of the liquid discharging nozzle 110 by using a silanizing agent via a method of chemical vapor deposition. Preferably, the silanizing agent is a silicon tetrahydride gas, and more preferably, a mixture gas including silicon tetrahydride and phosphorus hydride (as a dopant). The surface free energy of the liquid discharging nozzle 110 is decreased by means of forming the amorphous silicon film on the surface of the liquid discharging nozzle 110.

In this embodiment, the specific steps of the silanization of the stainless steel surface are as follows: placing the electrolyzed liquid discharging nozzle 110, made of stainless steel material, into a chemical vapor deposition chamber; removing moisture on the surface of the liquid discharging nozzle 110, and vacuumizing the chemical vapor deposition chamber to be in a vacuum state; feeding a mixture gas including silicon tetrahydride and phosphorus hydride; controlling a vapor deposition pressure within a range between 0.1 Pa to 500 Pa; controlling a vapor deposition temperature within a range between 180° C. to 500° C., and performing the chemical vapor deposition for a deposition time of 0.4 h to 8 h; after the deposition, feeding nitrogen gas and cooling to a room temperature. More specifically, a volume percent of the silicon tetrahydride in the mixture gas is from 95.0% to 99.9% and a volume percent of the phosphorus hydride in the mixture gas is from 0.1% to 5.0%

As shown in FIG. 25, the step S270 includes: S271, soaking the liquid discharging nozzle 110 for 10 min to 20 min with an aqueous solution of diethyl pyrocarbonate with a volume percent of 0.5% to 1.5%; S272, autoclaving the liquid discharging nozzle 110. The liquid discharging nozzle 110 is soaked by using the DEPC aqueous solution with a volume percent of 1%, so as to guarantee that no ribonuclease (RNase), deoxyribonuclease (DNase), and the like exists on the surface of the liquid discharging nozzle 110, thereby reducing the interference in the subsequent operations using the liquid discharging nozzle 110. By autoclaving the liquid discharging nozzle 110, the DEPC aqueous solution remained on the surface of the liquid discharging nozzle 110 can be effectively removed, moreover, RNase, DNase, and the like which are not removed by the DEPC aqueous solution can be removed.

The time period for soaking the liquid discharging nozzle 110 with the DEPC aqueous solution with the volume percent of 1% can be determined according to specific operation conditions. Furthermore, the liquid discharging nozzle 110 is soaked with the DEPC aqueous solution with the volume percent of 1% for 15 min. After the test, it is found that RNase and DNase on the surface of the liquid discharging nozzle 110 can be fully removed within 15 min. Yet furthermore, in the step S280, the liquid discharging nozzle 110 is further cleaned by means of a nitrogen purification furnace. The liquid discharging nozzle 110 can be cleaned, dried, and baked by the nitrogen purification furnace. In a process of drying and baking the liquid discharging nozzle 110, the nitrogen gas is used as a protection gas, thereby effectively avoiding the chemical reaction between a gas having a relatively active chemical property in the environment and the surface of the liquid discharging nozzle, and achieving an effective protection for the liquid discharging nozzle 110.

In one specific embodiment of the present application, in the electropolishing process, the liquid discharging nozzle 110 has an inner diameter of 60 μm and an outer diameter of 150 μm. The electrolyzed liquid discharging nozzle 110 is soaked in deionized water for 5 min and then placed into the chemical vapor deposition chamber, which is then evacuated to be in a vacuum state and fed with the mixture gas of silicon tetrahydride and phosphorus hydride. The vapor deposition pressure is controlled to be 300±20 Pa, and the vapor deposition temperature is controlled to be 350±20° C. The volume percent of the silicon tetrahydride in the mixture gas is 97.0%, and the volume percent of the phosphorus hydride in the mixture gas is 3.0%. The deposition time is 2 h. After the deposition is finished, nitrogen gas is fed, and the temperature decreases to the room temperature. The silanizated liquid discharging nozzle 110 is washed with deionized water. Then the entire liquid discharging nozzle 110 is soaked 1% of the EDPC aqueous solution for 15 min and then is autoclaved. Finally, the liquid discharging nozzle 110 is placed into the nitrogen purification furnace to have its surface cleaned.

Eighteen liquid discharging nozzles 110 having a same size are processed in a batch by using the surface processing method for the liquid discharging nozzle 110 provided in the embodiments of the present application. Then an experiment, in which the droplet 195 is suspended, is performed on the eighteen liquid discharging nozzles 110 respectively. Driven by the liquid controlling mechanism, the first liquid is discharged from the outlet end 112 of the liquid discharging nozzle 110 at a flow rate of 1.0 nL/s. Start timing once the previous microdroplet 199 drops. The time taken by one hundred microdroplets 199 from each liquid discharging nozzle 110 to drop is calculated. Average time taken by one hundred droplets 195 from each of the eighteen liquid discharging nozzles 110 to drop is listed in the following table:

Statistical Table of Time Taken by Droplets to Drop

| No. of liquid discharging nozzle 110 | Average time(s) taken by droplets to drop |
| --- | --- |
| 1 | 8.02 |
| 2 | 8.01 |
| 3 | 8.00 |
| 4 | 7.99 |
| 5 | 8.01 |
| 6 | 7.98 |
| 7 | 8.01 |
| 8 | 8.02 |
| 9 | 8.00 |
| 10 | 7.99 |
| 11 | 7.99 |
| 12 | 7.98 |
| 13 | 8.01 |
| 14 | 8.00 |
| 15 | 8.02 |
| 16 | 8.01 |
| 17 | 8.00 |
| 18 | 8.02 |

The relative variation range of the average time taken by the microdroplets 199 corresponding to each of the eighteen liquid discharging nozzles 110 can directly reflect a relative variation range of the surface free energy among the eighteen liquid discharging nozzles 110. From the above experimental data, it can be calculated that a standard deviation of the surface free energies of the liquid discharging nozzles 110 processed in batch by using the surface processing method of the liquid discharging nozzle 110 provided by the embodiments of the present application is 1.33%, which is sufficient to meet the uniformity requirement for the volume values of the multiple microdroplets 199.

In an embodiment of the present application, one end of the liquid discharging nozzle 100 is the outlet end 112. The surface processing is performed for the outlet end 112 and the outer side wall of the liquid discharging nozzle 110 via the surface processing method of the liquid discharging nozzle. Since the surface processing is performed for both of the outlet end 112 and the outer side wall of the liquid discharging nozzle 110, after the outlet end 112 and the outer side wall of the liquid discharging nozzle 110 contact the generated microdroplet 199 in the generation process of the microdroplet 199, the uniform surface enables the microdroplet 199 to be pushed away effectively, avoiding breaking the microdroplet 199.

In the generation process of the microdroplet, the outlet end of the liquid discharging nozzle is in a moving state, and the flow rate of the liquid discharged by the conventional liquid driving mechanism is unstable and uncontrollable. Therefore, the volume sizes of the generated microdroplets are random. In view of this, to solve the problem of the random volume sizes of the microdroplets, which is caused by the unstable and uncontrollable flow rate of the liquid discharged from the conventional liquid discharging nozzle in the moving state, it is necessary to provide a liquid driving mechanism enabling liquid to be discharged from the liquid discharging nozzle at a preset flow rate.

In the generation process of the microdroplet 199, the first liquid is discharged from the outlet end 112 of the liquid discharging nozzle 110 at the preset flow rate. When the outlet end 112 of the liquid discharging nozzle 110 makes a periodic motion including the instantaneous acceleration, not only the microdroplets 199 can be effectively generated, but also the sizes of the generated microdroplets 199 can be controlled conveniently. When the outlet end 112 of the liquid discharging nozzle 110 makes a periodic motion with displacement changing in the sine form, not only the microdroplets 199 can be effectively generated, but also the volume sizes of the generated microdroplets 199 are highly uniform. In the above-mentioned two generation processes of the microdroplet 199, the liquid driving mechanism drives the first liquid to be discharged from the outlet end 112 of the liquid discharging nozzle 110 at the preset flow rate.

Figures 26, 27:
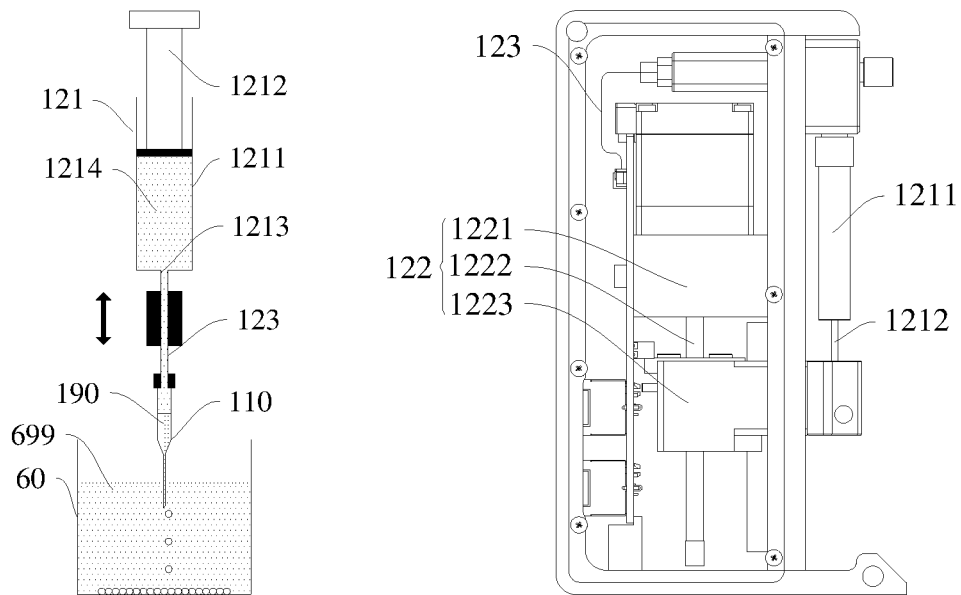
FIG. 26 is a schematic view illustrating a connection of a liquid controlling mechanism with the liquid discharging nozzle provided by an embodiment of the present application.
FIG. 27 is a schematic structural view of the liquid controlling mechanism provided by an embodiment of the present application.

As shown in FIGS. 26 and 27, the liquid driving mechanism 120 is provided by the present application and applied in the microdroplet generating system. The liquid driving mechanism includes a volume-variable assembly 121 and a power assembly 122. The volume-variable assembly 121 includes a syringe barrel 1211 and a push rod 1212. The push rod and an inner wall of the syringe barrel 1211 slidably match. The syringe barrel 1211 can store a driving liquid 1214 therein. The syringe barrel 1211 has a liquid inlet/outlet 1213 configured to communicate with the inlet end 111 of the liquid discharging nozzle 110 storing the first liquid 190 therein. The power assembly 122 is connected to the push rod 1212 and configured to drive the push rod 1212 to slide in an extension direction of the syringe barrel 1211. In the generation process of the microdroplet 199, the power assembly 122 drives the push rod 1212 to press the driving liquid 1214 stored in the syringe barrel 1211, and the driving liquid 1214 presses the first liquid 190 stored in the liquid discharging nozzle 110, thus the first liquid 190 is discharged from the outlet end 112 of the liquid discharging nozzle 110. On the basis of the incompressibility of liquid (driving liquid 1214), the liquid driving mechanism 120 provided in the present application ensures that the first liquid 190 is discharged from the outlet end 112 of the liquid discharging nozzle 110 at the preset flow rate, even though the outlet end 112 of the liquid discharging nozzle 110 vibrates at a high frequency. The volume of the generated microdroplet 199 can be accurately controlled by the liquid driving mechanism 120 provided by the present application. The liquid driving mechanism 120 provided by the present application is not limited to the above-mentioned implementation manner, for example can be a peristaltic pump, a pressure-driven pump, a gas pressure-driven pump, an electroosmotic driving pump, and so on.

As an implementation manner, the liquid inlet/outlet 1213 of the syringe barrel 1211 communicates with the inlet end 111 of the liquid discharging nozzle 110 via a slim tube 123. The driving liquid 1214 is stored in the syringe barrel 1211 and in the slim tube 123. The power assembly 122 is connected to the push rod 1212 of the volume-variable assembly 121 and configured to drive the push rod 1212 of the volume-variable assembly 121 to slide in the syringe barrel 1211. In the generation process of the microdroplet 199, the power assembly 122 drives the push rod 1212 of the volume-variable assembly 121 to press the driving liquid 1214 stored in the syringe barrel 1211 and the slim tube 123, and the driving liquid 1214 presses the first liquid 190 stored in the liquid discharging nozzle 110, thereby discharging the first liquid 190 from the outlet end 112 of the liquid discharging nozzle 110. The slim tube 123 is configured to connect the liquid inlet/outlet 1213 of the syringe barrel 1211 with the inlet end 111 of the liquid discharging nozzle 110. On one hand, the slim tube 123 has a relatively small inner diameter, so that the volume of the discharged liquid can be accurately controlled by controlling a travel distance of the push rod 1212. On the other hand, the arrangement of the slim tube 123 enables the positions of the syringe barrel 1211 and the liquid discharging nozzle 110 and the distance therebetween to be flexibly designed, so that other necessary components can be arranged between the syringe barrel 1211 and the liquid discharging nozzle 110.

In an embodiment of the present application, the power assembly 122 drives the push rod 1212 to slide in the syringe barrel 1211 at a constant speed, that is, pushed by the push rod 1212, the driving liquid 1214 is discharged from the liquid inlet/outlet 1213 of the volume-variable assembly 121 at a uniform flow rate and enters into the liquid discharging nozzle 110 at the uniform flow rate through the slim tube 123, and pressed by the driving liquid 1214, the first liquid 190 stored in the liquid discharging nozzle 110 is discharged from the outlet end 112 of the liquid discharging nozzle 110 at a uniform flow rate. By using the driving liquid 1214 as the transmission medium and controlling the push rod 1212 to discharge the driving liquid 1214 at the uniform flow rate, the liquid driving mechanism 120 provided in this embodiment enables the first liquid 190 to be discharged from the outlet end 112 of the liquid discharging nozzle 110 at the uniform flow rate not only when the liquid discharging nozzle 110 is in a static state, but also when the liquid discharging nozzle 110 vibrates fast. The liquid driving mechanism 120 provided in this embodiment significantly improves the uniformity of the volume of the generated microdroplets 199.

The power assembly 122 is configured to drive the push rod 1212 to slide in the syringe barrel 1211 in a direction leaving away from or coming close to the liquid inlet/outlet 1213. Optionally, the power assembly 122 can be a component that directly outputs a linear motion, such as an air cylinder or a hydraulic cylinder, or can be a component that converts a circular motion into a linear motion, such as a combination of a motor with a synchronous pulley, a combination of a motor with a screw 1222 and a sliding block 1223, and so on. The specific structure of the power assembly 122 is not limited in the present application. As shown in FIG. 27, in an embodiment of the present application, the power assembly 122 includes a driving motor 1221, a screw rod 1222, and a sliding block 1223. An output shaft of the driving motor 1221 is connected to and drives one end of the screw 1222. The sliding block 1223 has internal threads, and the sliding block 1223 is connected with the screw 1222 and matched with external threads on a surface of the screw 1222. An outer edge of the sliding block 1223 is fixedly connected to one end of the push rod 1212 away from the syringe barrel 1211. The sliding block 1223 and the screw 1222 operate cooperatively to transform the rotational motion output by the driving motor 1221 into the linear motion of the sliding block 1223 in an axial direction of the screw 1222, so as to drive the push rod 1212 of the volume-variable assembly 121 to slide in the syringe barrel 1211. Furthermore, the driving motor 1221 in this embodiment is a servo motor which has characteristics of accurately feeding back and controlling the output angular displacement.

Figure 28:
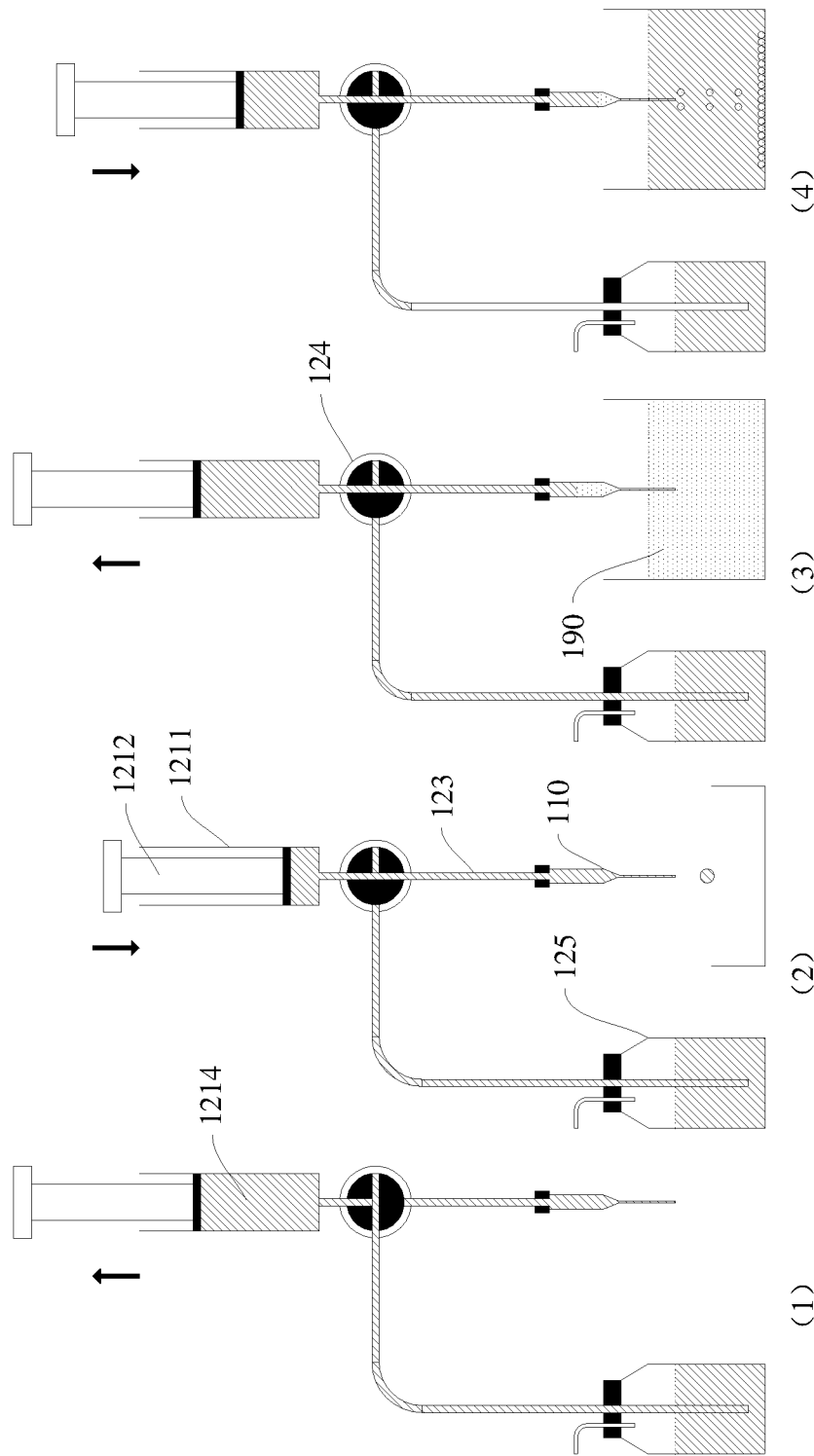
FIG. 28 is a schematic view illustrating a process of generating microdroplets by the liquid discharging nozzle driven by a driving liquid provided by an embodiment of the present application.

As shown in FIG. 28, in an embodiment of the present application, the liquid driving mechanism 120 further includes a three-way reversing valve 124 and a reservoir 125. The three-way reversing valve 124 has a first port, a second port, and a third port respectively in communication with the inlet end 111 of the liquid discharging nozzle 110, the liquid inlet/outlet 1213 of the volume-variable assembly 121, and the reservoir 125. The liquid driving mechanism 120 can be controlled to achieve at least the following two modes via the three-way reversing valve 124 as follows: (1. the liquid inlet/outlet 1213 of the volume-variable assembly 121 communicates with the inlet end 111 of the liquid discharging nozzle 110, and driven by the power assembly 122, the volume-variable assembly 121 provides a liquid driving force for the liquid discharging nozzle 110 to discharge the first liquid 190 in the liquid discharging nozzle 110 from the outlet end 112 of the liquid discharging nozzle 110, or to suck the first liquid 190 from the outlet end 112 of the liquid discharging nozzle 110 into the liquid discharging nozzle 110; 2. the liquid inlet/outlet 1213 of the volume-variable assembly 121 communicates with the reservoir 125, and driven by the power assembly 122, the volume-variable assembly 121 sucks the driving liquid 1214 in the reservoir 125 into the syringe barrel 1211 of the volume-variable assembly 121, or the volume-variable assembly 121 pushes the driving liquid 1214 in the volume-variable assembly 121 into the reservoir 125.

As shown in FIG. 28, a liquid driving method by using the above-described liquid driving mechanism is further provided in an embodiment of the present application. The method includes steps of: 1. communicating the liquid inlet/outlet 1213 of the volume-variable assembly 121 with the reservoir 125 via the three-way reversing valve 124, and driving, by the power assembly 122, the push rod 1212 to slide in the syringe barrel 1211 toward an end away from the liquid inlet/outlet 1213 to change the volume of the syringe barrel 1211, so as to suck the driving liquid 1214 in the reservoir 125 into the syringe barrel 1211; 2. communicating the liquid inlet/outlet 1213 of the volume-variable assembly 121 with the inlet end 111 of the liquid discharging nozzle 110 via the three-way reversing valve 124, and driving, by the power assembly 122, the push rod 1212 to slide in the syringe barrel 1211 toward an end proximate to the liquid inlet/outlet 1213 to change the volume of the syringe barrel 1211, so as to discharge the gas in the syringe barrel 1211, the slim tube 123, and the liquid discharging nozzle 110; 3. inserting the outlet end 112 of the liquid discharging nozzle 110 into the first liquid 190, and maintaining the three-way reversing valve 124 to allow the liquid inlet/outlet 1213 of the volume-variable assembly 121 to be in communication with the inlet end 111 of the liquid discharging nozzle 110, and driving, by the power assembly 122, the push rod 1212 to slide in the syringe barrel 1211 toward the end away from the liquid inlet/outlet 1213 to change the volume of the syringe barrel 1211, so as to suck the first liquid 190 into the liquid discharging nozzle 110; 4. maintaining the three-way reversing valve 124 to the liquid inlet/outlet 1213 of the volume-variable assembly 121 to be in communication with the inlet end 111 of the liquid discharging nozzle 110, and driving, by the power assembly 122, the push rod 1212 to slide in the syringe barrel 1211 toward the end close to the liquid inlet/outlet 1213 at a constant speed to change the volume of the syringe barrel 1211, so as to discharge the first liquid 190 stored in the liquid discharging nozzle 110 from the outlet end 112 of the liquid discharging nozzle 110 at a uniform flow rate.

To facilitate the smooth discharge of the gas in the syringe barrel 1211 in the above step (2), as shown in FIG. 27, the liquid inlet/outlet 1213 of the syringe barrel 1211 faces upwards, and the push rod 1212 vertically slides in the syringe barrel 1211.

In order to improve the generation efficiency of the microdroplet 199, as an implementation manner, the number of the liquid discharging nozzles 110 is plural. The plurality of liquid discharging nozzles 110 are spaced and arranged in a line or arranged in other form. Each liquid discharging nozzle 110 communicates with the first port of the three-way reversing valve 124 via one separate slim tube 123. The number of the volume-variable assembly 121 is one. The liquid inlet/outlet 1213 of the volume-variable assembly 121 communicates with the second port of the three-way reversing valve 124. The third port of the three-way reversing valve 124 communicates with the reservoir 125. Driven by the power assembly 122, the push rod 1212 slides in the syringe barrel 1211 in the direction coming close to the liquid inlet/outlet 1213 at the constant speed, and the driving liquid 1214 is pushed into the plurality of liquid discharging nozzles 110. Since the plurality of slim tubes 123 are connected in parallel, the flow rates of the driving liquid 1214 in respective slim tubes 123 are identical. Accordingly, it is guaranteed that the first liquid 190 in the plurality of liquid discharging nozzles 110 can be discharged from the outlet ends 112 of the liquid discharging nozzles 110 at the same and constant flow rate, thereby ensuring the uniformity of the volume of the generated microdroplets 199.

In order to improve the generation efficiency of the microdroplet 199, as another implementation manner, the number of the liquid discharging nozzles 110 and the number of the volume-variable assemblies 121 both are plural. The plurality of liquid discharging nozzles 110 are spaced and arranged in a line or arranged in other form. Each liquid discharging nozzle 110 communicates with the first port of the three-way reversing valve 124 via one separate slim tube 123. The liquid inlet/outlet 1213 of each volume-variable assembly 121 communicates with the second port of the three-way reversing valve 124 via one separate slim tube 123 as well. The third port of the three-way reversing valve 124 communicates with the reservoir 125. The plurality of volume-variable assemblies 121 are spaced and arranged in a line or arranged in other form. The ends of the push rods 1212 away from the syringe barrels 1211 of the plurality of volume-variable assemblies 121 are fixed relative to each other and synchronously pushed by the power assembly 122. The power assembly 122 drives the plurality of push rods 1212 to slide in respective syringe barrels 1211 in the direction coming close to the liquid inlet/outlet 1213 at the constant speed, while the driving liquids 1214 are pushed into the plurality of liquid discharging nozzles 110. Since the plurality of slim tubes 123 are connected in parallel, the flow rates of the driving liquids 1214 in respective slim tubes 123 are identical, thus it is guaranteed that the first liquids 190 in the plurality of liquid discharging nozzles 110 can be discharged from the outlet ends 112 of the liquid discharging nozzles 110 at the same and constant flow rate, thereby ensuring the uniformity of the volume of the generated microdroplets 199.

Figure 29:
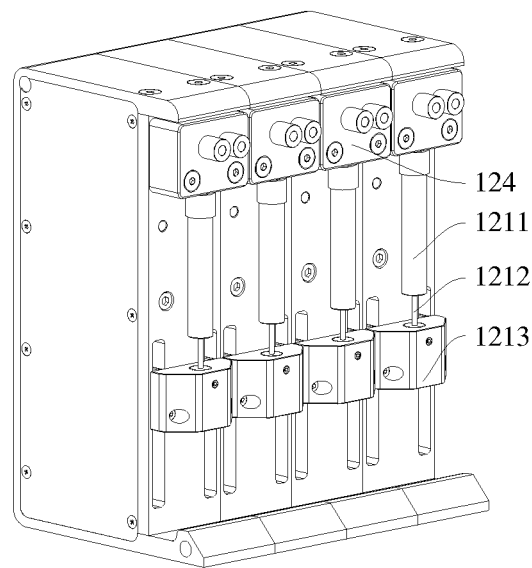
FIG. 29 is a schematic structural view of the liquid controlling mechanism provided by another embodiment of the present application.

In order to increase the generation efficiency of the microdroplet 199, as a third implementation manner, as shown in FIG. 29, the number of the liquid discharging nozzles 110, the number of the volume-variable assemblies 121, and the number of the three-way reversing valves 124 are all plural. The inlet end 111 of each liquid discharging nozzle 110 separately communicates with the first port of one corresponding three-way reversing valve 124 via one separate slim tube 123. The liquid inlet/outlet 1213 of each volume-variable assembly 121 separately communicates with the second port of one corresponding three-way reversing valve 124 via one separate slim tube 123. The third port of each three-way reversing valve 124 separately communicates with the reservoir 125. Optionally, the number of the reservoir 125 can be one or more. The first liquid 190 in respective liquid discharging nozzles 110 can be identical or different. The plurality of volume-variable assemblies 121 are spaced and arranged in a line or arranged in other form. The ends of the push rods 1212 away from the syringe barrels 1211 of the plurality of volume-variable assemblies 121 are fixed relative to each other and synchronously driven by the power assembly 122. The power assembly 122 drives the plurality of push rods 1212 to slide in respective syringe barrels 1211 in the direction coming close to the liquid inlet/outlet 1213 at the constant speed. Multiple different types of microdroplets 199 can be simultaneously generated.

In order to increase the generation efficiency of the microdroplet 199, as a fourth implementation manner, the number of the liquid discharging nozzles 110, the number of the volume-variable assemblies 121, and the number of the three-way reversing valves 124 are all plural and are identical. The inlet end 111 of each liquid discharging nozzle 110 separately communicates with the first port of one corresponding three-way reversing valve 124 via one separate slim tube 123. The liquid inlet/outlet 1213 of each volume-variable assembly 121 separately communicates with the second port of one corresponding three-way reversing valve 124 via one separately slim tube 123. The third port of each three-way reversing valve 124 separately communicates with the reservoir 125. Optionally, the number of the reservoir 125 can be one or more. The first liquid 190 in respective liquid discharging nozzles 110 can be identical or different. The plurality of volume-variable assemblies 121 are spaced and arranged in a line or arranged in other form. Each volume-variable assembly 121 corresponds to one separate power assembly 122. The power assembly 122 drives the plurality of push rods 1212 to slide in respective syringe barrels 1211 in the direction coming close to the liquid inlet/outlet 1213 at the constant speed. Accordingly, not only multiple different types of microdroplets 199 can be simultaneously generated, but also the volume of each type of droplet 195 can be separately controlled while ensuring that the volume of the microdroplets 199 generated by all liquid discharging nozzle 110 are identical. Therefore, it is convenient to independently control the generation states of the microdroplets of the plurality of the liquid discharging nozzles 110.

As for the conventional motion controlling mechanism, the relative motion between the outlet end of the liquid discharging nozzle and the oil phase mixture cannot be accurately controlled, and thus the uniformity of the volume of the generated microdroplets is relatively poor.

In view of this, to solve the problem of the conventional motion controlling mechanism that, the relative motion between the outlet end of the liquid discharging nozzle and the oil phase mixture cannot accurately controlled by using the liquid discharging nozzle injecting/spraying method, ant that the uniformity of the volume of the generated microdroplets is relatively poor, it is necessary to provide a motion controlling mechanism capable of accurately controlling the relative motion between the outlet end of the liquid discharging nozzle and the oil phase mixture.

In the generation process of the microdroplet 199, when the outlet end 112 of the liquid discharging nozzle 110 makes a periodic motion with the instantaneous acceleration, not only the microdroplets 199 can be effectively generated, but also the sizes of the generated microdroplets 199 can be controlled conveniently. When the outlet end 112 of the liquid discharging nozzle 110 makes a periodic motion with displacement changing in the sine form, not only the microdroplets 199 can be effectively generated, but also the volume sizes of the generated microdroplets 199 are highly uniform. The motion controlling mechanism 130 drives the outlet end 112 of the liquid discharging nozzle 110 to make the periodic motion with the instantaneous acceleration or with displacement changing in the sine form.

Figure 30:
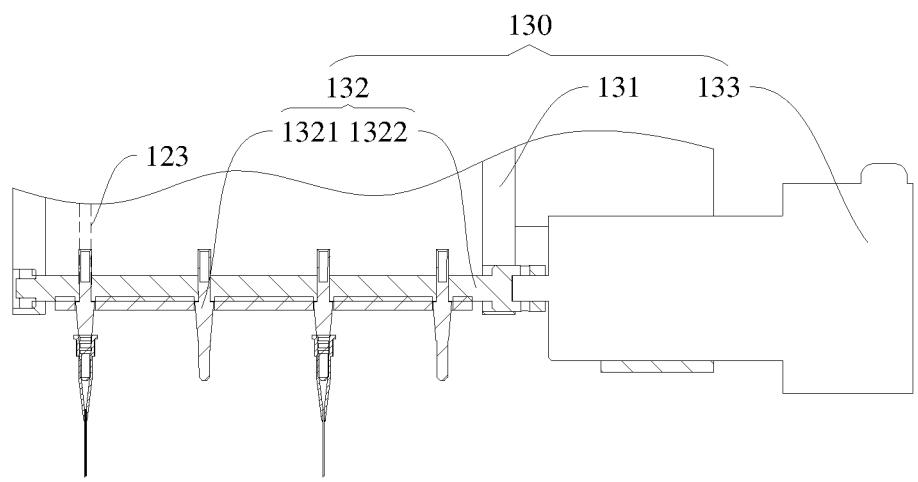
FIG. 30 is a schematic structural view of a motion controlling mechanism provided by an embodiment of the present application.
Figure 31:
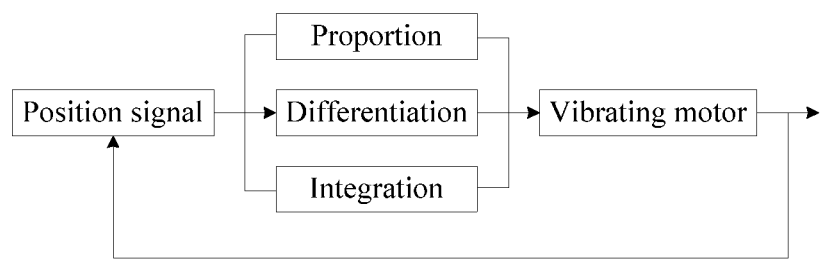
FIG. 31 shows a control principle of a closed-loop control of a motor provided by an embodiment of the present application.

As shown in FIG. 30, the motion controlling mechanism 130 provided by the present application includes a supporting frame 131, a connecting member 132, and a driving component. The connecting member 132 is configured to be connected to the liquid discharging nozzle 110. The driving component is fixed on the supporting frame 131 and connected to the connecting member 132 to drive the connecting member. The driving component drives the outlet end 112 of the liquid discharging nozzle 110 to vibrate with the displacement changing in the sine form or with the speed changing in the square wave form. The motion controlling mechanism 130 provided by the present application drives the outlet end 112 of the liquid discharging nozzle 110 to vibrate with the displacement changing in the sine form or with the speed changing in the square wave form, thus achieving the advantages of high generation efficiency of the microdroplets 199 and high uniformity. The motion controlling mechanism 130 provided by the present application be any other rotary driving device, such as oscillating cylinder, rotary magnet 137, etc.

In an embodiment of the present application, the driving component includes a vibrating motor 133. Preferably, the vibrating motor 133 is a galvanometer motor, of which an output shaft is connected to and drives the connecting member 132. The galvanometer motor can provide a stable reciprocating swing with a high speed and a stable reciprocating linear motion with a high speed, and the swinging range and frequency can be set according to needs, thereby significantly increasing the application range of the motion controlling mechanism 130 provided by the present application. Optionally, the rotary motor can also be a voice coil motor or a piezoelectric motor. Furthermore, the vibrating motor 133 is a motor adopting a closed-loop control for a vibration angle or position, and drives the output end of the liquid discharging nozzle 100 to vibrate, thereby accurately controlling the swing trajectory of the liquid discharging nozzle 100, and further reducing the interference from the environment and the system.

The application of the motor adopting the closed-loop control for the vibration angle or the position provided by the present application will be described with reference to FIG. 3 below. The motor adopting the closed-loop control for the vibration angle or the position includes components such as an infrared position sensor, a controlling circuit, a signal processing circuit, and so on. In an embodiment, the infrared position sensor is mounted on the rotary shaft of the motion controlling mechanism 130. The position signal acquired by the infrared position sensor is fed back to the controlling circuit. The controlling circuit processes the position feedback signal respectively via proportion calculation, integral operation, and differential operation in accordance with PID automatic control principle, thus the absolute position of the motion is accurately controlled by the motor by means of the controlling circuit combining with the signal processing circuit for the position feedforward, for the speed loop and for the current loop, and so on. The motor adopts the closed-loop control for the vibration angle or the position, thus avoiding the change of the vibration positions driven by the vibrating motor 133 in a case of a complex change of load environment, which is beneficial to the accurate control for the volume and the generation rate of the droplet 195 in projects.

In an embodiment of the present application, the connecting member 132 includes a connecting head 1321. The connecting head 1321 is connected to and drives the output shaft of the vibrating motor 133. The connecting head 1321 is in a hollow tubular shape. One end of the connecting head 1321 is configured to be connected to the liquid discharging nozzle 110, and the other end of the connecting head 1321 is configured to be connected to the liquid controlling mechanism of the liquid discharging nozzle 110. The first liquid 190 used to generate the microdroplet 199 is stored in the liquid discharging nozzle 110. The liquid controlling mechanism is used to discharge the first liquid 190 in the liquid discharging nozzle 110 at the preset flow rate in the generation process of the microdroplet 199. Under the control of the liquid controlling mechanism, the first liquid 190 stored in the liquid discharging nozzle 110 is discharged at a constant flow rate, or at a flow rate varied regularly, or at a flow rate of other forms. In this embodiment, under the control of the liquid controlling mechanism, the first liquid 190 in the liquid discharging nozzle 110 is discharged at the constant flow rate from the outlet end 112 of the liquid discharging nozzle 110. More specifically, the slim tube 123 of the liquid controlling mechanism is connected to the end of the connecting head 1321 away from the liquid discharging nozzle 110. The connecting head 1321 has both functions of communicating the liquid discharging nozzle 110 with the liquid controlling mechanism and driving the liquid discharging nozzle 110 to move. As an implementation manner, the connecting head 1321 is connected to and coaxial with the liquid discharging nozzle 110.

In order to facilitate the installation and the removal of the liquid discharging nozzle 110, the end of the connecting head 1321 proximate to the liquid discharging nozzle 110 has an outline in a shape of an inverted truncated cone, and the liquid discharging nozzle 110 is sleeved on the end of the connecting head 1321 in the shape of the inverted truncated cone. As the end of the connecting head 1321, which is proximate to the liquid discharging nozzle 110, has the outline in the shape of the inverted truncated cone, the resistance to the installation and the removal of the liquid discharging nozzle 110 can be reduced, moreover, the secure installation of the liquid discharging nozzle 110 is convenient. Furthermore, the connecting member 132 includes a connecting shaft 1322, which is rotatably disposed on the supporting frame 131. The connecting shaft 1322 is connected to and driven by the vibrating motor 133. The number of the connecting heads 1321 is plural. The plurality of connecting heads 1321 are fixed to the connecting shaft 1322 at intervals. As the plurality of connecting heads 1321 are mounted on one connecting shaft 1322 at intervals, the plurality of liquid discharging nozzles 110 can be simultaneously mounted corresponding to the plurality of connecting heads 1321, thereby significantly increasing the generation efficiency of the microdroplet 199.

Optionally, the rotatable arrangement of the connecting shaft 1322 on the supporting frame 131 includes rotatable connection of two ends of the connecting shaft 1322 to the supporting frame 131 and rotatable connection of another portion of the connecting shaft 1322 to the supporting frame 131. In an embodiment, the two ends of the connecting shaft 1322 are rotatably arranged on the supporting frame 131. One end of the connecting shaft 1322 is connected to and driven by the vibrating motor 133. The plurality of connecting heads 1321 are fixedly connected between the two ends of the connecting shaft 1322, and the two ends of the connecting shaft 1322 are rotatably arranged on the supporting frame, which is beneficial to the improvement of the rotation stability of the entire rotary shaft. As an implementation manner, the two ends of the connecting shaft 1322 are rotatably arranged on the supporting frame 131 via rolling bearings. In other embodiments, the other portion of the connecting shaft 1322 can also be rotatably arranged on the supporting frame 131 as long as the rotation and transmission requirements can be satisfied.

When the connecting head 1321 is fixed to the connecting shaft 1322, an angle between an axial direction of the connecting head 1321 and an axial direction of the connecting shaft 1322 can affect the moving trajectory and moving speed of the outlet end 112 of the liquid discharging nozzle 110. As an implementation manner, the axial direction of the connecting head 1321 is perpendicular to the axial direction of the connecting shaft 1322. The axial direction of the connecting head 1321 is kept perpendicular to the axial direction of the connecting shaft 1322, which is beneficial to the achievement of the vibration of the liquid discharging nozzle 110 by means of the rotation of the connecting shaft 1322. Furthermore, the plurality of connecting heads 1321 are arranged between the two ends of the connecting shaft 1322 at regular intervals. When the liquid discharging nozzles 110 arranged at regular intervals vibrate below the liquid surface of the second liquid 699, the second liquid 699 is uniformly disturbed, so as to ensure the same environment and conditions for the liquid discharging nozzles 110 to generate the corresponding microdroplets 199.

Figure 32:
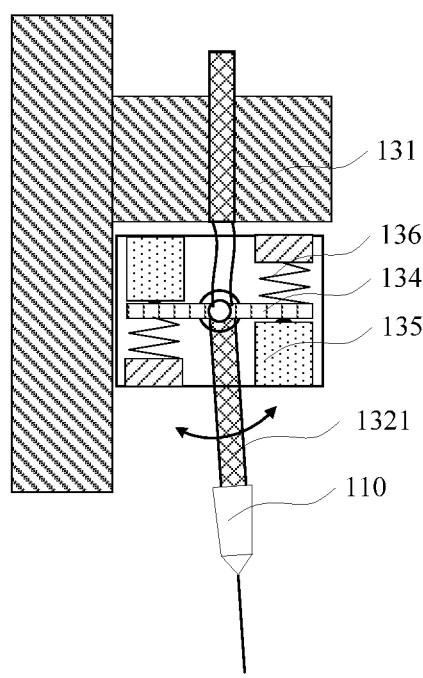
FIG. 32 is a schematic structural view of a piezoelectric motion controlling mechanism provided by an embodiment of the present application.

In an embodiment of the present application, the driving component includes a piezoelectric ceramic 135 and an elastic element 136. When the piezoelectric ceramic 135 is powered on and generates a deformation in a first direction, the connecting head 1321 of the connecting member 132 is driven to move in the first direction, and an elastic deformation of the elastic element 136 connected to the connecting member 132 is generated. When the piezoelectric ceramic 135 is powered on and generates a deformation in a direction opposite to the first direction, the elastic element 136 recovers from the elastic deformation, and meanwhile drives the connecting head 1321 of the connecting member 132 to move in the direction opposite to the first direction. Over and again, the connecting member 132 drives the outlet end 112 of the liquid discharging nozzle 110 to move with the displacement changing in the sine form or with the speed changing in the square wave form. As shown in FIG. 32, more specifically, the vibration of the outlet end 112 of the liquid discharging nozzle 110 along an arched trajectory with the displacement changing in the sine form or with the speed changing in the square wave form is achieved by means of a piezoelectric manner. The connecting head 1321 is rotatably arranged on the supporting frame 131 via a bearing. The liquid discharging nozzle 110 is sleeved on one end of the connecting head 1321 and is able to move along the arched trajectory centered around a bearing center. An extension plate 134 is symmetrically disposed at the position where the connecting head 1321 and the supporting frame 131 are rotatably connected, and an extension direction extension of the plate 134 is perpendicular to an extension direction of the connecting head 1321. The driving component includes the piezoelectric ceramic 135 and the elastic element 136 which work cooperatively to drive the connecting member 132. The extension plate 134 is driven by the piezoelectric ceramic 135 and the elastic element 136, thus achieving the fast vibration of the outlet end 112 of the liquid discharging nozzle 110. The piezoelectric manner has advantages of simple structure and stable driving property.

In an embodiment of the present application, the driving component includes an electromagnet 137, a magnetic element 138, and an elastic element 136. One end of the elastic element 136 is fixed to the supporting frame 131. The connecting member 132 is fixed to the other end of the elastic element 136. The magnetic element 138 is fixedly attached to the connecting head 1321 of the connecting member 132. When the electromagnet 137 is powered on, a magnetic force in the first direction is generated and exerted on the magnetic element 138; the magnetic element 138 and the connecting head 1321 of the connecting member 132 move in the first direction, meanwhile the elastic element 136 generates an elastic deformation. When the electromagnet 137 is powered off, the elastic element 136 drives the connecting head 1321 of the connecting member 132 and the magnetic element 138 to move in a direction opposite to the first direction. By means of controlling the electromagnet 137 to be powered on and off and via the connecting member 132, the magnetic element 138 drives the outlet end 112 of the liquid discharging nozzle 110 to move with the displacement changing in the sine form or with the speed changing in the square wave form.

Figure 33:
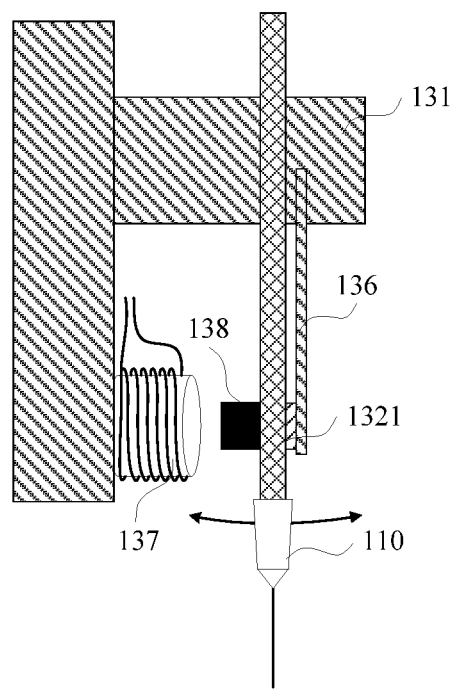
FIG. 33 is a schematic structural view of an electromagnet-elastic element-typed motion controlling mechanism provided by an embodiment of the present application.

More specifically, as shown in FIG. 33, the vibration of the outlet end 112 of the liquid discharging nozzle 110 along an arched trajectory with the displacement changing in the sine form or with the speed changing in the square wave form is achieved by means of an electromagnetic manner. In this embodiment, the moving trajectory of the outlet end 112 of the liquid discharging nozzle 110 is a curved line approximate to be a horizontal line. One end of the elastic element 136 is fixed on the supporting frame 131. The other end of the elastic element 136 is fixedly connected to the connecting head 1321. The liquid discharging nozzle 110 is sleeved on one end of the connecting head 1321. The driving component includes the electromagnet 137 and the magnetic element 138. The magnetic element 138 is fixedly connected to the connecting member 132. The electromagnet 137 drives the connecting member 132 via the connecting member 132 and is fixedly arranged on the supporting frame 131. The magnetic element 138 which can be attracted by the electromagnet 137 is fixedly disposed at the connecting head 1321 and keeps in a range of a working distance from the electromagnet 137. The position sensor can detect the position of the magnetic element 138 in moving, and based on the detected position of the magnetic element, the position of the outlet end 112 of the liquid discharging nozzle 110 can be calculated. When the electromagnet 137 is powered on, it attracts the magnetic element 138 and drives the liquid discharging nozzle 110 to move in a direction coming close to the electromagnet 137, while the elastic element 136 stores energy due to the elastic deformation. The electromagnet 137 is powered off when the outlet end 112 of the liquid discharging nozzle 110 moving close to the electromagnet 137 arrives at a first preset position. Because of the resilience of the elastic element 136, the liquid discharging nozzle 110 moves away from the electromagnet 137. The electromagnet 137 is powered on when the outlet end 112 of the liquid discharging nozzle 110 moving away from the electromagnet 137 arrives at a second preset position. Then the electromagnet 137 attracts the magnetic element 138 to drive the liquid discharging nozzle 110 to move in the direction coming close to the electromagnet 137, while the elastic element 136 stores energy due to the elastic deformation. Such cycling is repeated. The working parameters of the electromagnet 137 and the elasticity modulus of the elastic element 136 can be adjusted according to specific operation conditions, so as to achieve the vibration of the outlet end 112 of the liquid discharging nozzle 110 with the displacement changing in the sine form or the speed changing in the square wave form. As an implementation manner, the elastic element 136 includes an elastic steel sheet or any other elastic element 136 satisfying the elastic requirements.

Figure 34:
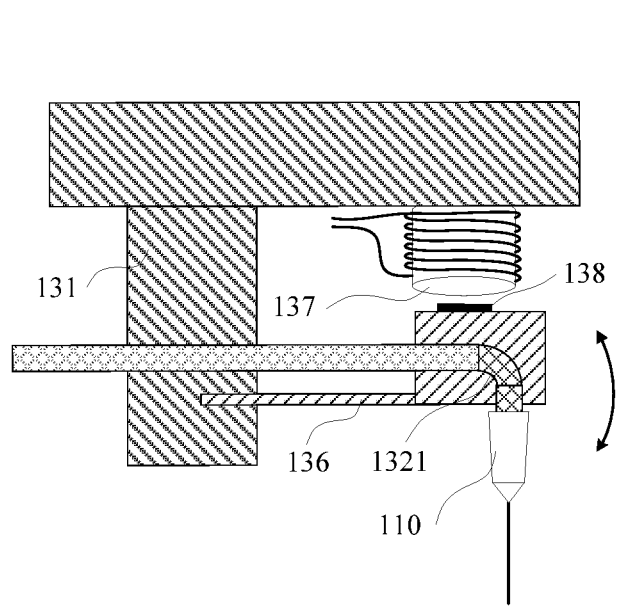
FIG. 34 is a schematic structural view of an electromagnet-elastic element-typed motion controlling mechanism provided by another embodiment of the present application.

As shown in FIG. 34, in an embodiment of the present application, the vibration of the outlet end 112 of the liquid discharging nozzle 110 along the arched trajectory with the displacement changing in the sine form or with the speed changing in the square wave form is achieved by means of an electromagnetic manner. In this embodiment, the moving trajectory of the outlet end 112 of the liquid discharging nozzle 110 is a curved line approximate to be a vertical line. One end of the elastic element 136 is fixed on the supporting frame 131. The other end of the elastic element 136 is fixedly connected to the connecting head 1321. The liquid discharging nozzle 110 is sleeved on one end of the connecting head 1321. The electromagnet 137 is fixedly arranged on the supporting frame 131. The magnetic element 138, which can be attracted by the electromagnet 137, is fixedly attached to the connecting head 1321 and keeps in a range of a working distance from the electromagnet 137. The position sensor is capable of detecting the position of the magnetic element 138 in moving, and based on the detected position of the magnetic element, the position of the outlet end 112 of the liquid discharging nozzle 110 is calculated. When the electromagnet 137 is powered on, it attracts the magnetic element 138 to drive the liquid discharging nozzle 110 to move in a direction coming close to the electromagnet 137, while the elastic element 136 stores energy due to the elastic deformation. The electromagnet 137 is powered off when the outlet end 112 of the liquid discharging nozzle 110 moving close to the electromagnet 137 arrives at the first preset position. Because of the resilience of the elastic element 136, the liquid discharging nozzle 110 moves away from the electromagnet 137. The electromagnet 137 is powered on when the outlet end 112 of the liquid discharging nozzle 110 moving away from the electromagnet 137 arrives at the second preset position. Then the electromagnet 137 attracts the magnetic element 138 to drive the liquid discharging nozzle 110 to move in the direction coming close to the electromagnet 137, while the elastic element 136 stores energy due to the elastic deformation. Such cycling is repeated. The working parameters of the electromagnet 137 and the elasticity modulus of the elastic element 136 can be adjusted according to specific operation conditions, so as to achieve the vibration of the outlet end 112 of the liquid discharging nozzle 110 with the displacement changing in the sine form or the speed changing in the square wave form. As an implementation manner, the elastic element 136 includes an elastic steel sheet or any other elastic element 136 satisfying the elastic requirements.

In an embodiment of the present application, the driving component includes an electromagnet 137 and a magnetic element 138. The magnetic element 138 is fixedly connected to the connecting head 1321 of the connecting member 132. The electromagnet 137 generates a varying magnetic field in which the magnetic element 138 moves. By means of the connecting member 132, the magnetic element 138 drives the outlet end 112 of the liquid discharging nozzle 110 to move with the displacement changing in the sine form or to move with the speed changing in the square wave form.

Figure 35:
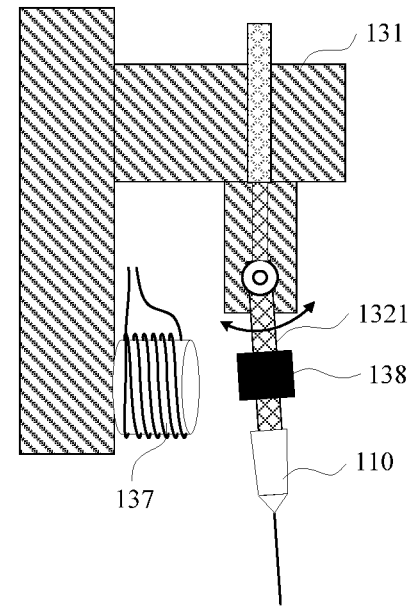
FIG. 35 is a schematic structural view of an electromagnet-bearing-typed motion controlling mechanism provided by an embodiment of the present application.

Furthermore, as shown in FIG. 35, the vibration of the outlet end 112 of the liquid discharging nozzle 110 along an arched trajectory with the displacement changing in the sine form or with the speed changing in the square wave form is achieved by means of the electromagnet 137. The connecting head 1321 is rotatably arranged on the supporting frame 131 via a bearing. The liquid discharging nozzle 110 is sleeved on one end of the connecting head 1321. The electromagnet 137 is fixedly arranged on the supporting frame 131. The magnetic element 138 which can be attracted by the electromagnet 137 is fixedly attached to the connecting head 1321 and keeps in a range of a working distance from the electromagnet 137. The position sensor can detect the rotation angle of the connecting head 1321, and based on the detected the rotation angle, the position of the outlet end 112 of the liquid discharging nozzle 110 is calculated. When the electromagnet 137 is powered on, it attracts the magnetic element 138 to drive the liquid discharging nozzle 110 to move in the direction coming close to the electromagnet 137. A direction of the current flows through the electromagnet 137 is reversed when the outlet end 112 of the liquid discharging nozzle 110 moving close to the electromagnet 137 arrives at the first preset position. Under the opposite force exerted by the electromagnet 137, the liquid discharging nozzle 110 moves away from the electromagnet 137. The direction of the current flows through the electromagnet 137 is reversed again when the outlet end 112 of the liquid discharging nozzle 110 moving away from the electromagnet 137 arrives at the second preset position. Then the electromagnet 137 attracts the magnetic element 138 to drive the liquid discharging nozzle 110 to move in the direction coming close to the electromagnet 137. Such cycling is repeated. The working parameters of the electromagnet 137 can be adjusted according to specific operation conditions, so as to achieve the vibration of the outlet end 112 of the liquid discharging nozzle 110 with the displacement changing in the sine form or with the speed changing in the square wave form.

In the above-described embodiments, the output of the vibrating motor 133 drives the outlet end 112 of the liquid discharging nozzle 110 to vibrate along the arched trajectory with the displacement changing in the sine form or with the speed changing in the square wave form. In other embodiments, the outlet end 112 of the liquid discharging nozzle 110 can also vibrates along a linear trajectory with the displacement changing in the sine form or with the speed changing in the square wave form.

Figure 36:
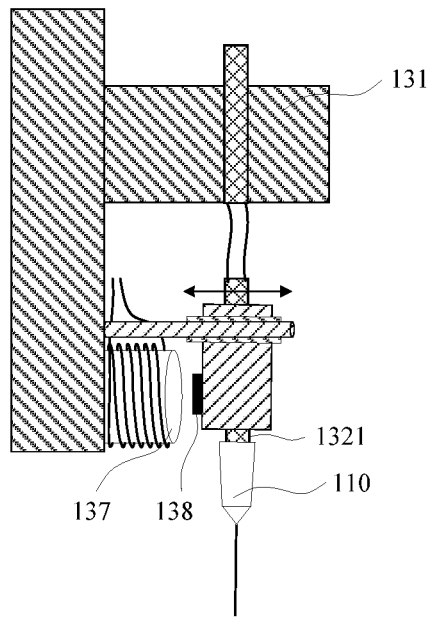
FIG. 36 is a schematic structural view of an electromagnet-bearing-typed motion controlling mechanism provided by another embodiment of the present application.

As shown in FIG. 36, in an embodiment of the present application, the vibration of the outlet end 112 of the liquid discharging nozzle 110 along a linear trajectory with the displacement changing in the sine form or with the speed changing in the square wave form is achieved by means of the electromagnet 137. In this embodiment, the outlet end 112 of the liquid discharging nozzle 110 vibrates along a linear trajectory in a horizontal plane. The connecting head 1321 is slidably arranged on the supporting frame 131 via a linear bearing. The liquid discharging nozzle 110 is sleeved on one end of the connecting head 1321. The electromagnet 137 is fixedly arranged on the supporting frame 131. The magnetic element 138 which can be attracted by the electromagnet 137 is fixedly attached to the connecting head 1321 and keeps in a range of a working distance from the electromagnet 137. The position sensor can detect the position of the connecting head 1321 in sliding, and based on the detected position, the position of the outlet end 112 of the liquid discharging nozzle 110 is calculated. When the electromagnet 137 is powered on, it attracts the magnetic element 138 to drive the liquid discharging nozzle 110 to slide in a direction coming close to the electromagnet 137. A direction of the current flows through the electromagnet 137 is reversed when the outlet end 112 of the liquid discharging nozzle 110 moving close to the electromagnet 137 arrives at the first preset position. Under the opposite force exerted by the electromagnet 137, the liquid discharging nozzle 110 slides away from the electromagnet 137. The direction of the current flows through the electromagnet 137 is reversed again when the outlet end 112 of the liquid discharging nozzle 110 moving away from the electromagnet 137 arrives at the second preset position. Then the electromagnet 137 attracts the magnetic element 138 to drive the liquid discharging nozzle 110 to slide in the direction coming close to the electromagnet 137. Such cycling is repeated. The working parameters of the electromagnet 137 can be adjusted according to specific operation conditions, so as to achieve the vibration of the outlet end 112 of the liquid discharging nozzle 110 with the displacement changing in the sine form or with the speed changing in the square wave form.

Figure 37:
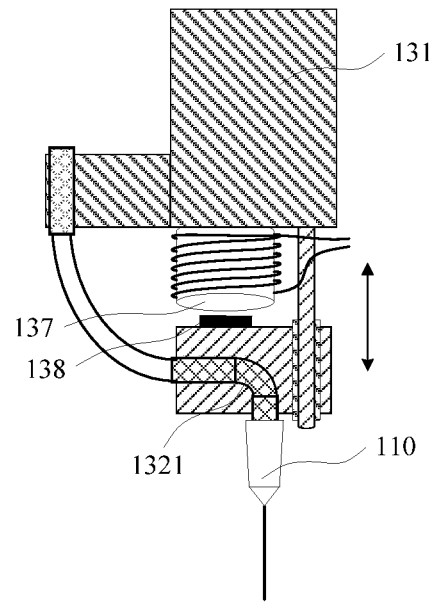
FIG. 37 is a schematic structural view of an electromagnet-bearing-typed motion controlling mechanism provided by yet another embodiment of the present application.

As shown in FIG. 37, in an embodiment of the present application, the vibration of the outlet end 112 of the liquid discharging nozzle 110 along a linear trajectory with the displacement changing in the sine form or with the speed changing in the square wave form is achieved by means of the electromagnet 137. In this embodiment, the outlet end 112 of the liquid discharging nozzle 110 vibrates along the linear trajectory within a vertical plane. The connecting head 1321 is slidably arranged on the supporting frame 131 via the linear bearing. The liquid discharging nozzle 110 is sleeved on one end of the connecting head 1321. The electromagnet 137 is fixedly arranged on the supporting frame 131. The magnetic element 138 which can be attracted by the electromagnet 137 is fixedly attached to the connecting head 1321 and keeps in a range of a working distance from the electromagnet 137. The position sensor can detect the position of the connecting head 1321 in sliding, and based on the detected position, the position of the outlet end 112 of the liquid discharging nozzle 110 is calculated. When the electromagnet 137 is powered on, it attracts the magnetic element 138 to drive the liquid discharging nozzle 110 to slide in a direction coming close to the electromagnet 137. The direction of the current flows through the electromagnet 137 is reversed when the outlet end 112 of the liquid discharging nozzle 110 moving close to the electromagnet 137 arrives at the first preset position. Under the opposite force exerted by the electromagnet 137, the liquid discharging nozzle 110 slides away from the electromagnet 137. The direction of the current flows through the electromagnet 137 is reversed again when the outlet end 112 of the liquid discharging nozzle 110 moving away from the electromagnet 137 arrives at the second preset position. Then the electromagnet 137 attracts the magnetic element 138 to drive the liquid discharging nozzle 110 to slide in the direction coming close to the electromagnet 137. Such cycling is repeated. The working parameters of the electromagnet 137 can be adjusted according to specific operation conditions, so as to achieve the vibration of the outlet end 112 of the liquid discharging nozzle 110 with the displacement changing in the sine form or with the speed changing in the square wave form.

The galvanometer motor can output a reciprocating linear motion. In other embodiments of the present application, the galvanometer motor drives the outlet end 112 of the liquid discharging nozzle 110 to move along the linear trajectory with the displacement changing in the sine form or with the speed changing in the square wave form.

The galvanometer motor can output a reciprocating linear motion. In other embodiments of the present application, the galvanometer motor drives the outlet end 112 of the liquid discharging nozzle 110 to move along the linear trajectory with the displacement changing in the sine form or with the speed changing in the square wave form.

The microdroplet generating device and method provided by the present application can be widely applied to such application fields as medical clinical test, preparation of nano-material, food and environment detections, biochemical analysis, and so on. In a specific application scenario, the generating device and the generating method for the microdroplet 199 provided by the present application is applied to a polymerase chain reaction (PCR).

To solve the problem that the volume sizes of the microdroplets generated by the conventional liquid driving mechanism and by using the conventional liquid driving method are random for the reason that the flow rate of the liquid discharged from the liquid discharging nozzle in a moving state is unstable and uncontrollable, it is necessary to provide a liquid driving mechanism and a liquid driving method enabling liquid to be discharged from the liquid discharging nozzleat a preset flow rate.

As shown in FIGS. 38-43, a liquid driving mechanism 120 provided by the present application is configured to control a flow rate and a flow quantity of a third liquid 820 discharged from the outlet end of the liquid discharging nozzle 830 in the process of generating microdroplets by means of a microdroplet generating system. The liquid driving mechanism 120 provided by the present application includes a housing 100, a first volume-variable assembly 200, and a linear motor assembly 300. The housing 100 of the liquid driving mechanism 120 is further configured to provide a support. The first volume-variable assembly 200 is the executing unit in the process of driving liquid. The linear motor assembly 300 is the driving unit in the process of driving liquid. The first volume-variable assembly 200 and the linear motor assembly 300 both are mounted in the housing 100. The first volume-variable assembly 200 includes a first syringe barrel 201 and a first push rod 202. An outer wall of the first syringe barrel 201 is fixed at an inner wall of the housing 100. The first push rod 202 is slidably coupled with an inner wall of the first syringe barrel 201, namely, the first push rod 202 is slidably mounted in the first syringe barrel 201. The first syringe barrel 201 can store a first driving liquid 810 therein and has a liquid inlet/outlet which communicates with an inlet end of the first liquid discharging nozzle 830. A third liquid 820 is stored in the first liquid discharging nozzle 830. An output end of the linear motor assembly 300 is connected to the first push rod 202 and configured to drive the first push rod 202 to slide in an extension direction of the first syringe barrel 201. In the generation process of the microdroplet, the output end of the linear motor assembly 300 drives the first push rod 202 to press the first driving liquid 810 stored in the first syringe barrel 201. The pressed first driving liquid 810 in turn presses the third liquid 820 stored in the first liquid discharging nozzle 830, thereby finally discharging the third liquid 820 from the outlet end of the first liquid discharging nozzle 830. The flow rate and the flow quantity of the third liquid 820 discharged from the first liquid discharging nozzle 830 is dependent on the moving state of the output end of the linear motor assembly 300.

The liquid driving mechanism 120 described above takes advantage of the incompressibility of first driving liquid 810, thereby ensuring that the third liquid 820 is able to be discharged from the outlet end of the first liquid discharging nozzle 830 at a preset flow rate and with a preset flow quantity, even though the outlet end of the first liquid discharging nozzle 830 vibrates at a high frequency. The linear motor assembly 300 not only has higher motion accuracy, but also enables the magnitude of the current to be adjusted conveniently according to the actual operation conditions such as the liquid discharging speed, the liquid discharging pressure, and so on, thereby ensuring that the first push rod 202 can slide at a preset speed or slides for a preset distance, and allowing the third liquid 820 to be discharged from the outlet end of the first liquid discharging nozzle 830 accurately at the preset flow rate and with the preset flow quantity. The volume of the generated microdroplet can be accurately controlled via the liquid driving mechanism 120 provided by the present application.

Figure 41:
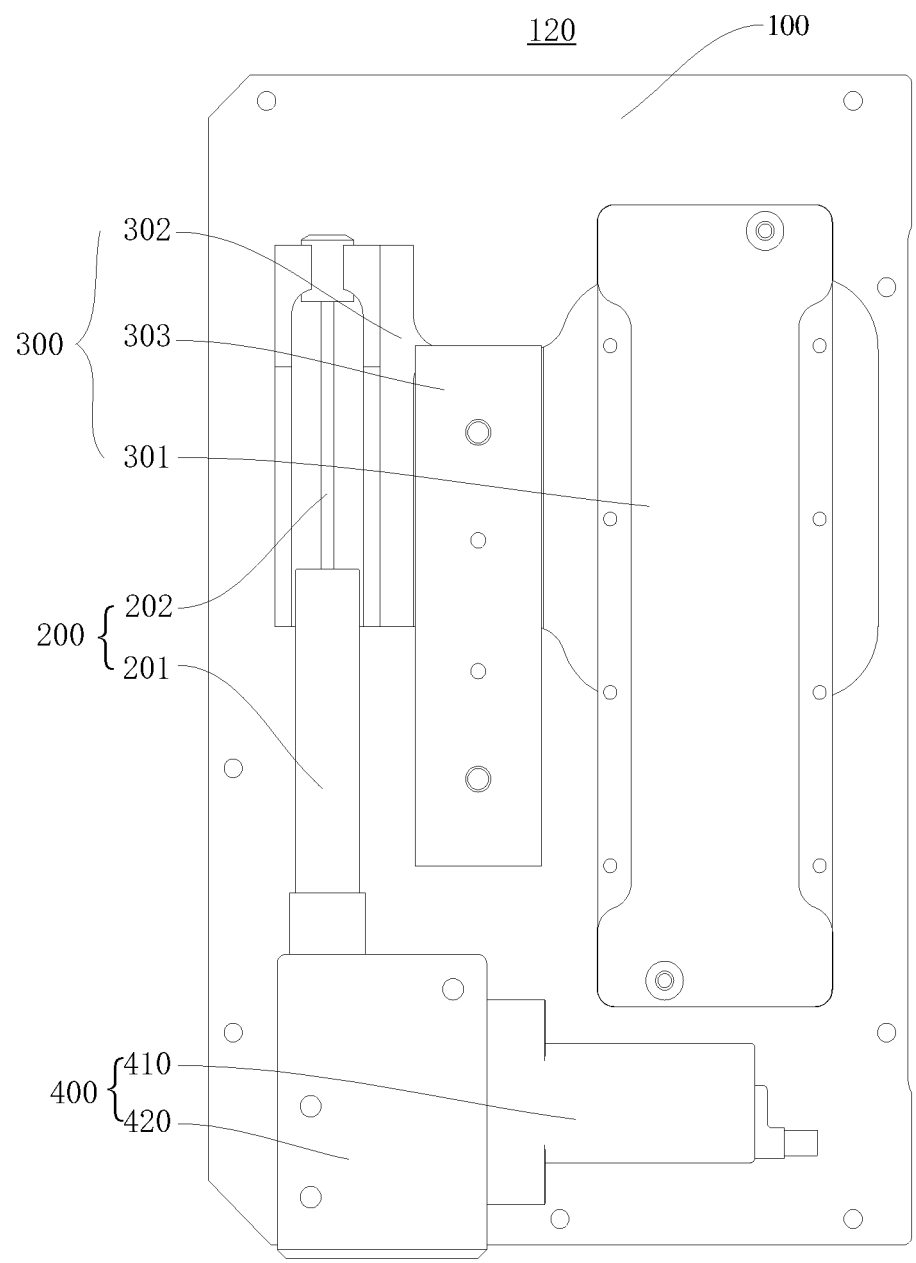
FIG. 41 is a schematic back view of partial structure of the liquid driving mechanism provided by an embodiment of the present application.
Figure 42:
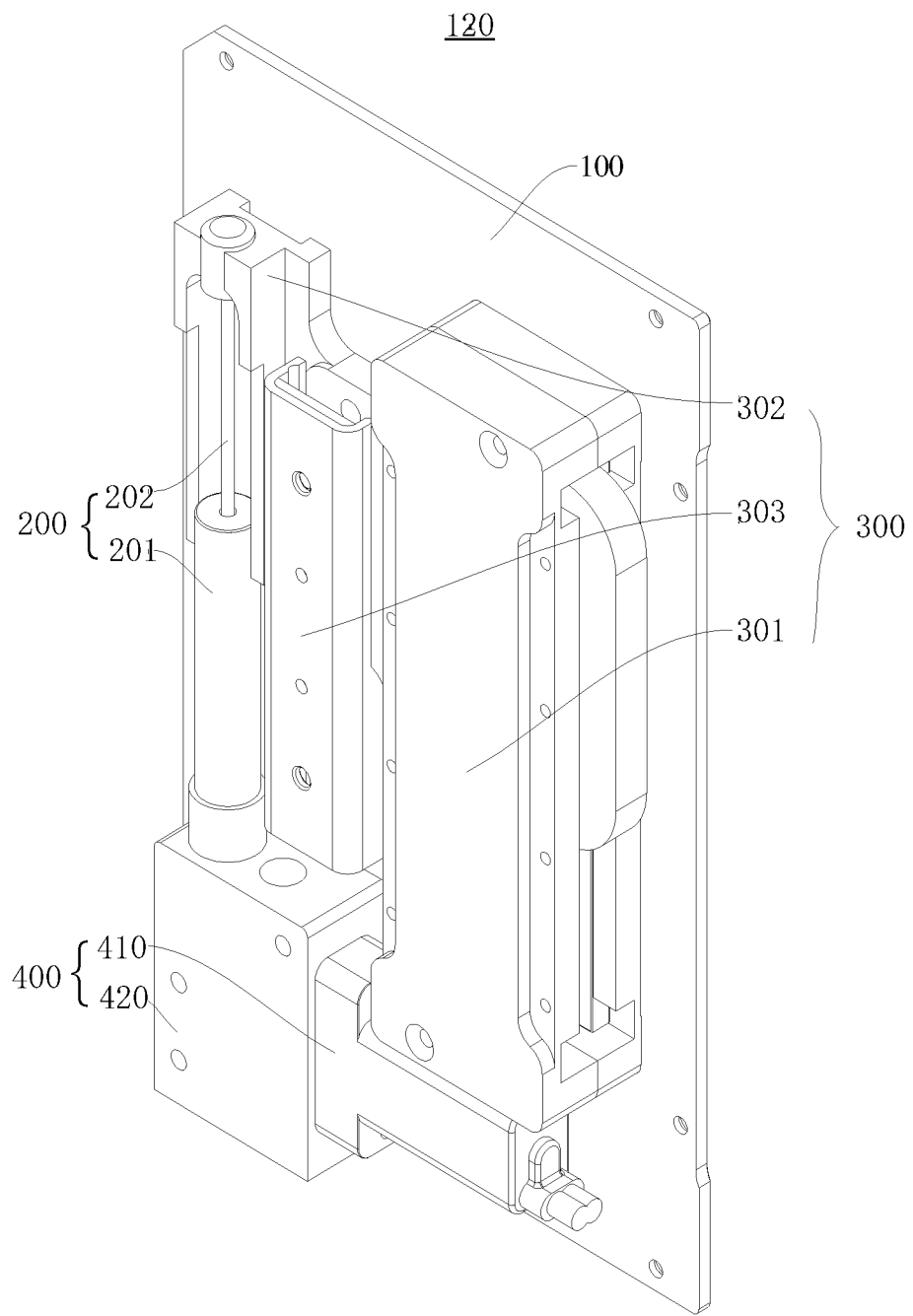
FIG. 42 is a second schematic side view of partial structure of the liquid driving mechanism provided by an embodiment of the present application.

The first syringe barrel 201 in the present application can be in a shape of straight tube or a bent shape. The liquid inlet/outlet on the first syringe barrel 201 can be disposed at one end or at a central position of the first syringe barrel 201. The specific structures of the first syringe barrel 201 and the first push rod 202 and the specific location relationship therebetween are not limited in the present application. For illustration purposes, as shown in FIGS. 41 and 42, taking the first syringe barrel 201 in the shape of the straight tube and having the liquid inlet/outlet disposed at one end thereof for an example, the first push rod 202 slidably mounted in the first syringe barrel 201 passes through the other end of the first syringe barrel 201. In other embodiments of the present application, the first volume-variable assembly 200 also can be any other structure capable of achieving volume variations.

In an embodiment of the present application, as shown in FIGS. 38 to 43, the linear motor assembly 300 includes a voice coil motor 301. A primary section 311 of the voice coil motor 301 is fixedly mounted on the inner wall of the housing 100. A secondary section 312 of the voice coil motor 301 is fixedly connected to the first push rod 202 in the sliding direction of the first push rod 202. The voice coil motor 301 has advantages of not only fast response, high speed, and high acceleration value, but also simple structure, small volume, and convenience of control. The secondary section 312 of the voice coil motor 301 can maintains a preset sliding speed by means of controlling the magnitude of the current, even though the resistance to a sliding motion is increasing or decreasing, therefore, the preset liquid discharging flow rate can be conveniently maintained even though the liquid discharging pressure of the third liquid 820 is changing. The voice coil motor 301 can also operate in a mode of a preset sliding position, a mode of a preset sliding speed, a mode of a preset driving pressure value and the like according to the actual operation conditions. Accordingly, executed by the first volume-variable assembly 200, the third liquid 820 can be accurately discharged from the first liquid discharging nozzle 830 with a preset volume, at a preset flow rate, or with a preset discharging pressure, etc.

Figure 39:
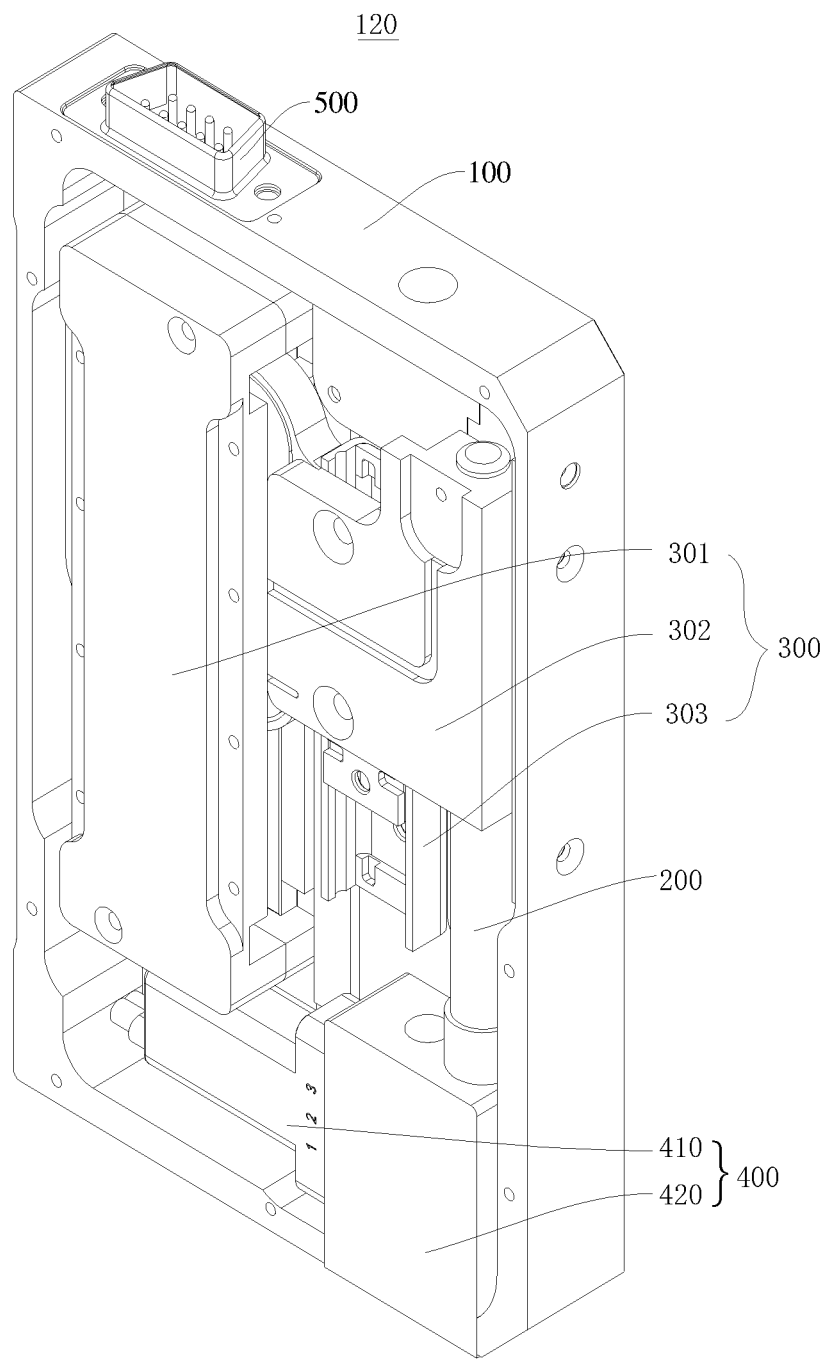
FIG. 39 is a first schematic side view of partial structure of the liquid driving mechanism provided by an embodiment of the present application.
Figure 40:
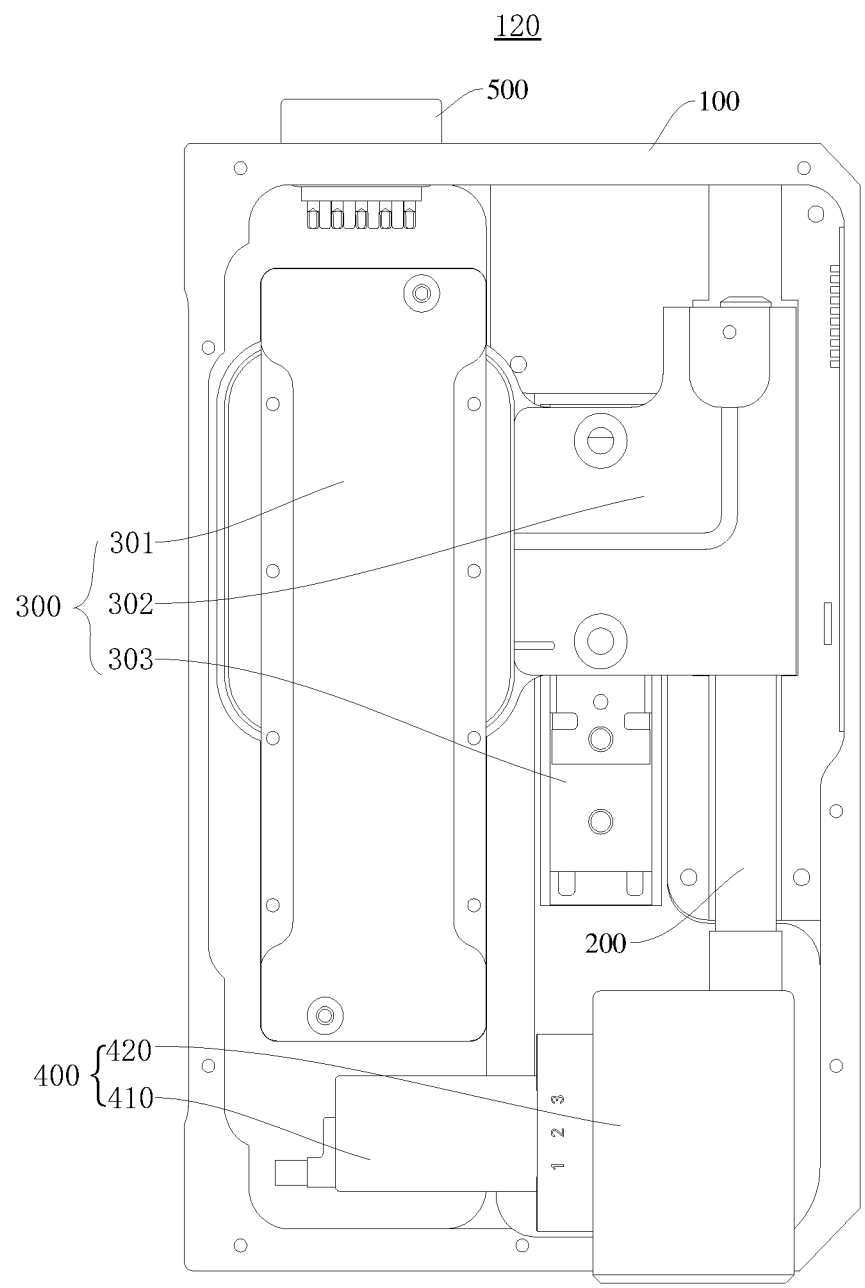
FIG. 40 is a schematic front view of partial structure of the liquid driving mechanism provided by an embodiment of the present application.

Furthermore, as shown in FIGS. 39 to 40, the voice coil motor 301 is disposed at a side of the first syringe barrel 201. The sliding direction of the secondary section 312 in the voice coil motor 301 is parallel to the sliding direction of the first push rod 202 sliding in the first syringe barrel 201. The secondary section 312 of the voice coil motor 301 is connected to and drives the first push rod 202. The voice coil motor 301 is arranged at the side of the first syringe barrel 201, thereby reducing the dimension of the liquid driving mechanism 120 in the extension direction of the first syringe barrel 201. The sliding direction of the secondary section 312 sliding in the voice coil motor 301 is the same as the sliding direction of the first push rod 202, thus the connection manner between the secondary section 312 of the voice coil motor 301 and the first push rod 202 can be simplified. As an implementation manner, as shown in FIGS. 39 to 42, the linear motor assembly 300 further includes a connecting plate 302. One end of the connecting plate 302 is fixedly connected to the secondary section 312 of the voice coil motor 301, and the other end of the connecting plate 302 is fixedly connected to an end of the first push rod 202, which is located outside of the first syringe barrel 201. It should be understood that the connecting plate 302 is movably disposed in the housing 100 and synchronously slides with the secondary section 312 of the voice coil motor 301, so that the secondary section 312 of the voice coil motor 301 can drive the first push rod 202 to synchronously slide in the first syringe barrel 201 via the connecting plate 302. In other embodiments, the sliding direction of the secondary section 312 sliding in the voice coil motor 301 can also be coaxial with or perpendicular to the sliding direction of the first push rod 202 or arranged in other achievable manner.

Yet furthermore, as shown in FIGS. 42 to 47, the secondary section 312 of the voice coil motor 301 includes a frame 3121 and a coil 3122. The coil 3122 is wound on the skeleton 3121. The frame 3121 and the connecting plate 302 are integrally formed. The frame 3121 and the connecting plate 302 are integrally formed, thus the action error between the secondary section 312 of the voice coil motor 301 and the first push rod 202 is further obviated, thereby ensuring the precision of the synchronous motion of the first push rod 202 and the secondary section 312 of the voice coil motor 301. In other embodiments, the connection between the secondary section 312 of the voice coil motor 301 and the connecting plate 302 can also be a rigid connection achieved by a connecting element such as a screw or a clamping element. The connection manner between the secondary section 312 of the voice coil motor 301 and the connecting plate 302 is not limited herein, as long as the secondary section 312 of the voice coil motor 301 can drive the first push rod 202 to synchronously move via the connecting plate 302.

In an embodiment of the present application, as shown in FIGS. 40 and 42, the linear motor assembly 300 further includes a guiding element 303 including a guide rail and a sliding block. The guide rail is fixedly disposed in the housing 100, and an extension direction of the guide rail is parallel to the sliding direction of the first push rod 202. The sliding block is slidably disposed on the guide rail and fixedly connected to the connecting plate 302. The guiding element 303 has a guiding function in the sliding process of the connecting plate 302, so as to ensure that, driven by the secondary section 312 of the voice coil motor 301 via the connecting plate 302, the first push rod 202 slides stably and synchronously, thereby accurately controlling the third liquid 820 to be discharged from the first liquid discharging nozzle 830 at the preset flow rate or with the preset flow quantity. Furthermore, the linear motor assembly 300 further includes a displacement sensor disposed in the housing 100 and electrically connected to the voice coil motor 301. The displacement sensor is configured to detect positions, sliding speeds, and the like of the secondary section 312, the connecting plate 302, and the first push rod 202 which are sliding synchronously. The displacement sensor is electrically connected to the voice coil motor 301 to achieve a closed-loop control of the voice coil motor 301. Optionally, the above displacement sensor includes a displacement sensor of optical grating type, magnetic grating type, resistance type, or linear variable differential transformer (LVDT) type etc. More specifically, the displacement sensor is a photoelectric linear displacement sensor. In other embodiments of the present application, the voice coil motor 301 itself is a servo motor. The closed-loop control system of the voice coil motor 301 is integrated inside the voice coil motor 301, thereby further reducing the volume of the liquid driving mechanism 120 provided by the present application.

In an embodiment of the present application, as shown in FIGS. 42 to 45, the voice coil motor 301 includes the primary section 311 and the secondary section 312. The primary section 311 includes a first pair of magnets 3111 and a second pair of magnets 3112. The first pair of magnets 3111 and the second pair of magnets 3112 are provided in sequence in a sliding direction of the secondary section 312 in the housing 100. Different magnetic poles of two magnets of the first pair of magnets 3111 are arranged opposite to each other. Different magnetic poles of two magnets of the second pair of magnets 3112 are arranged opposite to each other. A direction of magnetic induction lines between the first pair of magnets 3111 is opposite to a direction of magnetic induction lines between the second pair of magnets 3112. The secondary section 312 includes the frame 3121 and the coil 3122 wound on the frame 3121. The coil 3122 has a first segment 3125 and a second segment 3126 which, after being powered on, have opposite current directions. When the secondary section 312 slides, the first segment 3125 of the coil 3122 slides between the first pair of magnets 3111, and the second segment 3126 of the coil 3122 slides between the second pair of magnets 3112. The two pairs of magnets and the coil 3122 can simultaneously generate induction forces having the same direction and the same magnitude on the first segment 3125 and the second segment 3126 of the coil 3122, which enables the secondary section 312 in the voice coil motor 301 to act fast, and improves the sensitivity of the voice coil motor 301.

Figure 43:
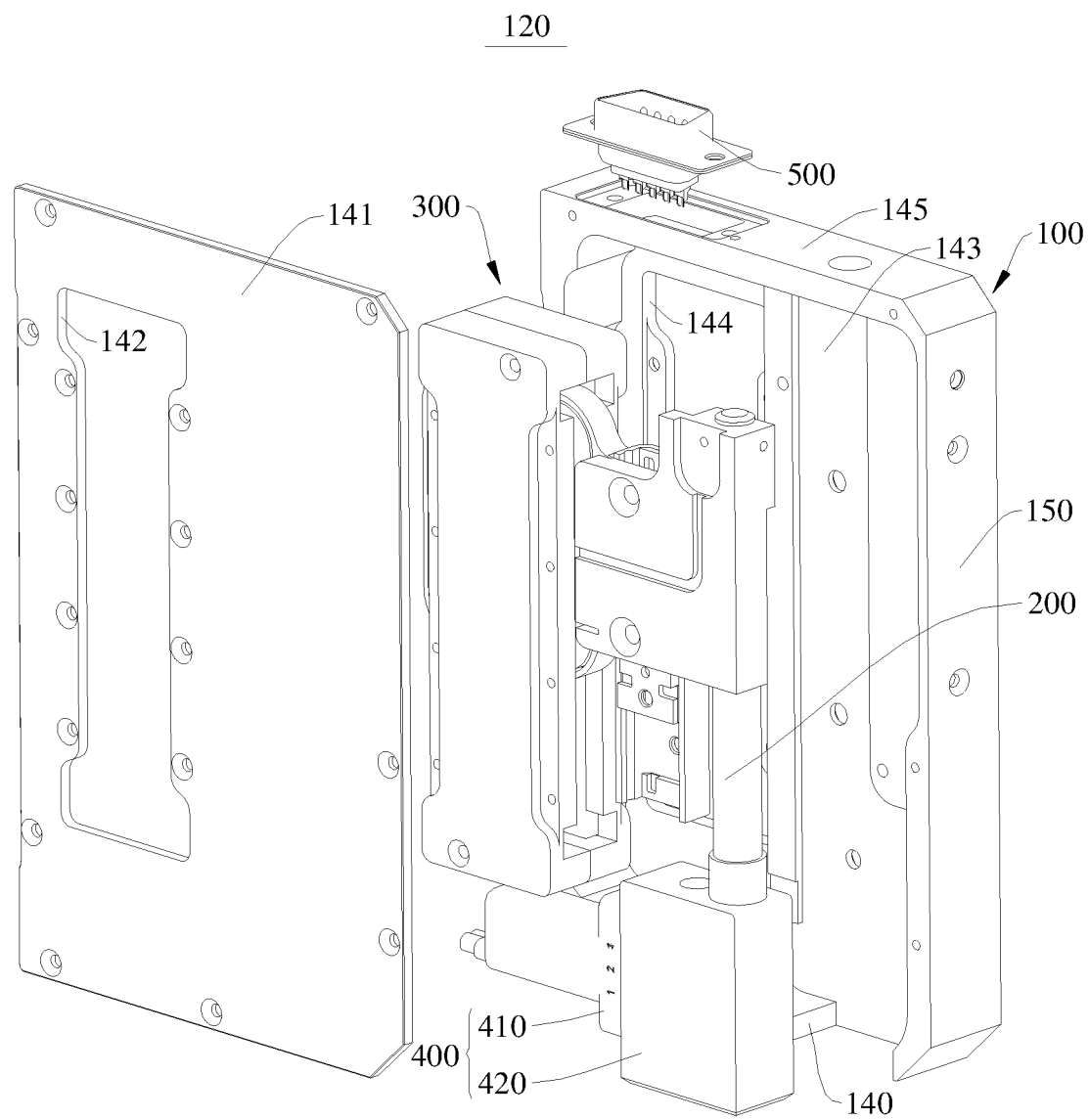
FIG. 43 is a schematic exploded view of an assembly of the liquid driving mechanism provided by an embodiment of the present application.
Figure 44:
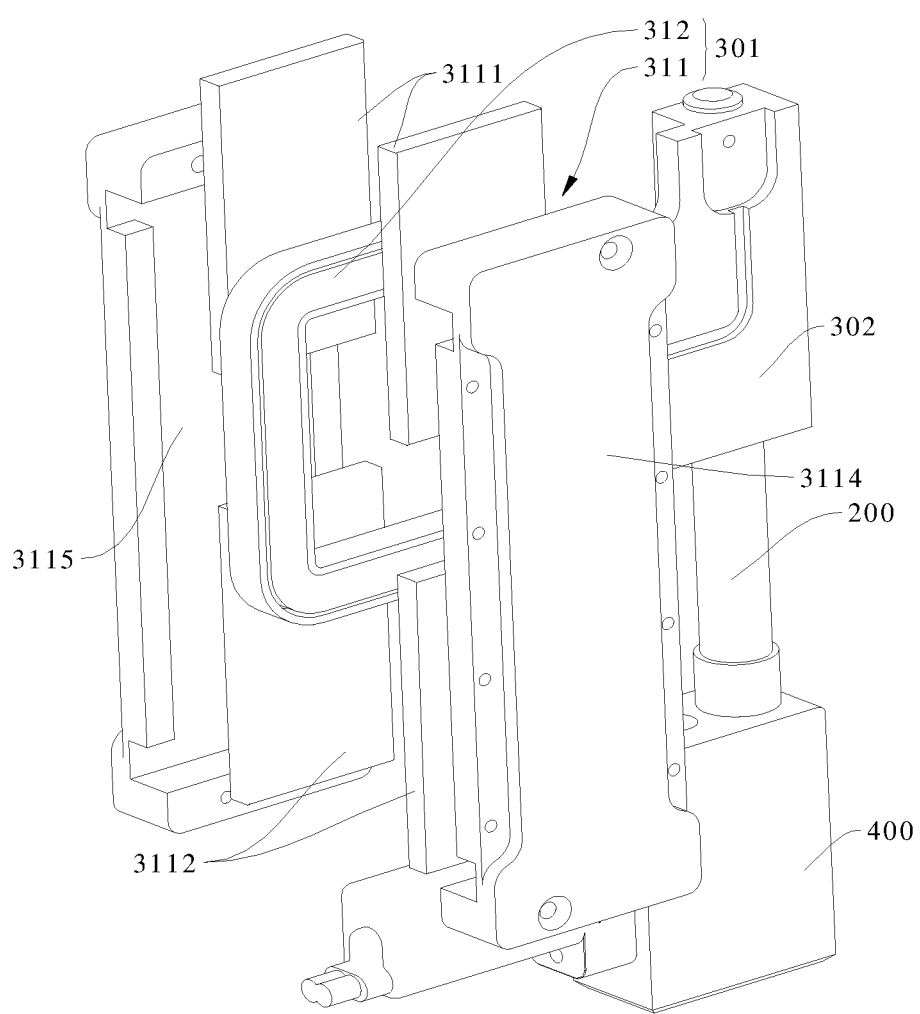
FIG. 44 is a schematic exploded view of an assembly of a voice coil motor, a connecting plate, and a first volume-variable assembly provided by an embodiment of the present application.
Figure 45:
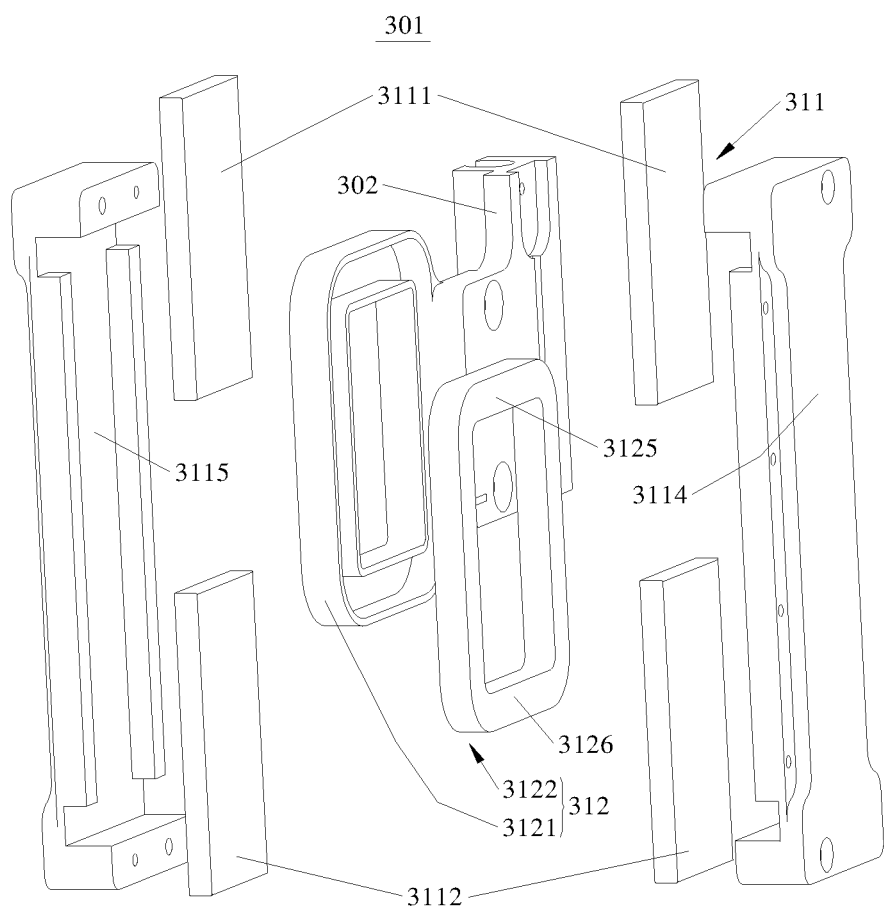
FIG. 45 is a schematic exploded view of an assembly of a voice coil motor and a connecting plate provided by an embodiment of the present application.

As an implementation manner, as shown in FIGS. 43 to 45, the first pair of magnets 3111 and the second pair of magnets 3112 all are magnets in the shape of rectangular plate. The first pair of magnets 3111 and the second pair of magnets 3112 all are fixedly mounted on the inner wall of the housing 100. One end of the first pair of magnets 3111 is abutted against one end of the second pair of magnets 3112 in the sliding direction of the secondary section 312 of the voice coil motor 301. The frame 3121 is hollow and in the shape of a rectangle with rounded corners. An annular groove in the shape of a rectangle with rounded corners is provided on one end surface of the frame 3121, and the coil 3122, which is also hollow and in the shape of a rectangle with rounded corners, is fixedly mounted in the annular groove of the frame 3121. When a current flows through the coil 3122, the first segment 3125 and the second segment 3126 simultaneously generate induction forces with the same direction and the same magnitude. Since the first pair of magnets 3111 and the second pair of magnets 3112 are all fixed, the coil 3122, through which the current flows, slides in the direction of the induction forces, and the frame 3121 attached to the coil 3122 synchronously moves together with the coil 3122. Accordingly, the secondary section 312 of the voice coil motor 301 drives the first push rod 202 to synchronously move via the connecting plate 302. When the displacement sensor detects out that the connecting plate 302 which synchronously slides with the first push rod 202 slides to a preset position, the displacement sensor sends a signal, then the voice coil motor 301 is powered off, and the secondary section 312 of the voice coil motor 301 stops sliding. Alternatively, when the displacement sensor detects out that the sliding speed of the connecting plate 302 which synchronously slides with the first push rod 202 fluctuates slightly, the displacement sensor sends signal, and the current flows through the voice coil motor 301 is accordingly adjusted, so as to ensure that the secondary section 312 of the voice coil motor 301 drives the first push rod 202 to slide with the preset speed via the connecting plate 302, thereby allowing the third liquid 820 to be discharged from the first liquid discharging nozzle 830 at the preset flow rate to generate microcroplets with uniform sizes. In other embodiments of the present application, the voice coil motor 301 can also have a structure of any other type.

Furthermore, as shown in FIGS. 43 to 44, the housing 100 includes a first mounting end surface 141 and a second mounting end surface 143 opposite to each other. A first mounting hole 142 and a second mounting hole 144 opposite to each other are respectively provided on the first mounting end surface 141 and the second mounting end surface 143. The primary section 311 of the voice coil motor 301 further includes a first mounting plate 3114 and a second mounting plate 3115 respectively and detachably fixed in the first mounting hole 142 and the second mounting hole 144. The two magnets of the first pair of magnets 3111 are respectively mounted at one end of the first mounting plate 3114 and at one end of the second mounting plate 3115 in the sliding direction of the secondary 312. The two magnets in the second pair of magnets 3112 are respectively mounted at the other end of the first mounting plate 3114 and at the other end the second mounting plate 3115 in the sliding direction of the secondary 312. The voice coil motor 301 can be entirely detached from the housing 100 or the assembled voice coil motor 301 can be entirely mounted on the housing 100, thereby ensuring the assembly precision of the voice coil motor 301, and increasing the convenience of mounting and detaching the voice coil motor 301. As an implementation manner, the first mounting hole 142 and the second mounting hole 144 both are rectangular holes with rounded corners, correspondingly, the first mounting plate 3114 and the second mounting plate 3115 both are rectangular plates with rounded corners. The first mounting plate 3114 and the second mounting plate 3115 can be respectively fixed in the first mounting hole 142 and the second mounting hole 144 via screws. Botha side surface of the first mounting plate 3114 and a side surface of the second mounting plate 3115, which are opposite to each other, have rectangular grooves allowing for mounting the first pair of magnets 3111 and the second pair of magnets 3112. The first pair of magnets 3111 are mounted in the rectangular grooves of the first pair of mounting plates, and the second pair of magnets 3112 are mounted in the rectangular grooves of the second pair of mounting plates.

Figure 38:
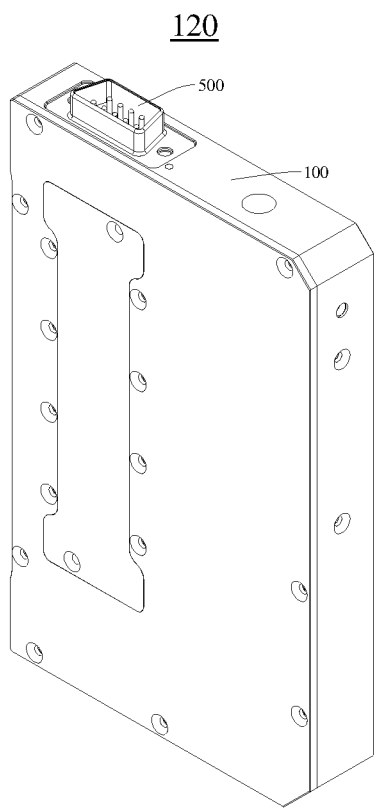
FIG. 38 is a schematic side view of overall structure of a liquid driving mechanism provided by an embodiment of the present application.

Yet furthermore, the housing 100 is hollow and in the shape of a cuboid. The first volume-variable assembly 200 and the linear motor assembly 300 of the first liquid driving mechanism 120 both are mounted inside the housing 100. A connecting hole is provided on one end surface of the housing 100. A plurality of housings 100 can be mounted on a basal body in parallel via the connecting holes. A plurality of first liquid driving mechanisms 120 mounted in parallel can simultaneously control the generation processes of a plurality of microdroplets, thereby significantly increasing the generation efficiency of the microdroplets. As an implementation manner, as shown in FIGS. 38, 39, and 43, in the operation process of the first liquid driving mechanism 120, the housing 100 has a top end surface 145 and a bottom end surface 140 opposite to each other in a spatial vertical direction. The extension direction of the first syringe barrel 201 in the housing 100 and the sliding direction of the secondary section 312 of the voice coil motor 301 both are the spatial vertical direction. The housing 100 has two side surfaces 150 opposite to each other and arranged in a direction from the first syringe barrel 201 to the voice coil motor 301, and has a first mounting end surface 141 and a second mounting end surface 143 opposite to each other and arranged in a direction from the first mounting plate 3114 to the second mounting plate 3115. In the process of mounting the plurality of liquid driving mechanisms in parallel, the first mounting end surfaces 141 and the second mounting end surfaces 143 of the plurality of housings 100 are attached to one after another. The connecting holes of the housing 100 are disposed on the same side surface 150 of the housings 100, or the connecting holes of the housing 100 are respectively disposed at two side surfaces 150. All of the housings 100 are fixedly mounted on the basal body via screws connected in threaded connecting holes. In a specific embodiment, each of the housings 100 has a dimension of 18 mm in the extension parallel direction, namely, a distance between oppositely arranged the first mounting end surface 141 and the second mounting end surface 143 of the housing 100 is 18 mm. The plurality of liquid driving mechanisms 120 mounted in parallel can control the third liquid 820 to be discharged from the first liquid discharging nozzle 830 at the preset flow rate and with the preset flow quantity in a plurality of reagent tanks spaced by a distance of 18 mm, thereby effectively generating the microdroplets. In other embodiments of the present application, the distance between the plurality of liquid driving mechanisms 120 mounted in parallel can also be any other size, as long as it is matched with the distances between the plurality of reagent tanks.

The present application further provides a liquid driving method based on the liquid driving mechanism 120 in the above-described technical solutions. The liquid driving method includes: the linear motor assembly 300 driving the first push rod 202 to press the first driving liquid 810 stored in the first syringe barrel 201, and the first driving liquid 810 pressing the third liquid 820 stored in the first liquid discharging nozzle 830 to discharge the third liquid 820 from the outlet end of the first liquid discharging nozzle 830. The above-described liquid driving method takes advantage of the incompressibility of the first driving liquid 810 to ensure that the third liquid 820 is able to be discharged from the outlet end of the first liquid discharging nozzle 830 at the preset flow rate and with the preset flow quantity, even though the outlet end of the first liquid discharging nozzle 830 vibrates at a high frequency. It can be understood that the first driving liquid 810 is immiscible with the third liquid 820, and there is no substance exchange therebetween. Generally, a density of the first driving liquid 810 is smaller than a density of the third liquid 820. Optionally, the first driving liquid 810 can be a mineral oil, or alkane, and so on. As an implementation manner, the third liquid 820 discharged from the first liquid discharging nozzle 830 falls into a container containing the first driving liquid 810 and then descends in the first driving liquid 810. The linear motor assembly 300 not only has a higher motion precision, but also enables the magnitude of the current to be adjusted conveniently according to the actual operation conditions such as the liquid discharging speed, the liquid discharging pressure, and so on, thereby ensuring that the first push rod 202 can slide at a preset speed or slides for a preset distance, and allowing the third liquid 820 to be discharged from the outlet end of the first liquid discharging nozzle 830 accurately at the preset flow rate and with the preset flow quantity. The liquid driving method provided by the present application can accurately control the volume of the generated microdroplet.

In an embodiment of the present application, as shown in FIGS. 40-41 and 48-49, the liquid driving mechanism 120 further includes a reversing valve 400 having a first reversing port 411, a second reversing port 412, and a third reversing port 413 which are respectively in communication with the inlet end of the first liquid discharging nozzle 830, the liquid inlet/outlet, and the reservoir storing the first liquid driving liquid 810. After an operation of the reversing valve 400, the first reversing port 411 can be in communication with the second reversing port 412, or the third reversing port 413 can be in communication with the second reversing port 412. The reversing valve 400 controls the liquid driving mechanism 120 achieve at least two following modes: 1. the liquid inlet/outlet of the first volume-variable assembly 200 communicates with the inlet end of the first liquid discharging nozzle 830, and driven by the linear motor assembly 300, the first volume-variable assembly 200 provides a liquid driving force for the first liquid discharging nozzle 830, so as to discharge the third liquid 820 in the first liquid discharging nozzle 830 from the outlet end of the first liquid discharging nozzle 830, or to suck the third liquid 820 from the outlet end of the first liquid discharging nozzle 830 into the first liquid discharging nozzle 830; 2. the liquid inlet/outlet of the first volume-variable assembly 200 communicates with the reservoir, and driven by the linear motor assembly 300, the first volume-variable assembly 200 sucks the first driving liquid 810 in the reservoir into the first syringe barrel 201 of the first volume-variable assembly 200, or presses the driving liquid in the first volume-variable assembly 200 into the reservoir.

Furthermore, as shown in FIGS. 48-49, the reversing valve 400 includes a valve body 410 and a communicating block 420. The valve body 410 includes the first reversing port 411, the second reversing port 412, and the third reversing port 413. A first flow channel 421, a second flow channel 422, and a third flow channel 423 separate from each other are provided in the communicating block 420 and all pass through the communicating block 420. One end of the flow channel 421, one end of the flow channel 422, and one end of the flow channel 423 are respectively connected to the first reversing port 411, the second reversing port 412, and the third reversing port 413. The other end of the flow channel 421, the other end of the flow channel 422, and the other of the flow channel 423 are respectively connected to the inlet end of the first liquid discharging nozzle 830, the liquid inlet/outlet, and the reservoir storing the first liquid driving liquid 810. The communicating block 420 provided with the plurality of flow channels has the advantages of simple structure and stable communication. Furthermore, inner surfaces of the flow channel 421, the flow channel 422, and the flow channel 423 are polished and have transition regions of round corners. There is no dead space on the inner surfaces of the flow channel 421, the flow channel 422, and the flow channel 423, thus effectively avoiding residual bubbles and adsorption of bubbles.

Figure 50:
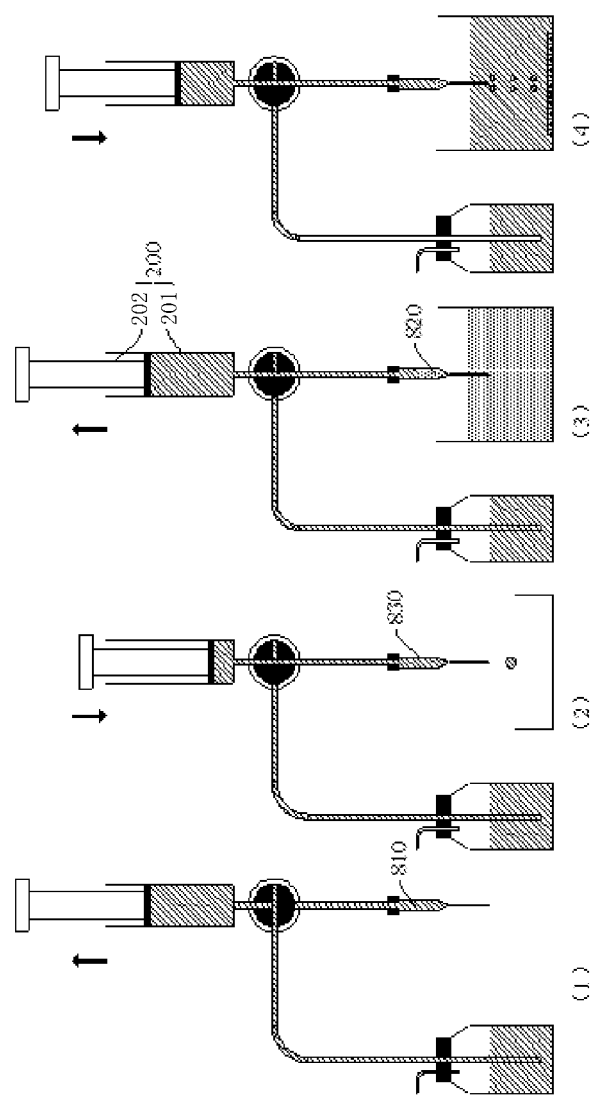
FIG. 50 is a schematic view illustrating a process of a liquid driving method provided by an embodiment of the present application.

As shown in FIG. 50, the present application further provides another liquid driving method based on the liquid driving mechanism 120 in the above-described technical solutions. The method includes steps of: 1. communicating, by means of the reversing valve 400, the liquid inlet/outlet of the first syringe barrel 201 with the reservoir, and driving, by the linear motor assembly 300, the first push rod 202 to slide in the first syringe barrel 201 to change the volume of the first syringe barrel 201, so as to suck the first driving liquid 810 in the reservoir into the first syringe barrel 201; 2. communicating, by means of the reversing valve 400, the liquid inlet/outlet of the first syringe barrel 201 with the inlet end of the first liquid discharging nozzle 830, and driving, by the linear motor assembly 300, the first push rod 202 to slide in the first syringe barrel 201 to change the volume of the first syringe barrel 201, so as to discharge the gas in the first syringe barrel 201 and in the first liquid discharging nozzle 830; 3. inserting the outlet end of the first liquid discharging nozzle 830 into the third liquid 820, maintaining, by means of the reversing valve 400, the communication between the liquid inlet/outlet of the first syringe barrel 201 and the inlet end of the first liquid discharging nozzle 830, and driving, by the linear motor assembly 300, the first push rod 202 to slide in the first syringe barrel 201 to change the volume of the first syringe barrel 201, so as to suck the third liquid 820 into the first liquid discharging nozzle 830; 4. communicating, by means of the reversing valve 400, the liquid inlet/outlet of the first syringe barrel 201 with the inlet end of the first liquid discharging nozzle 830, and driving, by the linear motor assembly 300, the first push rod 202 to slide in the first syringe barrel 201 to change the volume of the first syringe barrel 201, so as to discharge the third liquid 820 stored in the first liquid discharging nozzle 830 from the outlet end 112 of the first liquid discharging nozzle 830 with the preset flow rate.

Furthermore, in the above-described liquid driving method, the linear motor assembly 300 runs at a constant speed to drive the first push rod 202 to slide in the first syringe barrel 201 at a constant speed, which allows the first driving liquid 810 to be sucked into the first syringe barrel 201 with a uniform flow rate, or allowing the third liquid 820 to be discharged from the first syringe barrel 201, thereby ensuring the stability of the entire generation process of the microdroplets and the uniformity of the volume size of the generated microdroplets.

As an implementation manner, as shown in FIGS. 38 to 43, the housing 100 is in the shape of a hollow cuboid. The reversing valve 400 is fixedly mounted at a position inside the housing 100 proximate to the bottom surface 140 and one side surface 150. The first volume-variable assembly 200 is mounted above the communicating block 420 in the reversing valve 400. The voice coil motor 301 is mounted on a side surface of the first volume-variable assembly 200. The secondary section 312 of the voice coil motor 301 is fixedly connected to the first volume-variable assembly 200 via the connecting plate 302 therebetween. The guiding element 303 is mounted inside the housing 100 and between the voice coil motor 301 and the first syringe barrel 201 of the first volume-variable assembly 200. The liquid driving mechanism 120 further includes a power supply interface 500. The power supply interface 500 is disposed on the top surface 145 of the housing 100 and electrically connected to the voice coil motor 301, the reversing valve 400, and the displacement sensor respectively. The power supply interface 500 is further electrically connected to an external power supply, so as to supply power to the components in the liquid driving mechanism 120.

The above-described embodiments can be widely applied to the application fields such as medical clinical test, preparation of nano-material, food and environment detections, biochemical analysis, and so on. In a specific application scenario, the generating device and the generating method of the microdroplet 199 provided by the present application are applied to the polymerase chain reaction (PCR).

The technical features of the above-described embodiments may be arbitrarily combined. In order to make the description simple, not all possible combinations of the technical features in the above embodiments are described. However, as long as there is no contradiction in the combination of these technical features, the combinations should be in the scope of the present application.

What described above are only several implementations of the present application, and these embodiments are specific and detailed, but not intended to limit the scope of the present application. It should be understood by the skilled in the art that various modifications and improvements can be made without departing from the conception of the present application, and all fall within the protection scope of the present application. Therefore, the patent protection scope of the present application is defined by the appended claims It should be noted that the ordinal of components defined in this application, such as "the first" and "the second", is only used to distinguish the described component, and no priority or technological meaning is intended. When a component is defined as "connected to" or "coupled to" the other component, it means that the component can be directly or indirectly connected or coupled to the other component. In the description of the present disclosure, it is to be understood that terms such as "upper," "lower," "front," "rear," "left," "right," "vertical," "horizontal," "top," "bottom," "inner," "outer," "clockwise," "anticlockwise," should be construed to refer to the orientation as then described or as shown in the drawings under discussion. These relative terms are just for convenience of description rather than to indicate or imply that the referred device or component must be arranged in such a specific direction or to be operated or configured in specific direction. Therefore, the above mentioned terms shall not be interpreted as a limitation to the present application.

In the present application, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

In the present application, the relational terms such as "first" and "second" are used to differentiate an entity or operation from another entity or operation, and do not require or imply any actual relationship or sequence between these entities or operations. Moreover, the terms "include," "comprise," and any variation thereof are intended to cover a non-exclusive inclusion. Therefore, a process, method, object, or device, which includes a series of elements, not only includes such elements, but also includes other elements not specified expressly, or may further include inherent elements of the process, method, object, or device. If no more limitations are made, an element limited by "include a/an . . . " does not exclude other same elements existing in the process, the method, the article, or the device which includes other elements.

The various embodiments of the present application are described progressively, where each embodiment is described by emphasizing its differences form some other embodiments. For portions of the various embodiments that are similar to each other, references can be made to each other.

The descriptions of the provided embodiments enable those skilled in the art to implement or use this application. Various modifications to these embodiments will be apparent to those skilled in the art. The general principles defined herein can be implemented in other embodiments without departing from the spirit or scope of the present application. Therefore, the present application will not be limited to the embodiments illustrated in this application, but should conform to the widest scope consistent with the principles and novel features provided herein.

What is claimed is:

1. A microdroplet generating method, comprising steps of:

S201, providing a liquid discharging nozzle having an outlet end and storing a first liquid therein and providing a microdroplet container storing a second liquid therein and having an opening, wherein the first liquid and the second liquid are any two immiscible liquids or any two liquids having an interfacial reaction therebetween;

S202, inserting the outlet end of the liquid discharging nozzle below the liquid surface of the second liquid through the opening of the microdroplet container;

S203, controlling the outlet end of the liquid discharging nozzle to move below the liquid surface of the second liquid, while discharging the first liquid from the outlet end of the liquid discharging nozzle, so that the first liquid discharged from the outlet end of the liquid discharging nozzle forms a droplet attached to the outlet end of the liquid discharging nozzle, wherein the outlet end of the liquid discharging nozzle is instantaneously accelerated to such a value of instantaneous acceleration that the droplet is instantaneously detached from the outlet end of the liquid discharging nozzle, thereby forming a microdroplet below the liquid surface of the second liquid.

2. The microdroplet generating method of claim 1, wherein in S203, the outlet end of the liquid discharging nozzle makes a periodic motion including an instantaneous accelerated motion below the liquid surface of the second liquid.

3. The microdroplet generating method of claim 2, wherein in S203, during the periodic motion of the outlet end of the liquid discharging nozzle below the liquid surface of the second liquid, a speed of the outlet end of the liquid discharging nozzle varies in a form of a rectangular wave.

4. The microdroplet generating method of claim 3, wherein the speed of the outlet end of the liquid discharging nozzle varies in a form of a square wave.

5. The microdroplet generating method of claim 4, wherein in S203, the speed of the outlet end of the liquid discharging nozzle in a first half motion period and that in a second half motion period are identical but in opposite directions.

6. The microdroplet generating method of claim 1, wherein in S203, the outlet end of the liquid discharging nozzle moves below the liquid surface of the second liquid in a direction perpendicular to, parallel to, or having an arbitrarily angle relative to an extension direction of the liquid discharging nozzle.

7. A microdroplet generating method, comprising steps of:
S211, providing a liquid discharging nozzle having an outlet end and storing a first liquid therein and providing a microdroplet container storing a second liquid therein and having an opening, wherein the first liquid and the second liquid are any two immiscible liquids or any two liquids having an interfacial reaction therebetween;
S212, inserting the outlet end of the liquid discharging nozzle below a liquid surface of the second liquid through the opening of the microdroplet container;
S213, controlling the outlet end of the liquid discharging nozzle to move at a periodically changed speed below the liquid surface of the second liquid, and in a first half period and a second half period of a speed variation, the speed of the outlet end of the liquid discharging nozzle changing monotonously, the first liquid being discharged from the outlet end of the liquid discharging nozzle, the first liquid discharged from the outlet end of the liquid discharging nozzle being formed into a droplet attached to the outlet end of the liquid discharging nozzle, the droplet being detached from the outlet end of the discharging nozzle during the moving of the outlet end of the liquid discharging nozzle, thereby forming a microdroplet below the liquid surface of the second liquid.

8. The microdroplet generating method of claim 7, wherein in S213, the speed of the outlet end of the liquid discharging nozzle is center symmetrical relative to a midpoint which is a middle time point of the period of the speed variation; or
in S213, the outlet end of the liquid discharging nozzle moves with a uniform acceleration in both the first half period and the second half period of one speed variation period.

9. The microdroplet generating method of claim 8, wherein in S213, an acceleration and a moving trajectory of the outlet end of the liquid discharging nozzle moving below the liquid surface of the second liquid are periodically changed.

10. The microdroplet generating method of claim 9, wherein in S213, the speed of the outlet end of the liquid discharging nozzle moving below the liquid surface of the second liquid varies in a form of a cosine curve.

11. The microdroplet generating method of claim 10, wherein one droplet is detached from the outlet end of the liquid discharging nozzle and forms the microdroplet in each of an accelerating stage of the first half period and an accelerating stage of the second half period of the speed variation of the outlet end of the liquid discharging nozzle.

12. The microdroplet generating method of claim 10, wherein in S213, a moving trajectory of the outlet end of the liquid discharging nozzle moving below the liquid surface of the second liquid comprises one of or a combination of a straight line segment, an arc-shaped line segment, or a polygon.

13. The microdroplet generating method of claim 9, wherein in S213, a frequency of the periodic motion of the outlet end of the liquid discharging nozzle moving below the liquid surface of the second liquid is between 0.1 Hz and 200 Hz.

14. The microdroplet generating method of claim 7, wherein in S213, magnitudes of the accelerations of the outlet end of the liquid discharging nozzle in the first half period and in the second half period are identical.

15. The microdroplet generating method of claim 7, wherein in S213, the first liquid is continuously discharged from the outlet end of the liquid discharging nozzle.

16. The microdroplet generating method of claim 15, wherein in S203, the first liquid is discharged from the outlet end of the liquid discharging nozzle at a constant flow rate.

17. The microdroplet generating method of claim 1, wherein in S203, the value of instantaneous acceleration of the outlet end of the liquid discharging nozzle reaches a maximum value at the moment the direction of the velocity of the outlet end of the liquid discharging nozzle changes.

18. The microdroplet generating method of claim 1, wherein in S203, the outlet end of the liquid discharging nozzle is instantaneously accelerated at the moment the volume of the droplet reaches a set value.

19. The microdroplet generating method of claim 1, wherein in S203, the speed of the outlet end of the liquid discharging nozzle is zero before the outlet end of the liquid discharging nozzle instantaneously accelerates.

* * * * *